(12) United States Patent
Barrack et al.

(10) Patent No.: US 8,927,488 B2
(45) Date of Patent: *Jan. 6, 2015

(54) PEGYLATED C-PEPTIDE

(75) Inventors: Sheri Barrack, Corte Madre, CA (US);
James Callaway, San Diego, CA (US);
Michelle Mazzoni, San Diego, CA (US)

(73) Assignee: Cebix, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/109,522

(22) Filed: May 17, 2011

(65) Prior Publication Data

US 2012/0178676 A1    Jul. 12, 2012

Related U.S. Application Data

(60) Provisional application No. 61/345,293, filed on May 17, 2010, provisional application No. 61/448,402, filed on Mar. 2, 2011.

(51) Int. Cl.
| | | |
|---|---|---|
| A61K 38/16 | (2006.01) | |
| A61P 3/10 | (2006.01) | |
| C07K 14/00 | (2006.01) | |
| A61K 47/48 | (2006.01) | |
| C07K 14/62 | (2006.01) | |

(52) U.S. Cl.
CPC .......... *A61K 47/48215* (2013.01); *C07K 14/00* (2013.01); *C07K 14/62* (2013.01); *A61K 38/16* (2013.01)
USPC ............. 514/3.2; 514/6.9; 514/21.3; 530/324

(58) Field of Classification Search
CPC . A61K 38/16; A61K 47/48215; C07K 14/62; C07K 14/00
See application file for complete search history.

(56) References Cited

U.S. PATENT DOCUMENTS

| | | | |
|---|---|---|---|
| 4,904,584 | A | 2/1990 | Shaw |
| 5,252,714 | A | 10/1993 | Harris et al. |
| 5,541,543 | A | 7/1996 | Arnaud |
| 5,612,460 | A | 3/1997 | Zalipsky |
| 5,629,384 | A | 5/1997 | Veronese et al. |
| 5,650,234 | A | 7/1997 | Dolence et al. |
| 5,672,662 | A | 9/1997 | Harris et al. |
| 5,739,208 | A | 4/1998 | Harris |
| 5,824,784 | A | 10/1998 | Kinstler et al. |
| 5,840,900 | A | 11/1998 | Greenwald et al. |
| 5,880,131 | A | 3/1999 | Greenwald et al. |
| 5,900,461 | A | 5/1999 | Harris |
| 5,932,462 | A | 8/1999 | Harris et al. |
| 5,990,237 | A | 11/1999 | Bentley et al. |
| 6,348,558 | B1 | 2/2002 | Harris et al. |
| 6,362,254 | B2 | 3/2002 | Harris et al. |
| 6,376,470 | B1 | 4/2002 | Greenwald et al. |
| 6,436,386 | B1 | 8/2002 | Roberts et al. |
| 6,437,025 | B1 | 8/2002 | Harris et al. |
| 6,448,369 | B1 | 9/2002 | Bentley et al. |
| 6,495,659 | B2 | 12/2002 | Bentley et al. |
| 6,602,498 | B2 | 8/2003 | Shen |
| 6,664,331 | B2 | 12/2003 | Harris et al. |
| 6,730,334 | B2 | 5/2004 | Zhao |
| 6,774,180 | B2 | 8/2004 | Kozlowski et al. |
| 6,838,528 | B2 | 1/2005 | Zhao |
| 7,026,440 | B2 | 4/2006 | Bentley et al. |
| 7,030,278 | B2 | 4/2006 | Harris et al. |
| 7,053,150 | B2 | 5/2006 | Kozlowski et al. |
| 7,087,247 | B2 | 8/2006 | Li et al. |
| 7,157,546 | B2 | 1/2007 | Kozlowski |
| 7,223,803 | B2 | 5/2007 | Harris et al. |
| 7,265,186 | B2 | 9/2007 | Zhao |
| 7,419,600 | B2 | 9/2008 | Harris et al. |
| 7,432,330 | B2 | 10/2008 | Kozlowski et al. |
| 7,432,331 | B2 | 10/2008 | Kozlowski et al. |
| 7,511,094 | B2 | 3/2009 | Kozlowski |
| 7,528,202 | B2 | 5/2009 | Harris et al. |
| 7,589,157 | B2 | 9/2009 | Zhao |
| 7,872,072 | B2 | 1/2011 | Bentley et al. |
| 2001/0043934 | A1 * | 11/2001 | L'Italien et al. ............. 424/400 |
| 2003/0069170 | A1 | 4/2003 | Soltero et al. |
| 2003/0143596 | A1 * | 7/2003 | Bentley et al. .................... 435/6 |
| 2003/0228275 | A1 | 12/2003 | Ekwuribe et al. |
| 2003/0228652 | A1 | 12/2003 | Radhakrishnan et al. |
| 2005/0009988 | A1 | 1/2005 | Harris et al. |
| 2005/0058620 | A1 | 3/2005 | Nakamoto et al. |
| 2005/0112088 | A1 | 5/2005 | Zhao et al. |
| 2006/0194940 | A1 | 8/2006 | Kozlowski |
| 2007/0031371 | A1 | 2/2007 | McManus et al. |

(Continued)

FOREIGN PATENT DOCUMENTS

| | | |
|---|---|---|
| EP | 1 932 855 | 6/2008 |
| GB | 2 104 382 | 3/1983 |

(Continued)

OTHER PUBLICATIONS

NOF Corporation catalogue Ver. 8 (Apr. 2006), p. 1-60.*
Adagen® (pegademase bovine) Injection (revised May 2010).
Banerjee, S.S. et al., "Poly(ethylene glycol)-Prodrug Conjugates: Concept, Design, and Applications," *J. Drug Delivery* 2012, 1-17.
Bukowski, R.M. et al., "Treating Cancer with PEG Intron," *Cancer* 2002, 95(2), 389-396.
Caliceti et al., "Pharmacokinetic and Biodistribution Properties of Poly(ethyleneglycol)-Protein Conjugates," *Adv. Drug Deliv. Rev.* 2003, 55, 1261-1277.
Chapman, A.P., "PEGylated Antibodies and Antibody Fragments for Improved Therapy: A Review," *Adv. Drug Deliv. Rev.* 2002, 54(4), pp. 531-545.

(Continued)

*Primary Examiner* — Julie Ha
*Assistant Examiner* — Li Ni Komatsu
(74) *Attorney, Agent, or Firm* — Morrison & Foerster LLP

(57) ABSTRACT

The present invention relates to modified forms of C-peptide, and methods for their use. In one aspect, the modified forms of C-peptide comprise PEGylated C-peptide derivatives comprising at least one PEG group attached to the N-terminus, which exhibit superior pharmacokinetic and biological activity in vivo.

13 Claims, 30 Drawing Sheets

(56) References Cited

U.S. PATENT DOCUMENTS

| | | | |
|---|---|---|---|
| 2007/0105809 A1* | 5/2007 | Rusconi | 514/44 |
| 2009/0234070 A1 | 9/2009 | Kozlowski | |
| 2009/0281029 A1* | 11/2009 | Nojima et al. | 514/12 |

FOREIGN PATENT DOCUMENTS

| | | | | |
|---|---|---|---|---|
| GB | 2104382 A | * | 3/1983 | A61K 37/26 |
| WO | WO-98/13384 | | 4/1998 | |
| WO | WO-99/07735 | | 2/1999 | |
| WO | WO-00/41546 | | 7/2000 | |
| WO | WO 0041546 | * | 7/2000 | A61K 9/14 |
| WO | WO-02/22211 | | 3/2002 | |
| WO | WO-02/38129 | | 5/2002 | |
| WO | WO-02/098446 | | 12/2002 | |
| WO | WO-03/022208 | | 3/2003 | |
| WO | WO-03/022210 | | 3/2003 | |
| WO | WO-03/022996 | | 3/2003 | |
| WO | WO-2004/016647 | | 2/2004 | |
| WO | WO-2004/083234 | | 9/2004 | |
| WO | WO-2005/000360 | | 1/2005 | |
| WO | WO-2005/002597 | | 1/2005 | |
| WO | WO-2005/028539 | | 3/2005 | |
| WO | WO-2005/039627 | | 5/2005 | |
| WO | WO-2005/107815 | | 11/2005 | |
| WO | WO-2005/108463 | | 11/2005 | |
| WO | WO-2005/118638 | | 12/2005 | |
| WO | WO-2006/097521 | | 9/2006 | |
| WO | WO-2006/129095 | | 12/2006 | |
| WO | WO-2007/015069 | | 2/2007 | |
| WO | WO-2008/012528 | | 1/2008 | |
| WO | WO 2008012528 A1 | * | 1/2008 | A61K 47/48 |
| WO | WO-2008/015099 | | 2/2008 | |
| WO | WO-2008/058691 | | 5/2008 | |
| WO | WO-2009/045122 | | 4/2009 | |
| WO | WO-2009/117410 | | 9/2009 | |
| WO | WO-2010/033204 | | 3/2010 | |
| WO | WO-2010/033207 | | 3/2010 | |
| WO | WO 2010033204 A2 | * | 3/2010 | A61K 47/48 |
| WO | WO-2011/056447 | | 5/2011 | |
| WO | WO-2011/081915 | | 7/2011 | |
| WO | WO-2011/146518 | | 11/2011 | |

OTHER PUBLICATIONS

Davis, F.F., "The Origin of Pegnology," *Adv. Drug Deliv. Rev.* 2002, 54(4), pp. 457-458.
Declaration of Mark C. Manning, Ph.D., for U.S. Appl. No. 13/463,887, filed Jun. 7, 2013, 335 pages.
Faber, O.K. et al., "Kinetics of Human Connecting Peptide in Normal and Diabetic Subjects," *J. Clin. Invest.* 1978, 197-203.
Fishburn, C.S., "The Pharmacology of PEGylation: Balancing PD with PK to Generate Novel Therapeutics," *J. Pharm. Sci.* 2008, 1-17.
Foyt, H. et al., "Pharmacokinetics, Safety, and Tolerability of a Long-Acting C-Peptide (CBX129801) in Patients with Type 1 Diabetes," Presented at 48th Annual Meeting of the European Association for the Study of Diabetes (EASD), Berlin, Germany, Oct. 1-5, 2012.
Ganson, N.J. et al., "Control of hyperuricemia in subjects with refractory gout, and introduction of antibody against poly(ethylene glycol) (PEG), in a phase I trial of subcutaneous PEGylated urate oxidase," *Arthritis Res. Ther.* 2005, 8(1), R12.
Garay, R.P. and J.P. Labaune, "Immunogenicity of Polyethylene Glycol (PEG)," *Open Conf. Proc. J.* 2011, 2, 104-107.
Gong, N. et al., "Site-specific PEGylation of exenatide analogus markedly improved their glucoregulatory activity," *Br. J. Pharmacol.* 2011, 163, 399-412.
"Highlights of Prescribing Information" for ONCASPAR® (Revised Jul. 2006).
"Highlights of Prescribing Information" for OMONTYS® (Revised Mar. 2012).
Hinds, K.D. et al., "Effects of PEG Conjugation on Insulin Properties," *Adv. Drug Deliv. Rev.* 2002, 54(4), pp. 505-530.
Important Drug Information, Feb. 2013, OMONTYS®.
International Search Report for PCT/US2011/036858, mailed Jan. 17, 2012, 5 pages.
Kinstler, O. et al., "Mono-N-terminal Poly(ethylene glycol)-protein Conjugates," *Adv. Drug Deliv. Rev.* 2002, 54(4), pp. 477-485.
Matthews, D.R. et al., "The Half-Life of Endogenous Insulin and C-Peptide in Man Assessed by Somatostatin Suppression," *Clin. Endocrinol.* 1985, 23, 71-79.
Munte et al., Solution structure of human proinsulin C-peptide, FEBS Journal, 2005, 272, pp. 4284-4293.
NOF Corporation Drug Delivery Systems Product Catalog, (2009), May.
NOF Corporation Sunbright Series PEG Products, NOF Corporation, Sunbright Series, High Quality Branched PEGs, Jun. 2010.
Pan, C.Q. et al., "Design of a long acting peptide functioning as both a glucagon-like peptide-1 receptor agonist and a glucagon receptor antagonist," *J. Biol. Chem.* 2006, 281(18), 12506-12515.
Park, A. et al., "Carbohydrate-Mediated Polyethylene Glycol Conjugation of TSH Improves Its Pharmcological Properties," *Endocrinology* 2013, 154(3), 1373-1383.
Pasut, G. et al., "Protein, Peptide and Non-peptide Drug PEGylation for Therapeutic Application," *Expert Opin. Ther. Patents* 2004, 14(6), pp. 859-894.
Pasut, G. and F.M. Veronese, "Polymer-drug conjugation, recent achievements and general strategies," *Prog. Polymer Sci.* 2007, 32(8-9), 933-61.
Payne, R.W. et al., "Product development issues for PEGylated proteins," *Pharm. Dev. Tech.* 2011, 16(5), 423-440.
Reddy, K.R. et al., "Use of Peg interferon Alfa-2a (40KD) (Pegasys®) for the Treatment of Hepatitis C," *Adv. Drug Deliv. Rev.* 2002, 54(4), pp. 571-586.
Roberts, M.J. et al., "Chemistry for Peptide and Protein PEGylation," *Adv. Drug Deliv. Rev.* 2002, 54(4), pp. 459-476.
Sato, H., "Enzymatic Procedure for Site-specific Pegylation of Proteins," *Adv. Drug Deliv. Rev.* 2002, 54(4), pp. 487-504.
Shechter, Y. et al., "Reversible PEGylation of peptide $YY_{3-36}$ prolongs its inhibition of food intake in mice," *FEBS Letters* 2005, 529, 2439-2444.
Supplemental Declaration of Mark C. Manning, Ph.D., for U.S. Appl. No. 13/463,887, filed Nov. 22, 2013, 9 pages.
Supplementary European Search Report for EP 11784109.8, mailed Dec. 10, 2013, 6 pages.
Tam et al., "Dual-action peptides: a new strategy in the treatment of diabetes-associated neuropathy," *Drug Discovery Today* 2006, 11, 254-260.
Veronese, F.M. et al., "Introduction and Overview of Peptide and Protein Pegylation," *Adv. Drug Deliv. Rev.* 2002, 54(4), pp. 453-456.
Veronese et al., "PEGylation, Successful Approach to Drug Delivery," Drug Discovery Today, 2005, 10(21), 1451-1458.
Veronese, F.M. et al., "Polyethylene Glycol-Superoxide Dismutase, a Conjugate in Search of Exploitation," *Adv. Drug Deliv. Rev.* 2002, 54(4), pp. 587-606.
Wang, Y-S et al., "Structural and Biological Characterization of Pegylated Recombinant Interferon Alpha-2b and its Therapeutic Implications," *Adv. Drug Deliv. Rev.* 2002, 54(4), pp. 547-570.
Webster, R. et al., "PEGylation of somatotropin (recombinant human growth hormone: Impact on its clearance in humans," *Xenobiotica* 2008, 38(1), 1340-1351.
Zalipsky, S., "Chemistry of Polyethylene Glycol Conjugates with Biologically Active Molecules," *Adv. Drug Deliv. Rev.* 1995, 16, pp. 157-182.

* cited by examiner

Figure 5
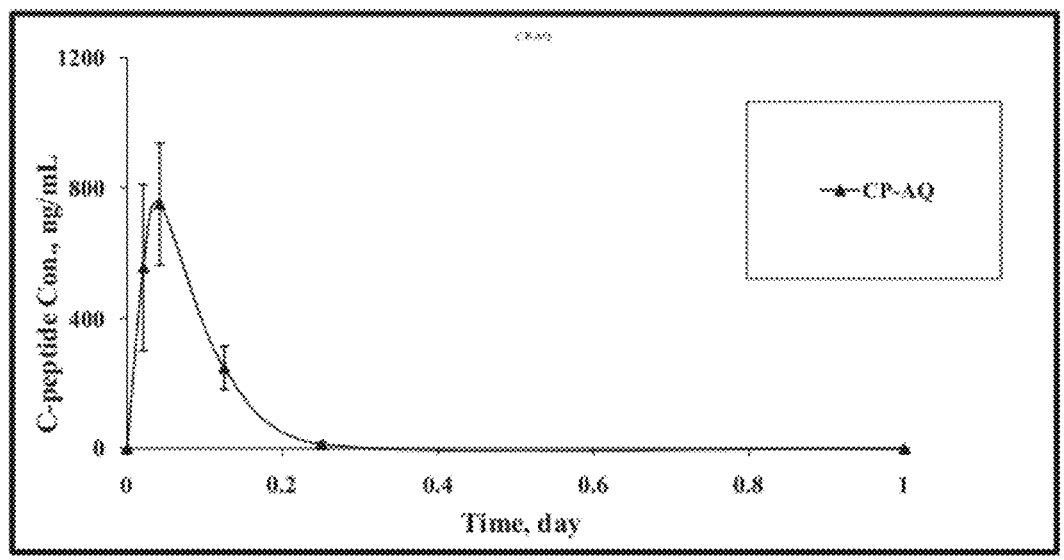
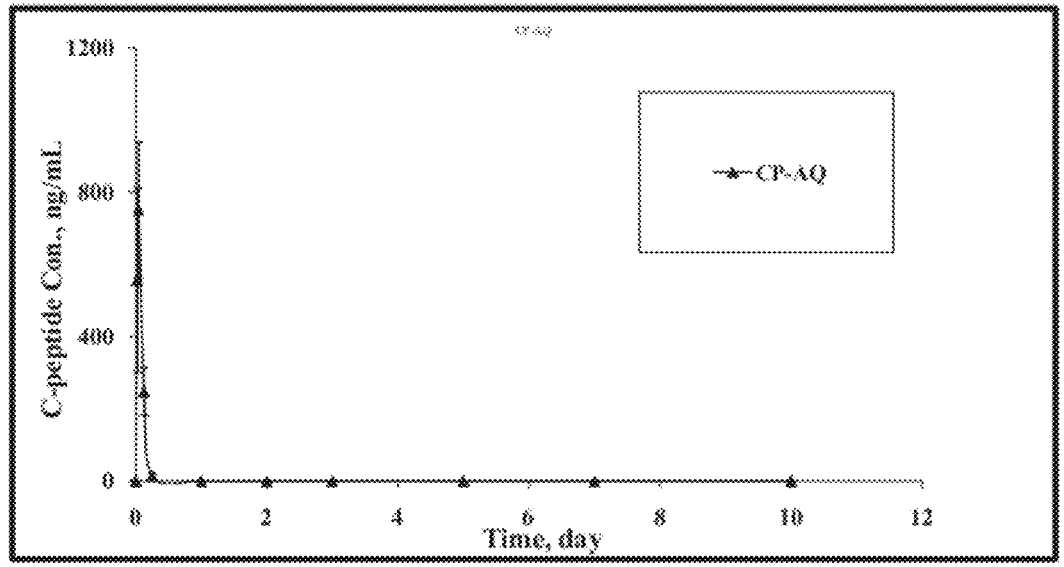

Figure 8
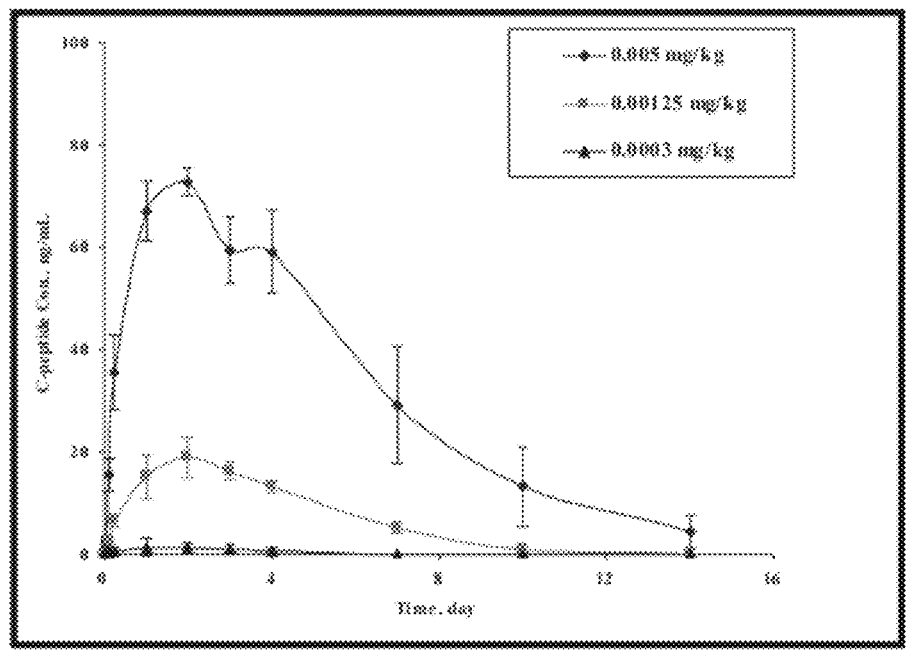
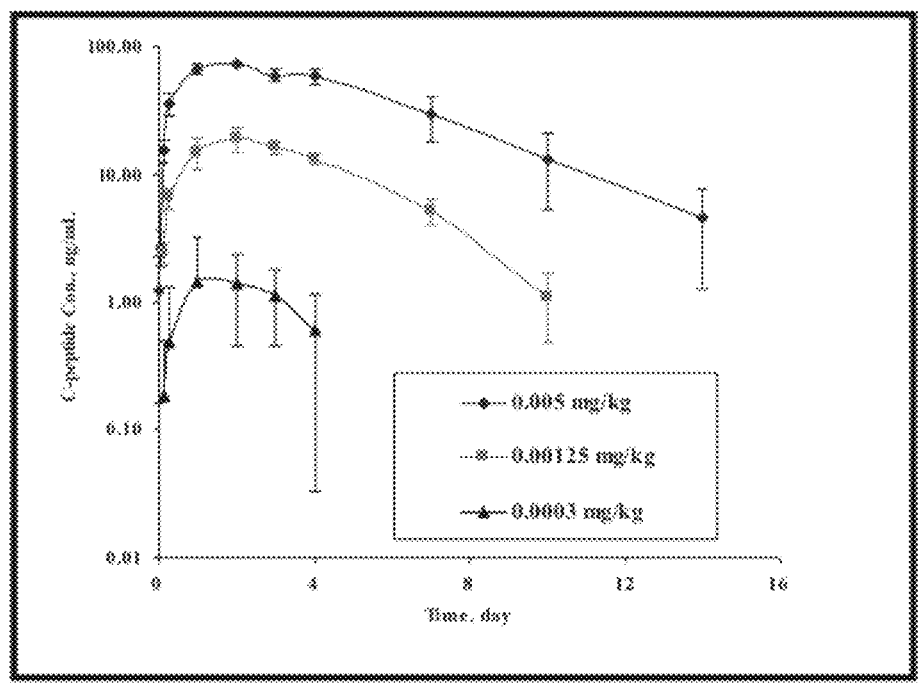

Figure 9
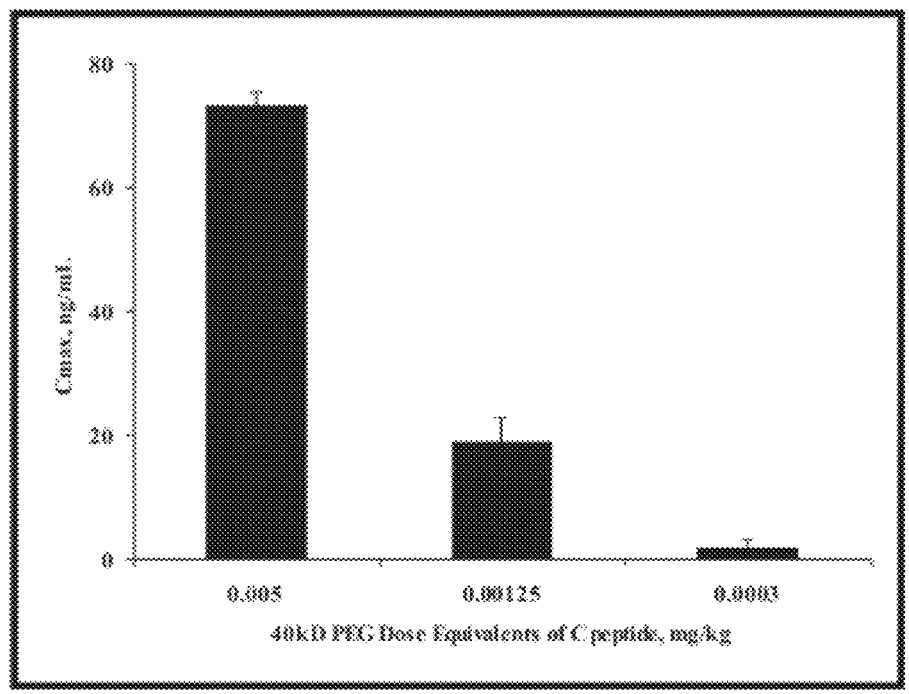
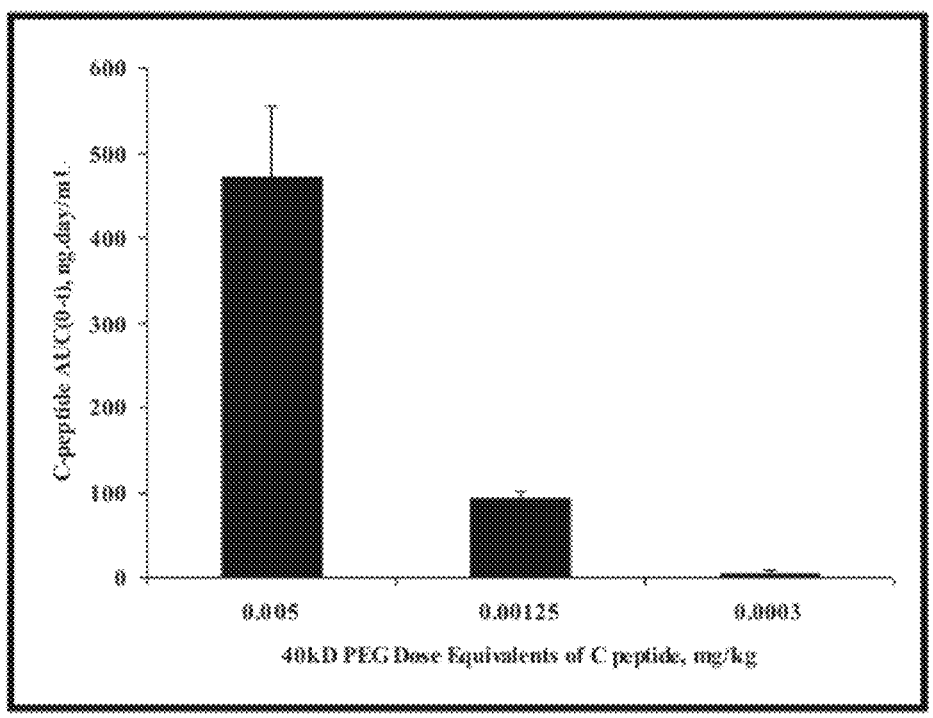

Figure 10
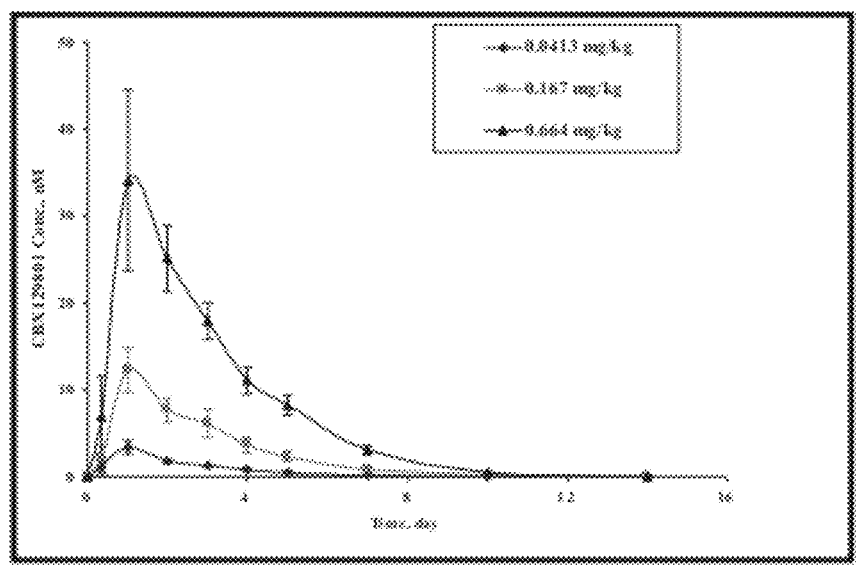
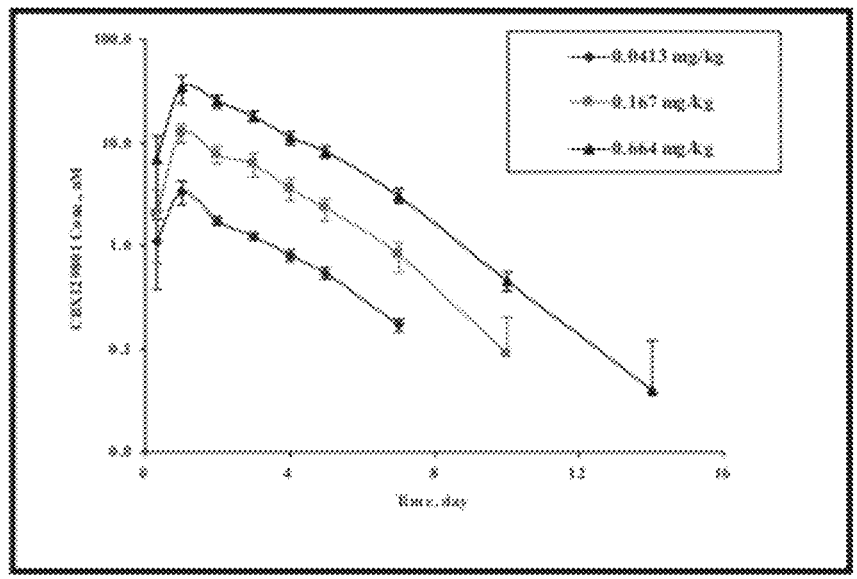

Figure 11
A
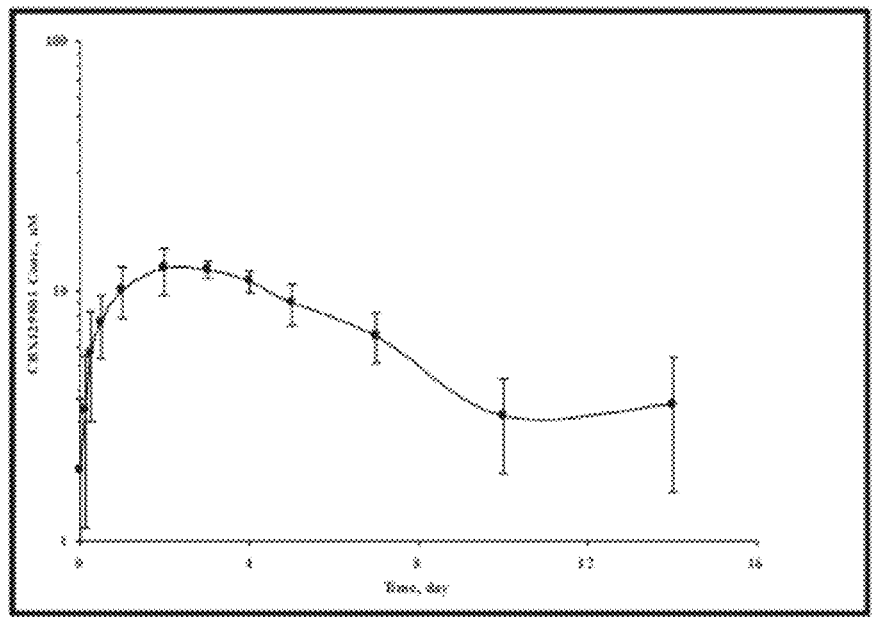
B
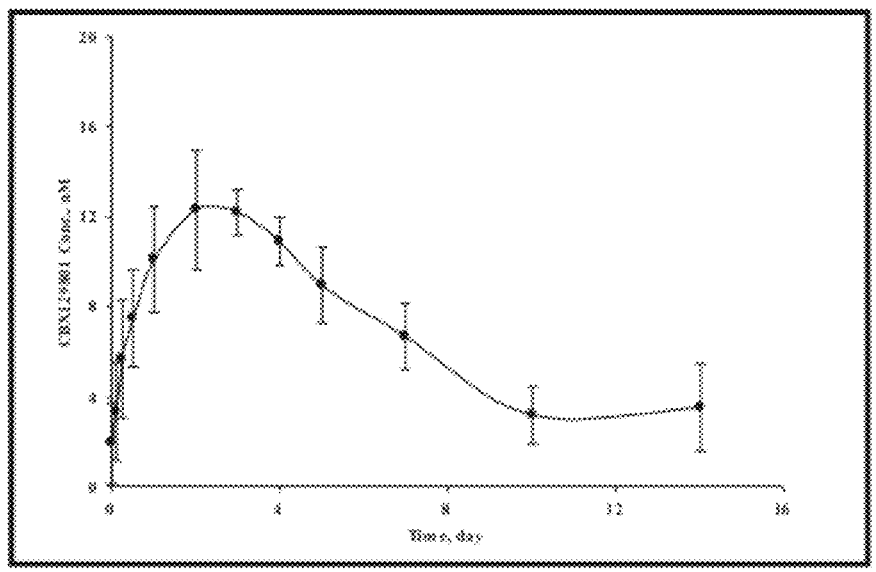

PEGYLATED C-PEPTIDE

CROSS REFERENCE TO RELATED APPLICATIONS

This application claims the benefit of priority of U.S. provisional applications Nos. 61/345,293, filed May 17, 2010, and 61/448,402, filed Mar. 2, 2011, the disclosures of which are incorporated by reference as if written herein in their entireties.

BACKGROUND OF THE INVENTION

Field of the Invention

The present invention relates to modified forms of C-peptide, and methods for their use. In one aspect, the modified forms of C-peptide comprise PEGylated C-peptide derivatives comprising at least one PEG group attached to the N-terminus which exhibit superior pharmacokinetic and biological activity in vivo.

C-peptide is the linking peptide between the A- and B-chains in the proinsulin molecule. After cleavage and processing in the endoplasmic reticulum of pancreatic islet β-cells, insulin and C-peptide are generated. C-peptide is co-secreted with insulin in equimolar amounts from the pancreatic islet β-cells into the portal circulation. Besides its contribution to the folding of the two-chain insulin structure, further biologic activity of C-peptide was questioned for many years after its discovery.

Type 1 diabetes, or insulin-dependent diabetes mellitus, is generally characterized by insulin and C-peptide deficiency, due to an autoimmune destruction of the pancreatic islet β-cells. The patients are therefore dependent on exogenous insulin to sustain life. Several factors may be of importance for the pathogenesis of the disease, e.g., genetic background, environmental factors, and an aggressive autoimmune reaction following a temporary infection (Akerblom H K et al.: *Annual Medicine* 29(5): 383-385, (1997)). Currently insulin-dependent diabetics are provided with exogenous insulin which has been separated from the C-peptide, and thus do not receive exogenous C-peptide therapy. By contrast most type 2 diabetics initially still produce both insulin and C-peptide endogenously, but are generally characterized by insulin resistance in skeletal muscle and adipose tissue.

Type 1 diabetics suffer from a constellation of long-term complications of diabetes that are in many cases more severe and widespread than in type 2 diabetes. Specifically, for example microvascular complications involving the retina, kidneys, and nerves are a major cause of morbidity and mortality in patients with type 1 diabetes.

There is increasing support for the concept that C-peptide deficiency may play a role in the development of the long-term complications of insulin-dependent diabetics. Additionally, in vivo as well as in vitro studies, in diabetic animal models and in patients with type 1 diabetes, demonstrate that C-peptide possesses hormonal activity (Wahren J et al.: *American Journal of Physiology* 278: E759-E768, (2000); Wahren J et al.: In *International textbook of diabetes mellitus* Ferranninni E, Zimmet P, De Fronzo R A, Keen H, Eds. Chichester, John Wiley & Sons, (2004), p. 165-182). Thus, C-peptide used as a complement to regular insulin therapy may provide an effective approach to the management of type 1 diabetes long-term complications.

Studies to date suggest that C-peptide's therapeutic activity involves the binding of C-peptide to a G-protein-coupled membrane receptor, activation of $Ca^{2+}$-dependent intracellular signalling pathways, and phosphorylation of the MAP-kinase system, eliciting increased activities of sodium/potassium ATPase and endothelial nitric oxide synthase (eNOS). Despite the promise of using C-peptide to treat and prevent the long-term complications of insulin-dependent diabetes, the short biological half-life and requirement to dose C-peptide multiple times per day via subcutaneous injection, or intravenous (I.V.) administration, has hindered commercial development.

The present invention is focused on the development of PEGylated versions of C-peptide that retain the biological activity of the native C-peptide and exhibit superior pharmacokinetic properties. These improved therapeutic forms of C-peptide enable the development of more effective therapeutic regimens for the treatment of the long-term complications of diabetes, and require significantly less frequent administration.

In one aspect, these therapies are targeted to diabetic patients, and in a further aspect to insulin-dependent patients. In one aspect, the insulin-dependent patients are suffering from one or more long-term complications of diabetes.

These improved methods are based on animal studies that surprisingly demonstrate that modification of C-peptide at the N-terminus of the molecule results in PEGylated versions of C-peptide that retain the biological activity of the native molecule, while exhibiting vastly superior pharmacokinetic characteristics.

SUMMARY OF THE INVENTION

In one embodiment, the present invention includes a PEGylated C-peptide comprising a PEG moiety covalently attached to the N-terminus of C-peptide. In one aspect, the PEGylated C-peptide of the invention comprises a linear polymer PEG polymer. In another aspect, the PEGylated C-peptide of the invention comprises a branched chain PEG polymer.

In another aspect of any of these PEGylated C-peptides, the PEG moiety has a molecular weight of between about 10 kDa and about 80 kDa. In another aspect, the PEG moiety has a molecular weight of between about 20 kDa and about 60 kDa. In another aspect, the PEG moiety has a molecular weight of between about 30 kDa and about 50 kDa.

In another aspect of any of these linear PEGylated C-peptides, the PEGylated C-peptide has the general formula (I):

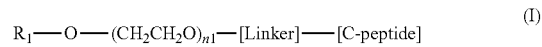

$$R_1-O-(CH_2CH_2O)_{n1}-[Linker]-[C\text{-peptide}] \quad (I)$$

wherein:
$R_1$=alkyl;
$n_1$ is 20 to 800;
the linker is selected from; —X—, —CO—, —$(CH_2)_{m2}$—, —$(CH_2)_{m1}$—CO—, —CO—$(CH_2)_{m1}$—, —CO—X—CO—, —$(CH_2)_{m1}$—X—$(CH_2)_{m1}$—, —$(CH_2)_{m1}$—CO—$(CH_2)_{m1}$—, —X—CO—X—, —X—$(CH_2)_{m1}$—X—, —CO—$(CH_2)_{m1}$—CO—, —X—CO—$(CH_2)_{m1}$—, —$(CH_2)_{m1}$—CO—X—, —X—$(CH_2)_{m1}$—CO—X—, —X—CO—$(CH_2)_{m1}$—X—, —X—CO—$(CH_2)_{m1}$—CO—X—$(CH_2)_{m1}$—X—CO—, —X—$(CH_2)_{m1}$—X—CO—$(CH_2)_{m2}$—, —X—$(CH_2)_{m1}$—CO—X—$(CH_2)_{m2}$—, —X—$(CH_2)_{m1}$—X—CO—$(CH_2)_{m2}$—X—, —X—$(CH_2)_{m1}$—X—CO—$(CH_2)_{m2}$—CO—, —X—$(CH_2)_{m1}$—CO—X—$(CH_2)_{m2}$—X—, and —X—$(CH_2)_{m1}$—CO—X—$(CH_2)_{m2}$—CO—;

wherein:
  each X is independently selected from —O—, —S—, or —NH— or is missing;
  each $m_1$ is independently 0 to 5; and
  each $m_2$ is independently 1 to 5; and
wherein the linker is attached to the N-terminal amino group of C-peptide.

In another aspect of any of these linear PEGylated C-peptides, the PEGylated C-peptide comprises a linker connecting the PEG moiety to C-peptide selected from:
  —$X_1$—$(CH_2)_{m4}$—CO—;
  —$X_1$—CO—;
  —$X_1$—CO—$(CH_2)_{m4}$—CO—;
  —$X_1$—CO—$X_2$—$(CH_2)_{m3}$—CO—; and
  —$X_1$—$(CH_2)_{m2}$—$X_2$—CO—$(CH_2)_{m4}$—CO—;
wherein:
  $X_1$ is —O—, or missing;
  $X_2$ is —NH—;
  $m_2$ is 1 to 5;
  $m_3$ is 2; and
  $m_4$ is 2 to 5.

In another embodiment, the present invention includes a PEGylated C-peptide wherein the PEGylated C-peptide has the structure:

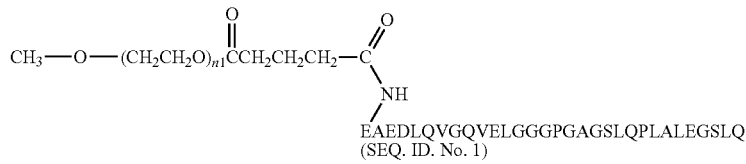

wherein $n_1$ is about 400 to about 1000.

In another embodiment, the present invention includes a PEGylated C-peptide wherein the PEGylated C-peptide has the structure:

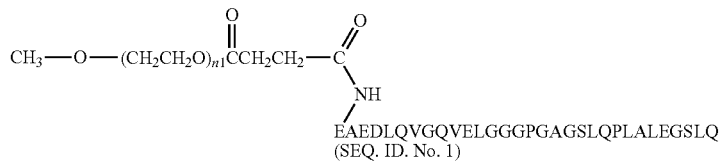

wherein $n_1$ is about 400 to about 1000.

In another embodiment, the present invention includes a PEGylated C-peptide wherein the PEGylated C-peptide has the structure:

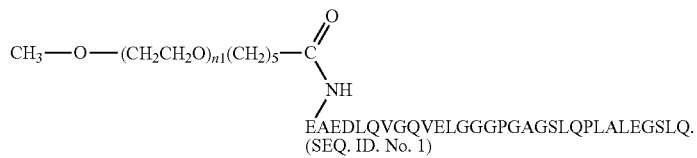

In another embodiment, the present invention includes a PEGylated C-peptide wherein the PEGylated C-peptide has the structure:

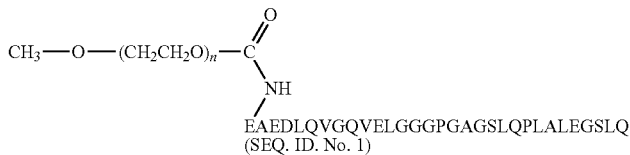

EAEDLQVGQVELGGGPGAGSLQPLALEGSLQ
(SEQ. ID. No. 1)

wherein n is about 400 to about 1000.

In another aspect, the PEGylated C-peptide comprises a branched chain PEG of general formula (II):

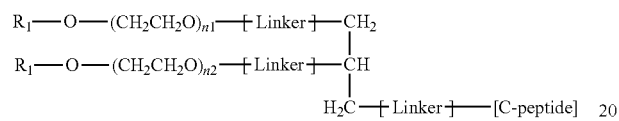

wherein:
$R_1$=alkyl;
$n_1$ is 20 to 800;
$n_2$ is 20 to 800; and
wherein each linker is independently defined as below, and, wherein the linker connecting to C-peptide is attached to the N-terminal amino group of C-peptide.

In another embodiment, the present invention includes a PEGylated C-peptide wherein the PEGylated C-peptide has the structure of general formula (IIA):

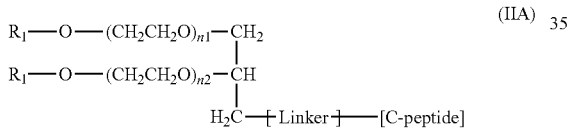

wherein:
$R_1$=alkyl;
$n_1$ is 20 to 800;
$n_2$ is 20 to 800;
the linker is selected from; —X—, —CO—, —$(CH_2)_{m2}$—, —$(CH_2)_{m1}$—CO—, —CO—$(CH_2)_{n1}$—, —CO—X—CO—, —$(CH_2)_{m1}$—X—$(CH_2)_{m1}$—, —$(CH_2)_{m1}$—CO—$(CH_2)_{n1}$—, —X—CO—X—, —X—$(CH_2)_{m1}$—X—, —CO—$(CH_2)_{m1}$—CO—, —X—CO—$(CH_2)_{m1}$—, —$(CH_2)_{m1}$—CO—X—, —X—$(CH_2)_{m1}$—CO—X—, —X—CO—$(CH_2)_{m1}$—X—, —X—CO—$(CH_2)_{m1}$—CO—X—$(CH_2)_{m1}$—X—CO—, —X—$(CH_2)_{m1}$—X—CO—$(CH_2)_{m2}$—, —X—$(CH_2)_{m1}$—CO—X—$(CH_2)_{m2}$—, —X—$(CH_2)_{m1}$—X—CO—$(CH_2)_{m2}$—X—, —X—$(CH_2)_{m1}$—X—CO—$(CH_2)_{m2}$—CO—, —X—$(CH_2)_{m1}$—CO—X—$(CH_2)_{m2}$—X—, and —X—$(CH_2)_{m1}$—CO—X—$(CH_2)_{m2}$—CO—;
wherein:
each X is independently selected from —O—, —S—, or —NH— or is missing;
each $m_1$ is independently 0 to 5; and
each $m_2$ is independently 1 to 5;
and wherein the linker is attached to the N-terminal amino group of C-peptide.

In another aspect of any of these branched chain PEGylated C-peptides, the PEGylated C-peptide comprises a linker connecting the PEG moiety to C-peptide selected from:

—$X_1$—$(CH_2)_{m4}$—CO—;
—$X_1$—CO—;
—$X_1$—CO—$(CH_2)_{m4}$—CO—
—$X_1$—CO—$X_2$—$(CH_2)_{m3}$—CO—; and
—$X_1$—$(CH_2)_{m2}$—$X_2$—CO—$(CH_2)_{m4}$—CO—;
wherein:
$X_1$ is —O—, or missing;
$X_2$ is —NH—;
$m_2$ is 1 to 5;
$m_3$ is 2; and
$m_4$ is 1 to 5.

In another aspect of any of these branched chain PEGylated C-peptides, the PEGylated C-peptide comprises a linker connecting the PEG moiety to C-peptide selected from:

—$X_1$—CO—$X_2$—$(CH_2)_{m5}$—$X_1$—$(CH_2$—$CH_2$—O$)_{n3}$—X—,

—$X_1$—CO—$X_2$—$(CH_2)_{m5}$—$X_1$—$(CH_2$—$CH_2$—O$)_{n3}$—$(CH_2)_{m5}$—CO—,

—$X_1$—CO—$X_2$—$(CH_2)_{m5}$—$X_1$—$(CH_2$—$CH_2$—O$)_{n3}$—CO—, and

—$X_1$—CO—$X_2$—$(CH_2)_{m5}$—$X_1$—$(CH_2$—$CH_2$—O$)_{n3}$—CO—$(CH_2)_{m5}$—CO—;
wherein:
X is independently selected from —O—, —S—, or —NH— or is missing;
$X_1$ is —O—, or missing;
$X_2$ is —NH—;
each $m_5$ is independently selected from 1 to 5; and
each $n_3$ is independently selected from 1 to 400.

In another aspect of any of these branched chain PEGylated C-peptides, the PEGylated C-peptide comprises a linker connecting the PEG moiety to C-peptide selected from;

—$X_1$—CO—$X_2$—$(CH_2)_{m5}$—$X_1$—$(CH_2$—$CH_2$—O$)_{n3}$—$(CH_2)_{m6}$—CO—,

—$X_1$—CO—$X_2$—$(CH_2)_{m5}$—$X_1$—$(CH_2$—$CH_2$—O$)_{n3}$—CO—, and

—$X_1$—CO—$X_2$—$(CH_2)_{m5}$—$X_1$—$(CH_2$—$CH_2$—O$)_{n3}$—CO—$(CH_2)_{m7}$—CO—;
wherein:
$X_1$ is —O—, or is missing;
$X_2$ is —NH—;
$m_5$ is 3;
$m_6$ is independently 2 or 5;
$m_7$ is 3; and
$n_3$ is 1 to 400.

In another embodiment, the present invention includes a PEGylated C-peptide wherein the PEGylated C-peptide has the structure:

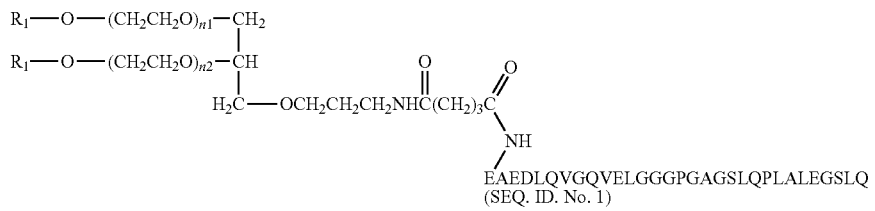

wherein:
$R_1$=alkyl;
$n_1$ is 200 to 800; and
$n_2$ is 200 to 800.

In another embodiment, the present invention includes a PEGylated C-peptide wherein the PEGylated C-peptide has the structure:

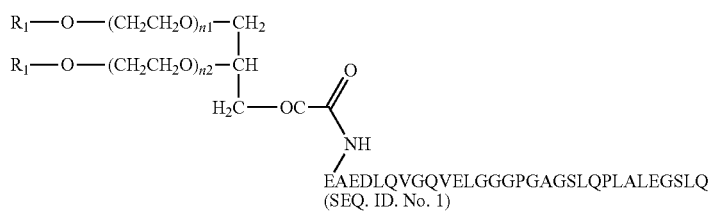

wherein:
$R_1$=alkyl;
$n_1$ is 200 to 800; and
$n_2$ is 200 to 800.

In another embodiment, the present invention includes a PEGylated C-peptide wherein the PEGylated C-peptide has the structure:

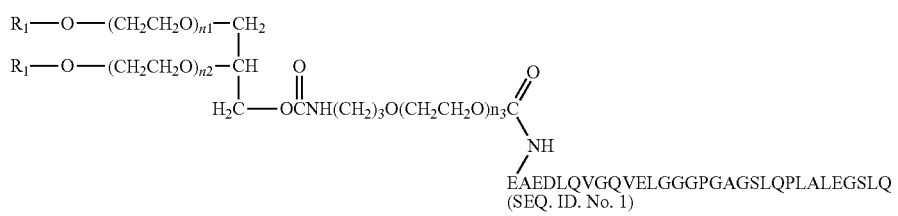

wherein:
$R_1$=alkyl;
$n_1$ is 200 to 800;
$n_2$ is 200 to 800; and
$n_3$ is 1 to 400.

In another embodiment, the present invention includes a PEGylated C-peptide wherein the PEGylated C-peptide has the structure:

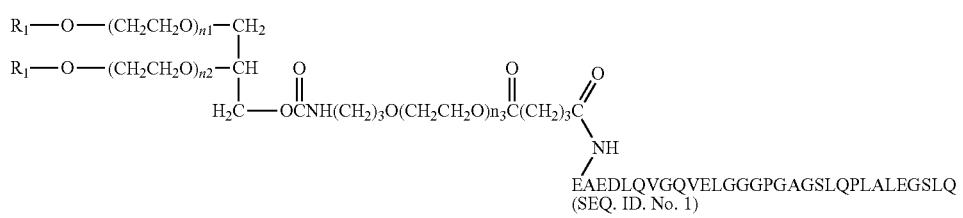

wherein:
 $R_1$=alkyl;
 $n_1$ is 200 to 800;
 $n_2$ is 200 to 800; and
 $n_3$ is 1 to 400.

In another embodiment, the present invention includes a PEGylated C-peptide wherein the PEGylated C-peptide has the structure:

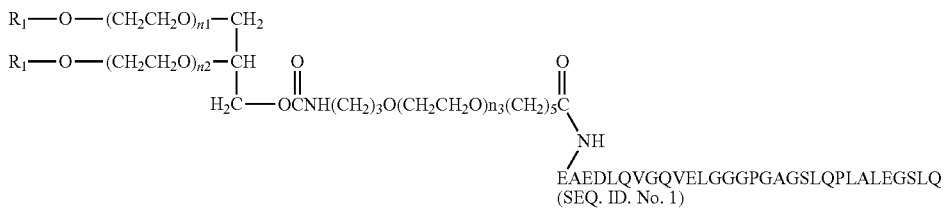
EAEDLQVGQVELGGGPGAGSLQPLALEGSLQ
(SEQ. ID. No. 1)

wherein:
 $R_1$=alkyl;
 $n_1$ is 200 to 800;
 $n_2$ is 200 to 800; and
 $n_3$ is 1 to 400.

In another aspect, the PEGylated C-peptide comprises a branched chain PEG of general formula (III):

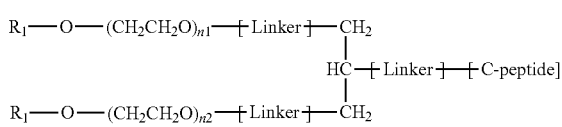 (III)

wherein:
 $R_1$=alkyl;
 $n_1$ is 20 to 800;
 $n_2$ is 20 to 800; and
wherein each linker is independently defined as below, and wherein the linker connecting to C-peptide is attached to the N-terminal amino group of C-peptide.

In one embodiment of the PEGylated C-peptides of formula (III), the PEGylated C-peptide has the structure (III A):

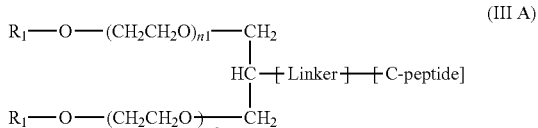 (III A)

wherein:
 $R_1$=alkyl;
 $n_1$ is 20 to 800;
 $n_2$ is 20 to 800; and wherein the linker is defined as below, and is attached to the N-terminal amino group of C-peptide.

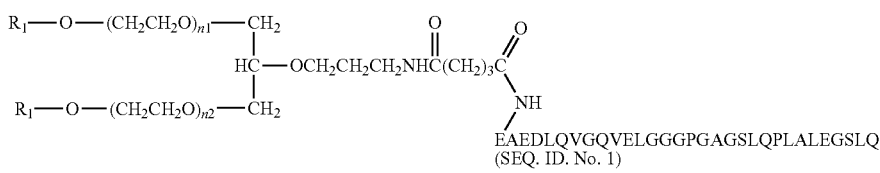
EAEDLQVGQVELGGGPGAGSLQPLALEGSLQ
(SEQ. ID. No. 1)

In another embodiment, the present invention includes a PEGylated C-peptide wherein the PEGylated C-peptide has the structure:

EAEDLQVGQVELGGGPGAGSLQPLALEGSLQ
(SEQ. ID. No. 1)

wherein
 $R_1$=alkyl;
 $n_1$ is 200 to 800; and
 $n_2$ is 200 to 800;

In another aspect, the PEGylated C-peptide comprises a branched chain PEG of general formula (IV):

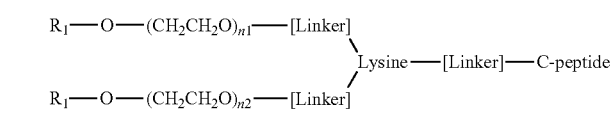 (IV)

wherein:
 $R_1$=alkyl;
 $n_1$ is 20 to 800; and
 $n_2$ is 20 to 800;
wherein each linker is independently defined as below;
wherein the linker connecting the lysine residue to C-peptide is attached to the N-terminal amino group of C-peptide and the C-terminal carboxylate group of the lysine residue, and
wherein the linkers connecting the lysine moiety to the PEG moieties are linked through the amino groups of the lysine molecule.

In another embodiment, the present invention includes a PEGylated C-peptide wherein the PEGylated C-peptide has the structure:

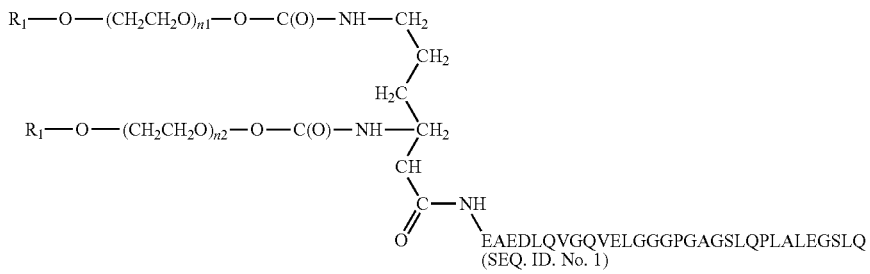

wherein:
R₁=alkyl;
n₁ is 200 to 800; and
n₂ is 200 to 800.

In certain aspects of any of the claimed PEGylated C-peptides, the PEGylated C-peptide has a plasma or sera pharmacokinetic AUC profile at least about 5-fold greater than unmodified C-peptide when subcutaneously administered to dogs.

In certain aspects of any of the claimed PEGylated C-peptides, the PEGylated C-peptide has a plasma or sera pharmacokinetic AUC profile at least about 6-fold greater than unmodified C-peptide when subcutaneously administered to dogs.

In certain aspects of any of the claimed PEGylated C-peptides, the PEGylated C-peptide has a plasma or sera pharmacokinetic AUC profile at least about 7-fold greater than unmodified C-peptide when subcutaneously administered to dogs.

In certain aspects of any of the claimed PEGylated C-peptides, the PEGylated C-peptide has a plasma or sera pharmacokinetic AUC profile at least about 8-fold greater than unmodified C-peptide when subcutaneously administered to dogs.

In certain aspects of any of the claimed PEGylated C-peptides, the PEGylated C-peptide has a plasma or sera pharmacokinetic AUC profile at least about 10-fold greater than unmodified C-peptide when subcutaneously administered to dogs.

In certain aspects of any of the claimed PEGylated C-peptides, the PEGylated C-peptide has a plasma or sera pharmacokinetic AUC profile at least about 15-fold greater than unmodified C-peptide when subcutaneously administered to dogs.

In certain aspects of any of the claimed PEGylated C-peptides, the PEGylated C-peptide has a plasma or sera pharmacokinetic AUC profile at least about 20-fold greater than unmodified C-peptide when subcutaneously administered to dogs.

In certain aspects of any of the claimed PEGylated C-peptides, the PEGylated C-peptide has a plasma or sera pharmacokinetic AUC profile at least about 25-fold greater than unmodified C-peptide when subcutaneously administered to dogs.

In certain aspects of any of the claimed PEGylated C-peptides, the PEGylated C-peptide has a plasma or sera pharmacokinetic AUC profile at least about 50-fold greater than unmodified C-peptide when subcutaneously administered to dogs.

In certain aspects of any of the claimed PEGylated C-peptides, the PEGylated C-peptide has a plasma or sera pharmacokinetic AUC profile at least about 75-fold greater than unmodified C-peptide when subcutaneously administered to dogs.

In certain aspects of any of the claimed PEGylated C-peptides, the PEGylated C-peptide has a plasma or sera pharmacokinetic AUC profile at least about 100-fold greater than unmodified C-peptide when subcutaneously administered to dogs.

In certain aspects of any of the claimed PEGylated C-peptides, the PEGylated C-peptide has an equi-potent biological activity with the unmodified C-peptide. In certain aspects of any of the claimed PEGylated C-peptides, the PEGylated C-peptide retains at least about 95% of the biological activity of the unmodified C-peptide. In certain aspects of any of the claimed PEGylated C-peptides, the PEGylated C-peptide retains at least about 90% of the biological activity of the unmodified C-peptide. In certain aspects of any of the claimed PEGylated C-peptides, the PEGylated C-peptide retains at least about 80% of the biological activity of the unmodified C-peptide. In another aspect of any of the claimed PEGylated C-peptides, the PEGylated C-peptide retains at least about 70% of the biological activity of the unmodified C-peptide. In another aspect of any of the claimed PEGylated C-peptides, the PEGylated C-peptide retains at least about 60% of the biological activity of the unmodified C-peptide. In another aspect of any of the claimed PEGylated C-peptides, the PEGylated C-peptide retains at least about 50% of the biological activity of the unmodified C-peptide. In another aspect of any of the claimed PEGylated C-peptides, the PEGylated C-peptide retains at least about 40% of the biological activity of the unmodified C-peptide. In another aspect of any of the claimed PEGylated C-peptides, the PEGylated C-peptide retains at least about 30% of the biological activity of the unmodified C-peptide. In another aspect of any of the claimed PEGylated C-peptides, the PEGylated C-peptide retains at least about 20% of the biological activity of the unmodified C-peptide. In another aspect of any of the claimed PEGylated C-peptides, the PEGylated C-peptide retains at least about 10% of the biological activity of the unmodified C-peptide. In another aspect of any of the claimed PEGylated C-peptides, the PEGylated C-peptide retains at least about 5% of the biological activity of the unmodified C-peptide.

In another embodiment, the present invention includes a dosing regimen which maintains an average steady-state concentration of PEGylated C-peptide in the patient's plasma of between about 0.2 nM and about 6 nM when using a dosing interval of 3 days or longer, comprising administering to the patient a therapeutic dose of PEGylated C-peptide of any of the claimed PEGylated C-peptides.

In another embodiment, the present invention includes a dosing regimen which maintains an average steady-state concentration of PEGylated C-peptide in the patient's plasma of between about 0.4 nM and about 6 nM when using a dosing interval of 3 days or longer, comprising administering to the patient a therapeutic dose of PEGylated C-peptide of any of the claimed PEGylated C-peptides.

In another embodiment, the present invention includes a dosing regimen which maintains an average steady-state concentration of PEGylated C-peptide in the patient's plasma of between about 0.6 nM and about 8 nM when using a dosing interval of 3 days or longer, comprising administering to the patient a therapeutic dose of PEGylated C-peptide of any of the claimed PEGylated C-peptides.

In another embodiment, the present invention includes a dosing regimen which maintains an average steady-state concentration of PEGylated C-peptide in the patient's plasma of between about 0.8 nM and about 10 nM when using a dosing interval of 3 days or longer, comprising administering to the patient a therapeutic dose of PEGylated C-peptide of any of the claimed PEGylated C-peptides.

In another embodiment, the present invention includes a method for maintaining C-peptide levels above the minimum effective therapeutic level in a patient in need thereof, comprising administering to the patient a therapeutic dose of any of the claimed PEGylated C-peptides.

In another aspect of any of the claimed PEGylated C-peptides, the PEGylated C-peptide is substantially free of adverse side effects when subcutaneously administered to a mammal at an effective therapeutic dose.

In another embodiment, the present invention includes a method for treating one or more long-term complications of diabetes in a patient in need thereof, comprising administering to the patient a therapeutic dose of any of the claimed PEGylated C-peptides.

In another embodiment, the present invention includes a method for treating a patient with diabetes comprising administering to the patient a therapeutic dose of PEGylated C-peptide of any of the claimed PEGylated C-peptides in combination with insulin.

In one aspect of any of these methods, the PEGylated C-peptide is administered with a dosing interval of about 3 days or longer. In one aspect of any of these methods, the PEGylated C-peptide is administered with a dosing interval of about 4 days or longer. In one aspect of any of these methods, the PEGylated C-peptide is administered with a dosing interval of about 5 days or longer. In one aspect of any of these methods, the PEGylated C-peptide is administered with a dosing interval of about 6 days or longer. In one aspect of any of these methods, the PEGylated C-peptide is administered with a dosing interval of about 7 days or longer.

In certain embodiments, treatment results in an improvement of at least 10% in nerve conduction velocity compared to nerve conduction velocity prior to starting PEGylated C-peptide therapy.

In another aspect of any of these methods, the plasma concentration of PEGylated C-peptide is maintained above about 0.1 nM. In another aspect of any of these methods, the plasma concentration of PEGylated C-peptide is maintained above about 0.2 nM. In another aspect of any of these methods, the plasma concentration of PEGylated C-peptide is maintained above about 0.3 nM. In another aspect of any of these methods, the plasma concentration of PEGylated C-peptide is maintained above about 0.4 nM.

In another aspect of any of these methods, the therapeutic dose of PEGylated C-peptide is administered subcutaneously. In another aspect of any of these methods, the therapeutic dose of PEGylated C-peptide is administered orally.

In another embodiment, the present invention includes the use of any of the claimed PEGylated C-peptides as a C-peptide replacement therapy in a patient in need thereof.

In another embodiment, the present invention includes the use of any of the claimed PEGylated C-peptides for treating one or more long-term complications of diabetes in a patient in need thereof. In certain embodiments, the long-term complications of diabetes are selected from the group consisting of retinopathy, peripheral neuropathy, autonomic neuropathy, and nephropathy. In certain embodiments, the long-term complication of diabetes is peripheral neuropathy. In certain embodiments, the peripheral neuropathy is established peripheral neuropathy. In certain embodiments, treatment results in an improvement of at least 10% in nerve conduction velocity compared to nerve conduction velocity prior to starting PEGylated C-peptide therapy.

In another embodiment, the present invention includes a pharmaceutical composition comprising any of the claimed PEGylated C-peptides and a pharmaceutically acceptable carrier or excipient. In certain embodiments, the pharmaceutically acceptable carrier or excipient is sorbitol. In certain embodiments, the sorbitol is present at a concentration of about 2% to about 8% wt/wt. In certain embodiments, the sorbitol is present at a concentration of about 4.7%. In certain embodiments, the pharmaceutical composition is buffered to a pH within the range of about pH 5.5 to about pH 6.5. In certain embodiments, the pharmaceutical composition is buffered to a pH of about 6.0. In certain embodiments, the pharmaceutical composition is buffered with a phosphate buffer at a concentration of about 5 mM to about 25 mM. In certain embodiments, the pharmaceutical composition is buffered with a phosphate buffer at a concentration of about 10 mM. In one aspect of any of these embodiments, the pharmaceutical composition is characterized by improved stability of any of the claimed PEGylated C-peptides compared to a pharmaceutical composition comprising the same PEGylated C-peptide and 0.9% saline at pH 7.0, wherein the stability is determined after incubation for a predetermined time at 40° C. In different embodiments, the pre-determined time is about one week, about 2 weeks, about three weeks, about four weeks, or about five weeks, or about six weeks.

In another embodiment, the present invention includes a pharmaceutical composition comprising any of the claimed PEGylated C-peptides and insulin.

Certain embodiments include the use of any of the disclosed PEGylated C-peptides to reduce the risk of hypoglycemia in a human patient with insulin dependent diabetes, in a regimen which additionally comprises the administration of insulin, comprising; a) administering insulin to the patient; b) administering a therapeutic dose of the PEGylated C-peptide in a different site as that used for the patient's insulin administration; c) adjusting the dosage amount, type, or frequency of insulin administered based on the patient's altered insulin requirements resulting from the therapeutic dose of the PEGylated C-peptide.

In some embodiments, the patient has at least one long term complications of diabetes.

Certain embodiments include a method for treating an insulin-dependent human patient, comprising the steps of; a) administering insulin to the patient, wherein the patient has neuropathy; b) administering subcutaneously to the patient a therapeutic dose of any of the disclosed PEGylated C-peptides in a different site as that used for the patient's insulin administration; c) adjusting the dosage amount, type, or frequency of insulin administered based on monitoring the patient's altered insulin requirements resulting from the therapeutic dose of PEGylated C-peptide, wherein the adjusted dose of insulin reduces the risk, incidence, or severity of hypoglycemia, wherein the adjusted dose of insulin is at least 10% less than the patient's insulin dose prior to starting PEGylated C-peptide treatment.

Certain embodiments include a method of reducing insulin usage in an insulin-dependent human patient, comprising the steps of; a) administering insulin to the patient; b) administering subcutaneously to the patient a therapeutic dose any of the disclosed PEGylated C-peptides in a different site as that used for the patient's insulin administration; c) adjusting the dosage amount, type, or frequency of insulin administered based on monitoring the patient's altered insulin requirements resulting from the therapeutic dose of PEGylated C-peptide, wherein the adjusted dose of insulin does not induce hypoglycemia, wherein the adjusted dose of insulin is at least 10% less than the patient's insulin dose prior to starting the PEGylated C-peptide treatment.

BRIEF DESCRIPTION OF THE DRAWINGS

A better understanding of the features and advantages of the present invention can be obtained by reference to the following detailed description that sets forth illustrative embodiments, in which the principles of the invention are utilized, and the accompanying drawings of which:

FIG. 5 shows the plasma concentration-time profiles of unmodified C-peptide in dogs following a single subcutaneous dose. FIG. 5A shows the profile on a time scale of one day, FIG. 5B shows the profile on a time scale of 12 days. The term "AQ-CP" refers to aqueous C-peptide.

FIG. 8 shows the plasma concentration-time profiles of C-peptide in dogs following single subcutaneous doses of PEGylated C-peptide. FIG. 8A shows data presented using a linear scale. FIG. 8B shows data presented in semi-logarithmic form.

FIG. 9 shows $C_{max}$ and $AUC_{(0-t)}$ of C-peptide in dogs following single subcutaneous doses of PEGylated C-peptide. FIG. 9A shows $C_{max}$ and FIG. 9B shows $AUC_{(0-t)}$. The term "$C_{max}$" refers to the maximum serum or plasma concentration of drug which occurs during the period of release which is monitored. The term $AUC_{(0-t)}$ refers to the area under the plasma concentration-time curve from time zero to the time of the last quantifiable concentration.

FIG. 10 shows Mean (±SD) C-peptide plasma concentration-time profile in Sprague Dawley rats following single-dose subcutaneous administration of PEGylated C-peptide. Panel A Linear scale; Panel B Semi-log scale. The term "CBX129801" refers to the PEGylated C-peptide of Example 12.

FIG. 11 shows mean (±SD) C-peptide plasma concentration-time profile in Cynomolgus monkeys following single-dose subcutaneous administration of PEGylated C-peptide. Panel A Linear scale; Panel B Semi-log scale. The term "CBX129801" refers to the PEGylated C-peptide of Example 12.

In FIG. 16, panel A shows the baseline NCV measurements, and panel B shows caudal NCV after a 4-week period (from Baseline) of administration of either vehicle alone or the PEGylated C-peptide at either 1.0 or 3.0 mg/kg/week. FIG. 16, panel C shows caudal NCV after an 8-week period (from Baseline) of administration of either vehicle alone or the PEGylated C-peptide at either 1.0 or 3.0 mg/kg/week. The term "CBX129801" refers to the PEGylated C-peptide of Example 12. The abbreviation "n" in FIG. 16 refers to the number of animals in the indicated treatment group.

In FIG. 17, panel A shows the baseline measurements, and panel B shows digital NCV after a 4-week period (from Baseline) of administration of either vehicle alone or the PEGylated C-peptide at either 1.0 or 3.0 mg/kg/week. FIG. 17, panel C shows digital NCV after an 8-week period (from Baseline) of administration of either vehicle alone or the PEGylated C-peptide at either 1.0 or 3.0 mg/kg/week. The term "CBX129801" refers to the PEGylated C-peptide of Example 12. The abbreviation "n" in FIG. 17 refers to the number of animals in the indicated treatment group.

DETAILED DESCRIPTION OF THE INVENTION

Definitions

Figure 1:
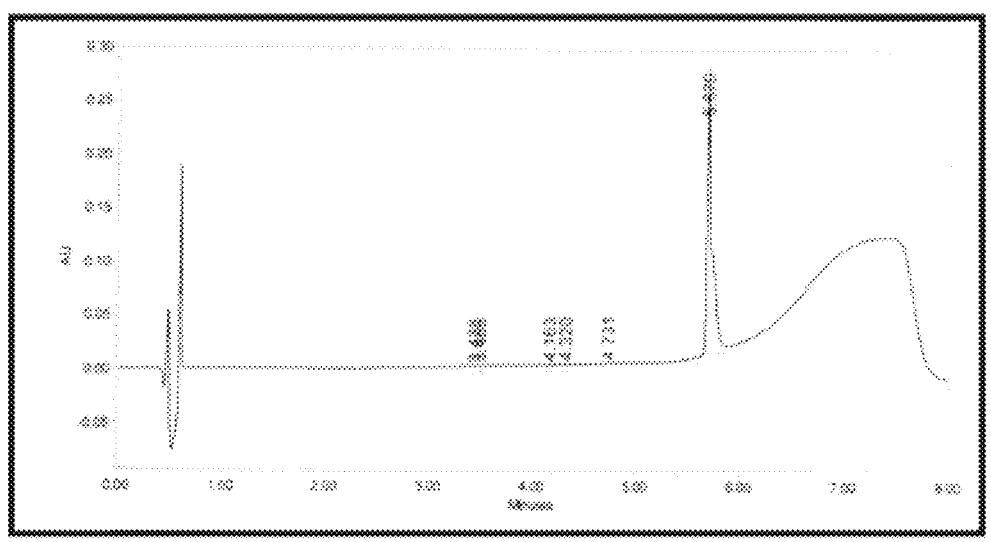
FIG. 1 shows a reverse phase chromatogram of a 40 kDa branched chain PEGylated C-peptide of the invention wherein the term "AU" refers to absorbance units.

The term "active" or "activated" when used in conjunction with a particular functional group refers to a reactive functional group that reacts readily with an electrophile or a nucleophile on another molecule. This is in contrast to those groups that require strong catalysts or highly impractical reaction conditions in order to react (i.e., a "non-reactive" or "inert" group). As used herein, the term "functional group" or any synonym thereof is meant to encompass protected forms thereof as well as unprotected forms.

The term "alkoxy" refers to an —O—R group, wherein R is alkyl or substituted alkyl, preferably $C_{1-6}$ alkoxy (e.g., methoxy, ethoxy, propyloxy, and so forth).

The term "alkyl" refers to a hydrocarbon, typically ranging from about 1 to 12 atoms in length. Hydrocarbons may be branched or linear and are preferably, but not necessarily saturated. Exemplary alkyl groups include methyl, ethyl, propyl, butyl, pentyl, 2-methylbutyl, 2-ethylpropyl, etc. As used herein "alkyl" includes cycloalkyl as well as cycloalkylene alkyls. The term "lower alkyl" refers to an alkyl group containing from 1 to 6 carbon atoms, and may be straight chain or branched.

The term "$C_{max}$" as used herein is the maximum serum or plasma concentration of drug which occurs during the period of release which is monitored.

The term "$C_{min}$" as used herein is the minimum serum or plasma concentration of drug which occurs during the period of release during the treatment period.

The term "$C_{ave}$" as used herein is the average serum or plasma concentration of drug derived by dividing the area under the curve (AUC) of the release profile by the duration of the release.

The term "$C_{ss-ave}$" as used herein is the average steady-state concentration of drug obtained during a multiple dosing regimen after dosing for at least five elimination half-lives. It will be appreciated that drug concentrations are fluctuating within dosing intervals even once an average steady-state concentration of drug has been obtained.

The term "$t_{max}$" as used herein is the time post-dose at which $C_{max}$ is observed.

The term "AUC" as used herein means "area under curve" for the serum or plasma concentration-time curve, as calculated by the trapezoidal rule over the complete sample collection interval.

The term "bioavailability" refers to the amount of drug that reaches the circulation system expressed in percent of that administered. The amount of bioavailable material can be defined as the calculated AUC for the release profile of the drug during the time period starting at post-administration and ending at a predetermined time point. As is understood in the art, a release profile is generated by graphing the serum levels of a biologically active agent in a subject (Y-axis) at predetermined time points (X-axis). Bioavailability is often referred to in terms of % bioavailability, which is the bioavailability achieved for a drug (such as C-peptide) following administration of a sustained release composition of that drug divided by the bioavailability achieved for the drug following intravenous administration of the same equivalent dose of the drug, multiplied by 100.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz G E and R H Schirmer, *Principles of Protein Structure*, Springer-Verlag (1979)). According to such analyses, groups of amino acids can be defined where amino acids within a group exchange preferentially with each other, and therefore resemble each other most in their impact on the overall protein structure (Schulz G E and R H Schirmer, *Principles of Protein Structure*, Springer-Verlag (1979)).

Examples of amino acid groups defined in this manner include: a "charged/polar group," consisting of Glu, Asp, Asn, Gln, Lys, Arg, and His; an "aromatic or cyclic group," consisting of Pro, Phe, Tyr, and Trp; and an "aliphatic group," consisting of Gly, Ala, Val, Leu, Ile, Met, Ser, Thr, and Cys.

Within each group, subgroups can also be identified, e.g., the group of charged/polar amino acids can be sub-divided into the subgroups consisting of the "positively-charged subgroup," consisting of Lys, Arg, and His; the "negatively-charged subgroup," consisting of Glu and Asp, and the "polar subgroup" consisting of Asn and Gln. The aromatic or cyclic group can be sub-divided into the subgroups consisting of the "nitrogen ring subgroup," consisting of Pro, His, and Trp; and the "phenyl subgroup" consisting of Phe and Tyr. The aliphatic group can be sub-divided into the subgroups consisting of the "large aliphatic non-polar subgroup," consisting of Val, Leu, and Ile; the "aliphatic slightly-polar subgroup," consisting of Met, Ser, Thr, and Cys; and the "small-residue subgroup," consisting of Gly and Ala.

Examples of conservative mutations include amino acid substitutions of amino acids within the subgroups above, e.g., Lys for Arg and vice versa such that a positive charge can be maintained; Glu for Asp and vice versa such that a negative charge can be maintained; Ser for Thr such that a free —OH can be maintained; and Gln for Asn such that a free —$NH_2$ can be maintained. "Semi-conservative mutations" include amino acid substitutions of amino acids with the same groups listed above, which do not share the same subgroup. For example, the mutation of Asp for Asn, or Asn for Lys, all involve amino acids within the same group, but different subgroups. "Non-conservative mutations" involve amino acid substitutions between different groups, e.g., Lys for Leu, Phe for Ser.

The terms "Dalton", "Da", or "D" refers to an arbitrary unit of mass, being $\frac{1}{12}$ the mass of the nuclide of carbon-12, equivalent to $1.657 \times 10^{-24}$ g. The term "kDa" is for kilodalton (i.e., 1000 Daltons).

The terms "diabetes", "diabetes mellitus", or "diabetic condition", unless specifically designated otherwise, encompass all forms of diabetes. The term "type 1 diabetic" or "type 1 diabetes" refers to a patient with a fasting plasma glucose concentration of greater than about 7.0 mmoL/L and a fasting C-peptide level of about, or less than about 0.2 nmoL/L. The term "type 1.5 diabetic" or "type 1.5 diabetes" refers to a patient with a fasting plasma glucose concentration of greater than about 7.0 mmoL/L and a fasting C-peptide level of about, or less than about 0.4 nmoL/L. The term "type 2 diabetic" or "type 2 diabetes" generally refers to a patient with a fasting plasma glucose concentration of greater than about 7.0 mmoL/L and fasting C-peptide level that is within or higher than the normal physiological range of C-peptide levels (about 0.47 to 2.5 nmoL/L). It will be appreciated that a patient initially diagnosed as a type 2 diabetic may subsequently develop insulin-dependent diabetes, and may remain diagnosed as a type 2 patient, even though their C-peptide levels drop to those of a type 1.5 or type 1 diabetic patient (<0.2 nmol/L).

The terms "insulin-dependent patient" or "insulin-dependent diabetes" encompass all forms of diabetics/diabetes who/that require insulin administration to adequately maintain normal glucose levels unless specified otherwise.

Diabetes is frequently diagnosed by measuring fasting blood glucose, insulin, or glycated hemoglobin levels (which are typically referred to as hemoglobin A1c, $Hb_{1c}$, $Hb_{A1c}$, or A1C). Normal adult glucose levels are 60-126 mg/dL. Normal insulin levels are 30-60 pmoL/L. Normal HbA1c levels are generally less than 6%. The World Health Organization defines the diagnostic value of fasting plasma glucose concentration to 7.0 mmoL/L (126 mg/dL) and above for diabetes mellitus (whole blood 6.1 mmoL/L or 110 mg/dL), or 2-hour glucose level greater than or equal to 11.1 mmoL/L (greater than or equal to 200 mg/dL). Other values suggestive of or indicating high risk for diabetes mellitus include elevated arterial pressure greater than or equal to 140/90 mm Hg; elevated plasma triglycerides (greater than or equal to 1.7 mmoL/L [150 mg/dL]) and/or low HDL-cholesterol (less than 0.9 mmoL/L [35 mg/dL] for men; and less than 1.0 mmoL/L [39 mg/dL] for women); central obesity (BMI exceeding 30 kg/m$^2$); microalbuminuria, where the urinary albumin excretion rate is greater than or equal to 20 μg/min or the albumin creatinine ratio is greater than or equal to 30 mg/g.

The term "delivery agent" refers to carrier compounds or carrier molecules that are effective in the oral delivery of therapeutic agents, and may be used interchangeably with "carrier".

The term "homology" describes a mathematically-based comparison of sequence similarities which is used to identify genes or proteins with similar functions or motifs. The nucleic acid and protein sequences of the present invention can be used as a "query sequence" to perform a search against public databases to, e.g., identify other family members, related sequences, or homologs. Such searches can be performed using the NBLAST and XBLAST programs (version 2.0) of Altschul et al.: *J. Mol. Biol.* 215: 403-410, (1990). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al.: *Nucleic Acids Res.* 25(17): 3389-3402, (1997). When utilizing BLAST and Gapped BLAST programs, the default parameters of the respective programs (e.g., XBLAST and BLAST) can be used (see <www.ncbi.nlm.nih.gov>).

The term "homologous" refers to the relationship between two proteins that possess a "common evolutionary origin", including proteins from superfamilies (e.g., the immunoglobulin superfamily) in the same species of animal, as well as homologous proteins from different species of animal (e.g., myosin light chain polypeptide; see Reeck et al.: *Cell* 50: 667, (1987)). Such proteins (and their encoding nucleic acids) have sequence homology, as reflected by their sequence similarity, whether in terms of percent identity or by the presence of specific residues or motifs and conserved positions. In specific embodiments, two nucleic acid sequences are "substantially homologous" or "substantially similar" when at least about 85%, and more preferably at least about 90% or at least about 95% of the nucleotides match over a defined length of the nucleic acid sequences, as determined by a sequence comparison algorithm known such as BLAST, FASTA, DNA Strider, CLUSTAL, etc. An example of such a sequence is an allelic or species variant of the specific genes of the present invention. Sequences that are substantially homologous may also be identified by hybridization, e.g., in a Southern hybridization experiment under, e.g., stringent conditions as defined for that particular system.

Similarly, in particular embodiments of the invention, two amino acid sequences are "substantially homologous" or "substantially similar" when greater than 80% of the amino acid residues are identical, or when greater than about 90% of the amino acid residues are similar (i.e., are functionally identical). Preferably the similar or homologous polypeptide sequences are identified by alignment using, e.g., the GCG (Genetics Computer Group, version 7, Madison, Wis.) pileup program, or using any of the programs and algorithms described above. The program may use the local homology algorithm of Smith and Waterman with the default values: gap creation penalty=−(1+⅓k), k being the gap extension number, average match=1, average mismatch=−0.333.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in *Computational Molecular Biology*, Lesk A M, Ed., Oxford University Press, New York, (1988); *Biocomputing: Informatics and Genome Projects*, Smith D W, Ed., Academic Press, New York, (1993); *Computer Analysis of Sequence Data, Part I*, Griffin A M and Griffin H G, Eds., Humana Press, New Jersey, (1994); *Sequence Analysis in Molecular Biology*, von Heinje G, Academic Press, (1987); and *Sequence Analysis Primer*, Gribskov M and Devereux J, Eds., M Stockton Press, New York, (1991); and Carillo H and Lipman D, *SIAM J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux J et al.: *Nucleic Acids Res.* 12(1): 387, (1984)), BLASTP, BLASTN, and FASTA (Altschul S F et al.: *J. Molec. Biol.* 215: 403-410, (1990) and Altschul S F et al.: *Nucleic Acids Res.* 25: 3389-3402, (1997)). The BLAST X program is publicly available from NCBI and other sources (BLAST Manual, Altschul S F et al., NCBI NLM NIH Bethesda, Md. 20894; Altschul S F et al., *J. Mol. Biol.* 215: 403-410, (1990)). The well-known Smith Waterman algorithm (Smith T F, Waterman M S: *J. Mol. Biol.* 147(1): 195-197, (1981)) can also be used to determine similarity between sequences.

The term "insulin" includes all forms of insulin including, without limitation, rapid-acting forms, such as Insulin Lispro rDNA origin: HUMALOG® (1.5 mL, 10 mL, Eli Lilly and Company, Indianapolis, Ind.), Insulin Injection (Regular Insulin) from beef and pork (regular ILETIN® I, Eli Lilly), human: rDNA: HUMULIN® R (Eli Lilly), NOVOLIN® R (Novo Nordisk, New York, N.Y.), Semi synthetic: VELOSULIN® Human (Novo Nordisk), rDNA Human, Buffered: VELOSULIN® BR, pork: regular Insulin (Novo Nordisk), purified pork: Pork Regular ILETIN® II (Eli Lilly), Regular Purified Pork Insulin (Novo Nordisk), and Regular (Concentrated) ILETIN® II U-500 (500 units/mL, Eli Lilly); intermediate-acting forms such as Insulin Zinc Suspension, beef and pork: LENTE ILETIN® G I (Eli Lilly), Human, rDNA: HUMULIN® L (Eli Lilly), NOVOLIN® L (Novo Nordisk), purified pork: LENTE ILETIN® II (Eli Lilly), Isophane Insulin Suspension (NPH): beef and pork: NPH ILETIN® I (Eli Lilly), Human, rDNA: HUMULIN® N (Eli Lilly), Novolin N (Novo Nordisk), purified pork: Pork NPH Eetin II (Eli Lilly), NPH-N (Novo Nordisk); and long-acting forms such as Insulin zinc suspension, extended (ULTRALENTE®, Eli Lilly), human, rDNA: HUMULIN® U (Eli Lilly).

The terms "measuring" or "measurement" mean assessing the presence, absence, quantity, or amount (which can be an effective amount) of either a given substance within a clinical- or patient-derived sample, including the derivation of qualitative or quantitative concentration levels of such substances, or otherwise evaluating the values or categorization of a patient's clinical parameters.

The term "meal" as used herein means a standard and/or a mixed meal.

The term "mean", when preceding a pharmacokinetic value (e.g., mean $t_{max}$), represents the arithmetic mean value of the pharmacokinetic value unless otherwise specified.

The term "mean baseline level" as used herein means the measurement, calculation, or level of a certain value that is used as a basis for comparison, which is the mean value over a statistically significant number of subjects, e.g., across a single clinical study or a combination of more than one clinical study.

The term "multiple dose" means that the patient has received at least two doses of the drug composition in accordance with the dosing interval for that composition.

The term "neuropathy" in the context of a "patient with neuropathy" or a patient that "has neuropathy", means that the patient meets at least one of the four criteria outlined in the San Antonio Conference on diabetic neuropathy (report and recommendations of the San Antonio Conference on diabetic neuropathy. *Ann. Neurol.* 24 99-104 (1988)), which in brief include 1) clinical signs of polyneuropathy, 2) symptoms of nerve dysfunction, 3) nerve conduction deficits in at least two nerves, or 4) quantitative sensory deficits. The term "established neuropathy" means that the patient meets at least two of the four criteria outlined in the San Antonio Conference on diabetic neuropathy. The term "incipient neuropathy" refers to a patient that exhibits only nerve conduction deficits, and no other symptoms of neuropathy.

The term "normal glucose levels" is used interchangeably with the term "normoglycemic" and "normal" and refers to a fasting venous plasma glucose concentration of less than about 6.1 mmoL/L (110 mg/dL). Sustained glucose levels above normoglycemic are considered a pre-diabetic condition.

As used herein, the term "patient" in the context of the present invention is preferably a mammal. The mammal can be a human, non-human primate, mouse, rat, dog, cat, horse, or cow, but are not limited to these examples. Mammals other than humans can be advantageously used as patients that represent animal models of insulin-dependent diabetes mellitus, or diabetic conditions. A patient can be male or female. A patient can be one who has been previously diagnosed or identified as having insulin-dependent diabetes, or a diabetic condition, and optionally has already undergone, or is undergoing, a therapeutic intervention for the diabetes. A patient can also be one who is suffering from a long-term complication of diabetes. Preferably the patient is human.

The terms "PEG", "polyethylene glycol", or "poly(ethylene glycol)" as used herein refers to any water soluble poly (ethylene oxide), and includes molecules comprising the structure —$(CH_2CH_2O)_n$— where n is an integer from 2 to about 800. A commonly used PEG is end-capped PEG, wherein one end of the PEG is capped with a relatively inactive group such as an alkoxy while the other end is a hydroxyl group that may be further modified. An often-used capping group is methoxy and the corresponding end-capped PEG is often denoted mPEG. The notion PEG is often used instead of mPEG. Specific PEG forms of the invention are branched, linear, forked PEGs, and the like and the PEG groups are typically polydisperse, possessing a low polydispersity index of less than about 1.05. The PEG moieties of the invention will for a given molecular weight will typically consist of a range of ethylene glycol (or ethyleneoxide) monomers. For example, A PEG moiety of molecular weight 2000 Da will typically consist of 43±10 monomers, the average being around 43 monomers. The term "PEGylated" refers to the covalent attachment of PEG to another molecule, such as C-peptide.

The term "replacement dose" in the context of a replacement therapy for C-peptide refers to a dose of C-peptide or PEGylated C-peptide that maintains C-peptide or PEGylated C-peptide levels in the blood within a desirable range, particularly at a level which is at or above the minimum effective therapeutic level. In certain aspects, the replacement dose maintains the average steady-state concentration C-peptide or PEGylated C-peptide levels above a minimum level of about 0.1 nM between dosing intervals. In certain aspects, the replacement dose maintains the average steady-state concentration C-peptide or PEGylated C-peptide levels above a minimum level of about 0.2 nM between dosing intervals. In certain aspects, the replacement dose maintains the average steady-state concentration C-peptide or PEGylated C-peptide levels above a minimum level of about 0.4 nM between dosing intervals.

The terms "subcutaneous" or "subcutaneously" or "S.C." in reference to a mode of administration of insulin or PEGylated C-peptide, refers to a drug that is administered as a bolus injection, or via an implantable device into the area in, or below the subcutis, the layer of skin directly below the dermis and epidermis, collectively referred to as the cutis. Preferred sites for subcutaneous administration and/or implantation include the outer area of the upper arm, just above and below the waist, except the area right around the navel (a 2-inch circle). The upper area of the buttock, just behind the hipbone. The front of the thigh, midway to the outer side, 4 inches below the top of the thigh to 4 inches above the knee.

The term "single dose" means that the patient has received a single dose of the drug composition or that the repeated single doses have been administered with washout periods in between. Unless specifically designated as "single dose" or at "steady-state" the pharmacokinetic parameters disclosed and claimed herein encompass both single-dose and multiple-dose conditions.

The term "sequence similarity" refers to the degree of identity or correspondence between nucleic acid or amino acid sequences that may or may not share a common evolutionary origin (see Reeck et al., supra). However, in common usage and in the present application, the term "homologous", when modified with an adverb such as "highly", may refer to sequence similarity and may or may not relate to a common evolutionary origin.

By "statistically significant", it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

As defined herein, the terms "sustained release", "extended release", or "depot formulation" refers to the release of a drug such as PEGylated C-peptide from the sustained release composition or sustained release device which occurs over a period which is longer than that period during which the drug would be available following direct I.V. or S.C. administration of a single dose of drug. In one aspect, sustained release will be a release that occurs over a period of at least about one to two weeks, about two to four weeks, about one to two months, about two to three months, or about three to six months. In certain aspects, sustained release will be a release that occurs over a period of about six months to about one year. The continuity of release and level of release can be affected by the type of sustained release device (e.g., programmable pump or osmotically-driven pump) or sustained release composition, and type of PEGylated C-peptides used (e.g., monomer ratios, molecular weight, block composition, and varying combinations of polymers), polypeptide loading, and/or selection of excipients to produce the desired effect, as more fully described herein.

Various sustained release profiles can be provided in accordance with any of the methods of the present invention. "Sustained release profile" means a release profile in which less than 50% of the total release of drug that occurs over the course of implantation/insertion or other method of administering the drug in the body occurs within the first 24 hours of administration. In a preferred embodiment of the present invention, the extended release profile is selected from the group consisting of; a) the 50% release point occurring at a time that is between 48 and 72 hours after implantation/insertion or other method of administration; b) the 50% release point occurring at a time that is between 72 and 96 hours after implantation/insertion or other method of administration; c) the 50% release point occurring at a time that is between 96 and 110 hours after implantation/insertion or other method of administration; d) the 50% release point occurring at a time that is between 1 and 2 weeks after implantation/insertion or other method of administration; e) the 50% release point occurring at a time that is between 2 and 4 weeks after implantation/insertion or other method of administration; f) the 50% release point occurring at a time that is between 4 and 8 weeks after implantation/insertion or other method of administration; g) the 50% release point occurring at a time that is between 8 and 16 weeks after implantation/insertion or other method of administration; h) the 50% release point occurring at a time that is between 16 and 52 weeks (1 year) after implantation/insertion or other method of administration; and i) the 50% release point occurring at a time that is between 52 and 104 weeks after implantation/insertion or other method of administration.

Additionally, use of a sustained release composition can reduce the "degree of fluctuation" ("DFL") of the drugs plasma concentration. DFL is a measurement of how much the plasma levels of a drug vary over the course of a dosing interval ($C_{max}$–$C_{min}$/$C_{min}$). For simple cases, such as I.V. administration, fluctuation is determined by the relationship between the elimination half-life ($T_{1/2}$) and dosing interval. If the dosing interval is equal to the half-life then the trough concentration is exactly half of the peak concentration, and the degree of fluctuation is 100%. Thus a sustained release composition with a reduced DFL (for the same dosing interval) signifies that the difference in peak and trough plasma levels has been reduced. Preferably, the patients receiving a sustained release composition of PEGylated C-peptide have a DFL approximately 50%, 40%, or 30% of the DFL in patients receiving a non-extended release composition with the same dosing interval.

The terms "treating" or "treatment" means to relieve, alleviate, delay, reduce, reverse, improve, manage, or prevent at least one symptom of a condition in a patient. The term "treating" may also mean to arrest, delay the onset (i.e., the period prior to clinical manifestation of a disease), and/or reduce the risk of developing or worsening a condition.

As used herein, the terms "therapeutically effective amount", "prophylactically effective amount", or "diagnostically effective amount" is the amount of the drug, e.g., insulin or PEGylated C-peptide, needed to elicit the desired biological response following administration.

The term "unit-dose forms" refers to physically discrete units suitable for human and animal patients and packaged individually as is known in the art. It is contemplated for purposes of the present invention that dosage forms of the present invention comprising therapeutically effective amounts of drug may include one or more unit doses (e.g., tablets, capsules, powders, semisolids [e.g., gelcaps or films], liquids for oral administration, ampoules or vials for injection, loaded syringes) to achieve the therapeutic effect. It is further contemplated for the purposes of the present invention that a preferred embodiment of the dosage form is a subcutaneously injectable dosage form.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%.

As used herein and in the appended claims, the singular forms "a", "an", and "the" include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods and pharmaceutical compositions described herein.

Unless defined otherwise, all technical and scientific terms used herein have the same meaning as commonly understood by one of ordinary skill in the art to which the invention belongs. The following abbreviations listed in Table A are used in certain sections of the disclosure:

TABLE A

LIST OF ABBREVIATIONS

| | |
|---|---|
| ADA | Anti-drug antibody |
| AUC | Area under the curve |
| $AUC_{(0-7)}$ | Area under the plasma concentration-time curve from time zero to Day 7 |
| $AUC_{(0-14)}$ | Area under the plasma concentration-time curve from time zero to Day 14 |
| $AUC_{(0-t)}/AUC_{tau}$ | Area under the plasma concentration-time curve from time zero to the time of the last quantifiable concentration |
| $AUC_{(0-inf)}/AUC_{inf}$ | Area under the plasma concentration-time curve from time zero to infinity |
| Conc. | Concentration |
| $C_{ss}$ | Concentration at steady state |
| CL/F | Apparent clearance uncorrected for bioavailability (F) |
| $CL_{ss}/F$ | Apparent clearance uncorrected for bioavailability (F) at steady state |
| $C_{max}$ | Maximum observed concentration |
| ELISA | Enzyme-linked immunosorbent assay |
| F | Bioavailability or female |
| $F_{rel}$ | Relative bioavailability |
| GLP | Good Laboratory Practice |
| h | Hours |
| i.v. | Intravenous |
| kg | Kilogram |
| L | Liter |
| M | Male |
| mg | Milligram |
| mL | Milliliter |
| min | Minutes |

TABLE A-continued

LIST OF ABBREVIATIONS

| | |
|---|---|
| MTD | maximum tolerated dose |
| ND | Not determined |
| ng | Nanogram |
| NOEL | no observed effect level. |
| nM/nmol/L | Nanomolar |
| nmol | Nanomole |
| QC | Quality control |
| PEG | Polyethylene glycol |
| RIA | Radioimmunoassay |
| s.c./S.C. | Subcutaneous |
| SD | Standard deviation |
| $T_{1/2}$ | Terminal elimination half-life |
| $T_{max}$ | Time to reach $C_{max}$ |
| Vd/F | Apparent volume of distribution following subcutaneous administration, uncorrected for bioavailability (F) |
| $Vd_{ss}/F$ | Apparent volume of distribution following subcutaneous administration, uncorrected for bioavailability (F) at steady state |
| wk | Week |

Although any methods, compositions, reagents, cells, similar or equivalent to those described herein can be used in the practice or testing of the invention, the preferred methods and materials are described herein.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; Handbook of Drug Screening, edited by Ramakrishna Seethala, Prabhavathi B. Fernandes (2001, New York, N.Y., Marcel Dekker, ISBN 0-8247-0562-9); *Lab Ref: A Handbook of Recipes, Reagents, and Other Reference Tools for Use at the Bench*, edited by Jane Roskams and Linda Rodgers, 2002, Cold Spring Harbor Laboratory, ISBN 0-87969-630-3; Harris, J M, and Zalipsky, S, eds, *Poly(ethylene glycol), Chemistry and Biological Applications*, ACS, Washington, 1997; Veronese, F., and J. M. Harris, Eds., *Peptide and protein PEGylation*, Advanced Drug Delivery Reviews, 54(4) 453-609 (2002); Zalipsky, S., et al., "*Use of functionalized Poly(Ethylene Glycols) for modification of polypeptides*" in Polyethylene Glycol Chemistry: Biotechnical and Biomedical Applications. Each of these general texts is herein incorporated by reference.

The publications discussed above are provided solely for their disclosure before the filing date of the present application. Nothing herein is to be construed as an admission that the invention is not entitled to antedate such disclosure by virtue of prior invention.

I. Polyethylene Glycol (PEG)

PEG is a well-known polymer with good solubility in many aqueous and organic solvents, which exhibits low toxicity, lack of immunogenicity, and is clear, colorless, odorless, and stable. For these reasons and others, PEG has been selected as the preferred polymer for attachment, but it has been employed solely for purposes of illustration and not limitation. Similar products may be obtained with other water-soluble polymers, including without limitation; polyvinyl alcohol, other poly(alkylene oxides) such as poly(propylene glycol) and the like, poly(oxyethylated polyols) such as poly (oxyethylated glycerol) and the like, carboxymethylcellulose, dextran, polyvinyl alcohol, polyvinyl purrolidone, poly-1,3-dioxolane, poly-1,3,6-trioxane, ethylene/maleic anhydride, and polyaminoacids. One skilled in the art will be able to select the desired polymer based on the desired dosage, circulation time, resistance to proteolysis, and other considerations.

Representative polymeric reagents and methods for conjugating such polymers to an active moiety are described in Harris, J. M. and Zalipsky, S., Eds, Poly(ethylene glycol), *Chemistry and Biological Applications*, ACS, Washington, 1997; Veronese, F., and J. M. Harris, Eds., *Peptide and Protein PEGylation, Advanced Drug Delivery Reviews,* 54(4); 453-609 (2002); Zalipsky, S., et al., "Use of Functionalized Poly Ethylene Glycols) for Modification of Polypeptides" in *Polyethylene Glycol Chemistry: Biotechnical and Biomedical Applications*, J. M. Harris, ed., Plenus Press, New York (1992); Zalipsky (1995) *Advanced Drug Reviews* 16:157-182; and in Roberts et al., *Adv. Drug Delivery Reviews,* 54, 459-476 (2002).

A wide variety of PEG derivatives are both commercially available and suitable for use in the preparation of the PEG-conjugates of the invention. For example, NOF Corp.'s SUNBRIGHT® Series (<www.peg-drug.com>) provides numerous PEG derivatives, including methoxypolyethylene glycols and activated PEG derivatives such as succinimidyl ester, methoxy-PEG amines, maleimides, and carboxylic acids, for coupling by various methods to C-peptide and Nektar Therapeutics' Advanced PEGylation also offers diverse PEG-coupling technologies to improve the safety and efficacy of therapeutics. Additional PEGs for use in forming a C-peptide conjugate of the invention include those available from Polypure (Norway), from QuantaBioDesign LTD (Ohio) and Sunbio, Inc (South Korea). Further PEG reagents suitable for use in forming a conjugate of the invention, and methods of conjugation are described in the Pasut. G., et al., *Expert Opin. Ther. Patents* (2004), 14(6) 859-893.

A search of patents, published patent applications, and related publications will also provide those skilled in the art reading this disclosure with significant possible PEG-coupling technologies and PEG-derivatives. For example, U.S. Pat. Nos. 7,026,440; 6,858,736; 6,828,401; 6,602,498; 6,495,659; 6,448,369, 6,436,386; 5,990,237; 5,932,462; 5,900,461; 5,824,784; 5,739,208; 5,672,662; 5,650,234; 5,629,384; 5,252,714; and 4,904,584; the contents of which are incorporated by reference in their entirety, describe such technologies and derivatives, and methods for their manufacture.

The PEGylated C-peptides according to the invention have PEG moieties with a molecular weight varying within a range of about 4,000 Da to 80,000 Da. The molecular weight ranges will typically be from about 4000 Da to about 10,000 Da, from about 10,000 Da to about 20,000 Da, from about 20,000 Da to about 30,000 Da, from about 30,000 Da to about 40,000 Da, from about 40,000 Da to about 50,000 Da, from about 50,000 Da to about 60,000 Da, from about 60,000 Da to about 70,000 Da, and from about 70,000 Da to about 80,000 Da. Non-limiting examples of average molecular weights of the PEG moieties are about 10,000 Da, about 20,000 Da, about 30,000 Da, about 40,000 Da, about 50,000 Da, about 60,000 Da, about 70,000 Da, and about 80,000 Da.

Because virtually all PEG polymers exist as mixtures of diverse high molecular mass, PEG molecular weight (MW) is typically reported as number average ($M_n$), weight average ($M_w$), or z-average ($M_z$) molecular weights. The weight average is probably the most useful of the three, because it fairly accounts for the contributions of different sized chains to the overall behavior of the polymer, and correlates best with most of the physical properties of interest.

$$\text{Number average MW } (Mn) = \frac{\Sigma(MiNi)}{\Sigma Ni}$$

$$\text{Weight average MW } (Mw) = \frac{\Sigma(Mi^2 Ni)}{\Sigma(MiNi)}$$

$$Z \text{ average MW } (Mz) = \frac{\Sigma(Mi^3 Ni)}{\Sigma(Mi^2 Ni)}$$

where "Ni" is the mole-fraction (or the number-fraction) of molecules with molecular weight "Mi" in the polymer mixture. The ratio of Mw to Mn is known as the polydispersity index (PDI), and provides a rough indication of the breadth of the distribution. The PDI approaches 1.0 (the lower limit) for special polymers with very narrow MW distributions.

The PEG groups of the invention will for a given molecular weight typically consist of a range of ethylene glycol (or ethyleneoxide; $OCH_2CH_2$) monomers. For example, a PEG group of molecular weight 2000 Da will typically consist of 43±10 monomers, the average being around 43-44 monomers.

The PEG groups of the present invention will typically comprise a number of subunits, e.g., each n, $n_1$ or $n_2$ or $n_3$ in any of the claimed compounds may each independently be from about 1 to about 1000, from about 1 to about 800, from about 1 to about 600, from about 1 to about 400, from about 1 to about 300, from about 1 to about 200. Well-suited PEG groups are such wherein the number of subunits (i.e. $n_1$, $n_2$, and $n_3$) are independently selected from the group consisting of from about 800 to about 1000; from about 800 to about 950; from about 600 to about 850; from about 400 to about 650; from about 200 to about 450, from about 180 to about 350; from about 100 to about 150; from about 35 to about 55; from about 42 to about 62; from about 12 to about 25 subunits, from about 1 to 10 subunits. In certain embodiments the PEGylated C-peptide will have a molecular weight of about 40 kDa, and thus $n_1$ and $n_2$ for each PEG chain in the branch chain PEGs will be within the range of about 440 to about 550, or about 450 to about 520.

Branched versions of the PEG polymer (e.g., a branched 40,000 Da PEG polymer comprised of two or more 10,000 Da to 20,000 Da PEG polymers or the like) having a total molecular weight of any of the foregoing can also be used.

Representative branched polymers described therein include those having the following generalized structure: (PEG)y-[Core]-[Linker]; where "[Core]" is a central or core molecule from which extends 2 or more PEG arms, the variable "y" represents the number of PEG arms, and "[Linker]" represents an optional linking moiety (as further defined below) that typically couples the [Core] to the C-peptide. In one alternative embodiment of the branched chain PEGs, at least one polymer arm possesses a terminal functional group suitable (e.g. NHS moiety) for reaction with C-peptide. Typically the branched chain polymers of the invention are coupled to the N-terminal amino group of the C-peptide.

In yet further embodiments the linker moiety can represent either a hydrolytically stable, or alternatively, a degradable linker, meaning that the linkage can be hydrolyzed under physiological conditions, e.g., the linkage comprises an ester, hydrolysable carbamate, carbonate, or other such group. Hydrolytically degradable linkages, useful not only as a degradable linkage within a polymer backbone, but also, in the case of certain embodiments of the invention, for covalently attaching a water-soluble polymer to a C-peptide, include: carbonate; imine resulting, for example, from reaction of an amine and an aldehyde (see, e.g., Ouchi et al. (1997) Polymer Preprints 38(1):582-3); phosphate ester, formed, for example, by reacting an alcohol with a phosphate group; hydrazone, e.g., formed by reaction of a hydrazide and an aldehyde; acetal, e.g., formed by reaction of an aldehyde and an alcohol; orthoester, formed, for example, by reaction between a formate and an alcohol; and esters, and certain urethane (carbamate) linkages. Illustrative PEG reagents for use in preparing a releasable C-peptide conjugate in accordance with the invention are described in U.S. Pat. Nos. 6,348,558, 5,612,460, 5,840,900, 5,880,131, and 6,376,470. Typically releasable linkers may be attached to any residue in C-peptide, and are not restricted to the N-terminal amino acid.

Branched PEGs such as those represented generally by the formula, (PEG)y-[Core]-[Linker], above can possess 2 polymer arms to about 8 polymer arms (i.e., "y" ranges from 2 to about 8). Preferably, such branched PEGs typically possess from 2 to about 4 polymer arms, Multi-armed polymers include those having 2, 3, 4, 5, 6, 7 or 8 PEG arms.

Core molecules in branched PEGs as described above include polyols, which are then further functionalized. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, ducitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Typical polyols include glycerol, pentaerythritol, sorbitol, and trimethylolpropane. Other suitable cores include lysine, and other polyamines, and PEG moieties comprising multiple functional terminal end groups.

Illustrative multi-armed PEGs having 2 arms, 3 arms, 4 arms, and 8 arms are known in the art, and are available commercially and/or can be prepared following techniques known to those skilled in the art. (See generally Pasut et al., (2004) Protein, peptide and non-peptide drug PEGylation for therapeutic application Expert Opinin. Ther. Patents 14(6) 859-894). Additional branched-PEGs for use in forming a C-peptide conjugate of the present invention include those described in U.S. Patent Application Publication Nos. 20050009988, 20060194940, 20090234070, 20070031371, U.S. Pat. Nos. 6,664,331; 6,362,254; 6,437,025; 6,541,543; 6,664,331; 6,730,334; 6,774,180; 6,838,528; 7,030,278; 7,026,440; 7,053,150; 7,157,546; 7,223,803; 7,265,186; 7,419,600; 7,432,330; 7,432,331; 7,511,094; 7,528,202; 7,589,157; and PCT publication numbers WO2005000360, WO2005108463, WO2005107815, WO2005028539 and WO200605108463.

Exemplary linear or multi-armed PEGs for use herein include those of general formula (I) (II), (III) or (IV) as further described below:

In one aspect, the PEGylated C-peptide comprises a linear PEG of general formula: (I):

$$R_1—O—(CH_2CH_2O)_{n1}—[Linker]—[C\text{-peptide}] \qquad (I)$$

wherein:
$R_1$=alkyl; and
$n_1$ is 20 to 800; and
wherein the linker is as defined below, and is attached to the N-terminal amino group of C-peptide.

In another aspect, the PEGylated C-peptide comprises a branched chain PEG of general formula: (II):

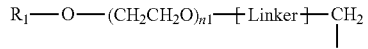

(II)

wherein:
$R_1$=alkyl;
$n_1$ is 20 to 800;
$n_2$ is 20 to 800;
wherein each linker is independently defined as below; and wherein the linker connecting to C-peptide is attached to the N-terminal amino group of C-peptide.

In one embodiment of the PEGylated C-peptides of formula (II), the PEGylated C-peptide has the structure (II A):

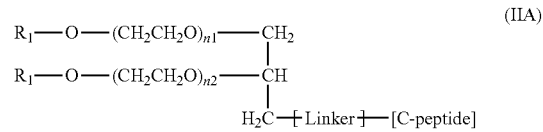

(IIA)

wherein:
$R_1$=alkyl;
$n_1$ is 20 to 800;
$n_2$ is 20 to 800; and
wherein the linker is defined as below, and is attached to the N-terminal amino group of C-peptide.

In another aspect, the PEGylated C-peptide comprises a branched chain PEG of general formula (III):

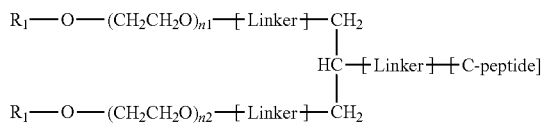

(III)

wherein:
$R_1$=alkyl;
$n_1$ is 20 to 800;
$n_2$ is 20 to 800;

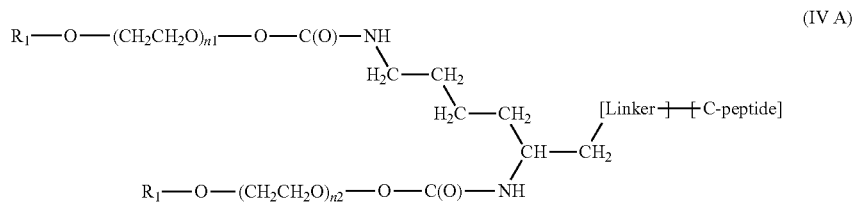

(IV A)

wherein each linker is independently defined as below, and wherein the linker connecting to C-peptide is attached to the N-terminal amino group of C-peptide.

In one embodiment of the PEGylated C-peptides of formula (III), the PEGylated C-peptide has the structure (III A):

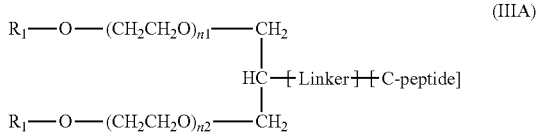

(IIIA)

wherein:
$R_1$=alkyl;
$n_1$ is 20 to 800;
$n_2$ is 20 to 800; and
wherein the linker is defined as below, and is attached to the N-terminal amino group of C-peptide.

In another aspect, the PEGylated C-peptide comprises a branched chain PEG of general formula (IV):

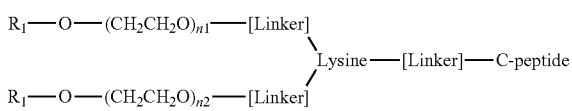

(IV)

wherein;
$R_1$=alkyl;
$n_1$ is 20 to 800;
$n_2$ is 20 to 800;

wherein each linker is independently defined as below; and wherein the linker connecting the lysine residue to C-peptide is attached to the N-terminal amino group of C-peptide and the C-terminal carboxylate group of the lysine residue, and wherein the linkers connecting the lysine moiety to the PEG moieties are linked through the amino groups of the lysine molecule.

In another embodiment of the PEGylated C-peptides of formula (IV), the PEGylated C-peptide has the structure (IV A):

wherein;
$R_1$=alkyl;
$n_1$ is 20 to 800;
$n_2$ is 20 to 800; and
wherein the linker is defined as below, and is attached to the N-terminal amino group of C-peptide.

Those of ordinary skill in the art will recognize that the foregoing discussion describing linear and branched chain PEGs for use in forming a C-peptide conjugate is by no means exhaustive and is merely illustrative, and that all polymeric materials, and branched PEG structures having the qualities described herein are contemplated. Moreover, based on the instant invention, one of ordinary skill in the art can readily determine the appropriate size and optimal structure of alternative PEGylated C-peptides using routine experimentation, for example, by obtaining the clearance profile for each conjugate by administering the conjugate to a patient and taking periodic blood and/or urine samples, as described herein. Once a series of clearance profiles has been obtained for each tested conjugate, a conjugate or mixture of conjugates, having the desired clearance profile(s) can be determined.

II. Linker Moieties

The particular linkage between the C-peptide and the water-soluble polymer depends on a number of factors, including the desired stability of the linkage, its hydrophobicity, the particular linkage chemistry employed, and impact on the aqueous solubility, and aggregation state of the PEGylated C-peptide. Exemplary linkages are hydrolytically stable, and water soluble, representative suitable linker can comprise any combination of amide, a urethane (also known as carbamate), amine, thioether (also known as sulfide), or urea (also known as carbamide) groups.

There are many commercially available examples of suitable water-soluble linker moieties and/or these can be prepared following techniques known to those skilled in the art. Certain illustrative exemplary linker moieties are described below. The corresponding activated intermediates are provided in Tables D1 and D2 below.

In one embodiment of the PEGylated C-peptides of general formula (I) (II), (III), or (IV), the PEGylated C-peptide comprises one or more linkers independently selected from:
—X—, —CO—, —(CH$_2$)$_{m2}$—, —(CH$_2$)$_{m1}$—CO—,
—CO—(CH$_2$)$_{m1}$—, —CO—X—CO—, —(CH$_2$)$_{m1}$—
X—(CH$_2$)$_{m1}$—, —(CH$_2$)$_{m1}$—CO—(CH$_2$)$_{m1}$—,
—X—CO—X—, —X—(CH$_2$)$_{m1}$—X—, —CO—

$-(CH_2)_{m1}-CO-$, $-X-CO-(CH_2)_{m1}-$, $-(CH_2)_{m1}-CO-X-$, $-X-(CH_2)_{m1}-CO-X-$, $-X-CO-(CH_2)_{m1}-X-$, $-X-CO-(CH_2)_{m1}-CO-X-(CH_2)_{m1}-X-CO-$, $-X-(CH_2)_{m1}-X-CO-(CH_2)_{m2}-$, $-X-(CH_2)_{m1}-CO-X-(CH_2)_{m2}-$, $-X-(CH_2)_{m1}-X-CO-(CH_2)_{m2}-X-$, $-X-(CH_2)_{m1}-X-CO-(CH_2)_{m2}-CO-$, $-X-(CH_2)_{m1}-CO-X-(CH_2)_{m2}-X-$, and $-X-(CH_2)_{m1}-CO-X-(CH_2)_{m2}-CO-$;

wherein;
each X is independently selected from $-O-$, $-S-$, or $-NH-$ or is missing;
each $m_1$ is independently 0 to 5; and
each $m_2$ is independently 1 to 5.

In another embodiment of the PEGylated C-peptides of formula (I) (II), (III), or (IV) the PEGylated C-peptide comprises one or more linkers independently selected from:
$-X_1-(CH_2)_{m4}-CO-$;
$-X_1-CO-$;
$-X_1-CO-(CH_2)_{m4}-CO-$;
$-X_1-CO-X_2-(CH_2)_{m3}-CO-$; and
$-X_1-(CH_2)_{m2}-X_2-CO-(CH_2)_{m4}-CO-$;

wherein;
$X_1$ is $-O-$, or missing;
$X_2$ is $-NH-$;
$m_2$ is 1 to 5;
$m_3$ is 2; and
$m_4$ is 1 to 5.

In another embodiment of the PEGylated C-peptides of formula (II), (III), or (IV) the PEGylated C-peptide comprises one or more linkers independently selected from;
$-X_1-CO-X_2-(CH_2)_{m5}-X_1-CH_2-CH_2-O)_{n3}-X-$,
$-X_1-CO-X_2-(CH_2)_{m5}-X_1-(CH_2-CH_2-O)_{n3}-(CH_2)_{m5}-CO-$,
$-X_1-CO-X_2-(CH_2)_{m5}-X_1-(CH_2-CH_2-O)_{n3}-CO-$, and
$-X_1-CO-X_2-(CH_2)_{m5}-X_1-(CH_2-CH_2-O)_{n3}-CO-(CH_2)_{m5}-CO-$;

wherein;
X is independently selected from $-O-$, $-S-$, or $-NH-$ or is missing;
$X_1$ is $-O-$, or missing;
$X_2$ is $-NH-$;
each $m_5$ is independently selected from 1 to 5; and
each $n_3$ is independently selected from 1 to 400.

In another embodiment of the PEGylated C-peptides of formula (II), (III) or (IV), the PEGylated C-peptide comprises one or more linkers independently selected from:
$-X_1-CO-X_2-(CH_2)_{m5}-X_1-(CH_2-CH_2-O)_{n3}-(CH_2)_{m6}-CO-$,
$-X_1-CO-X_2-(CH_2)_{m5}-X_1-(CH_2-CH_2-O)_{n3}-CO-$, and
$-X_1-CO-X_2-(CH_2)_{m5}-X_1-(CH_2-CH_2-O)_{n3}-CO-(CH_2)_{m7}-CO-$;

wherein;
$X_1$ is $-O-$, or is missing;
$X_2$ is $-NH-$;
$m_5$ is 3;
$m_6$ is independently 2 or 5;
$m_7$ is 3; and
$n_3$ is 1 to 400.

In another embodiment of the PEGylated C-peptides of formula (IV), the PEGylated C-peptide comprises a linker independently selected from:
$-X-$, $-CO-$, $-(CH_2)_{m2}-$, and $-X_1-C(O)-X_2-$;
wherein;

X is $-O-$, or $-S-$, or $-NH-$ or is missing;
$X_1$ and $X_2$ are independently selected from $-NH-$; or $-O-$, or is missing; and
$m_2$ is independently 1 to 5.

Those of ordinary skill in the art will recognize that the foregoing discussion describing linker moieties for use in forming a C-peptide conjugate is by no means exhaustive and is merely illustrative, and that all linkers having the qualities described herein are contemplated.

Moreover, based on the teachings described herein, one of ordinary skill in the art can readily determine the appropriate size and optimal structure of the linker using routine experimentation. For example by testing a number of different commercially available PEG derivatives with different linker moieties and characterizing the biological activity, solubility and stability of the resulting PEGylated C-peptide.

III. Activated Functional Groups and Reaction Conditions

The only natural free amino group in human C-peptide is the N-terminal amino group, and thus the selective conjugation of a polymeric PEG group to the N-terminal amino group of C-peptide can be readily accomplished using a variety of commercially available activated PEGs and standard coupling approaches.

In one approach, a C-peptide is conjugated to the PEG reagent via an activated functional group, such as an active ester such as a succinimidyl derivative (e.g., an N-hydroxysuccinimide ester (NHS)). In this approach, the PEG bearing the reactive ester is reacted with the C-peptide in aqueous media under appropriate pH conditions, at room temperature or 4° C., for a few hours to overnight. Typically the polymeric reagent is coupled to the activated functional group via a linker as described herein.

N-terminal PEGylation, with a PEG reagent bearing an N-hydroxysuccinimide ester (NHS group), is typically carried out at room temperature, or 4° C., in a polar aprotic solvent such as dimethylformamide (DMF) or acetonitrile, or a combination thereof (with small amounts of water to solubilize the peptide) under slightly basic pH conditions, e.g., from pHs ranging from about 7.5 to about 8. Reaction times are typically in the range of 1 to 24 hours, depending upon the pH and temperature of the reaction.

N-terminal PEGylation, with a PEG reagent bearing an aldehyde group, is typically conducted under mild conditions, in the presence of sodium cyanoborohydride (10 equiv.), 4° C., at pHs from about 5 to 10, for about 20 to 36 hours. N-terminal pegylation may be conducted, for example, in 100 mM sodium acetate or 100 mM sodium biphosphate buffer at pH 5.0-6.0. The buffer may additionally contain 20 mM sodium cyanoborahydride. The molar ratio of compound to mPEG-aldehyde may be 1:5~1:10. The pegylation is then stirred overnight at ambient or refrigeration temperature.

N-terminal PEGylation, with a PEG reagent bearing p-Nitrophenyloxycarbonyl group, is typically conducted with borate or phosphate buffer at pHs from about 8 to 8.3, at room temperature overnight.

For all the coupling reactions, varying ratios of polymeric reagent to C-peptide may be employed, e.g., from an equimolar ratio up to a 10-fold molar excess of polymer reagent. Typically, up to a 2-fold molar excess of polymer reagent will suffice. Exemplary activated PEGs include, e.g., those listed in Table D1 and Table D2. In the following list, selected PEGylation reagents are listed. Obviously other active groups and linkers may be employed, and are known to those skilled in the art.

TABLE D1

Exemplary Activated Linear PEGs

| Structure/Functionality | Abbreviation & Molecular Weight Range (in Da) |
|---|---|
| 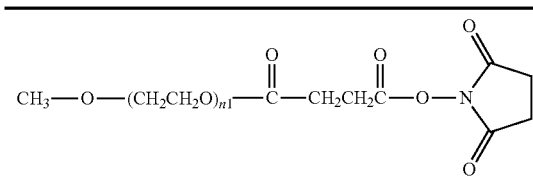<br>N-hydroxysuccinimide ester | SUNBRIGHT ME-020CS MW = 2,000<br>SUNBRIGHT ME-050CS MW = 5,000<br>SUNBRIGHT ME-100CS MW = 10,000<br>SUNBRIGHT ME-200CS MW = 20,000<br>SUNBRIGHT ME-300CS MW = 30,000<br>SUNBRIGHT ME-400CS MW = 40,000 |
| 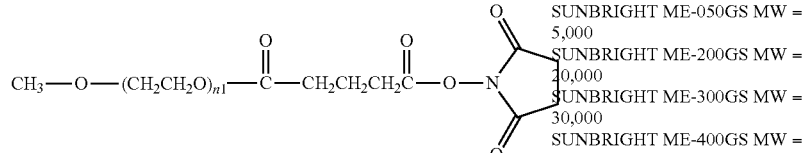<br>N-hydroxysuccinimide ester | SUNBRIGHT ME-050GS MW = 5,000<br>SUNBRIGHT ME-200GS MW = 20,000<br>SUNBRIGHT ME-300GS MW = 30,000<br>SUNBRIGHT ME-400GS MW = 40,000 |
| 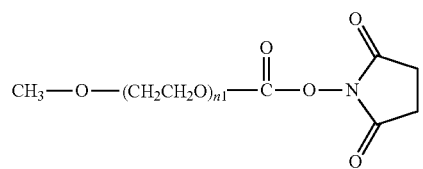<br>N-hydroxysuccinimide ester | SUNBRIGHT ME-050TS MW = 5,000<br>SUNBRIGHT ME-200TS MW = 20,000<br>SUNBRIGHT ME-300TS MW = 30,000<br>SUNBRIGHT ME-400TS MW = 40,000 |
| 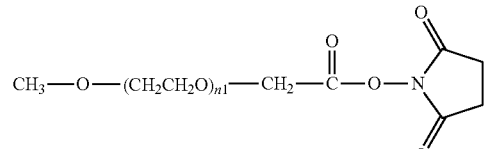<br>N-hydroxysuccinimide ester | SUNBRIGHT ME-020AS MW = 2,000<br>SUNBRIGHT ME-050AS MW = 5,000 |
| 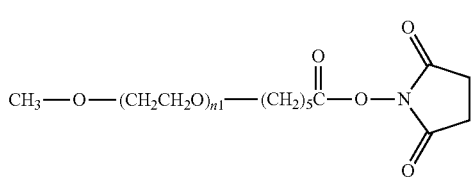<br>N-hydroxysuccinimide ester | SUNBRIGHT ME-050HS MW = 5,000<br>SUNBRIGHT ME-200HS MW = 20,000<br>SUNBRIGHT ME-300HS MW = 30,000<br>SUNBRIGHT ME-400HS MW = 40,000 |
| 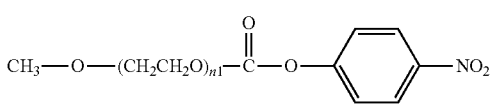<br>p-Nitrophenyl | SUNBRIGHT MENP-020H MW = 2,000<br>SUNBRIGHT MENP-050H MW = 5,000<br>SUNBRIGHT MENP-10T MW = 10,000<br>SUNBRIGHT MENP-20T MW = 20,000<br>SUNBRIGHT MENP-30T MW = 30,000<br>SUNBRIGHT MENP-40T MW = 40,000 |
| $CH_3O-(CH_2CH_2O)_{n1}-N=C=O$<br>Isocyanate | |

TABLE D1-continued

Exemplary Activated Linear PEGs

| Structure/Functionality | Abbreviation & Molecular Weight Range (in Da) |
|---|---|
| $CH_3-O-(CH_2CH_2O)_{n1}-CH_2-\overset{O}{\underset{\|}{C}}-O-CH_2CH_2\overset{O}{\underset{\|}{C}}H$<br>Aldehyde | SUNBRIGHT ME-050AL MW = 5,000<br>SUNBRIGHT ME-100AL MW = 10,000<br>SUNBRIGHT ME-200AL MW = 20,000<br>SUNBRIGHT ME-300AL MW = 30,000<br>SUNBRIGHT ME-400AL MW = 40,000 |
| $CH_3-O-(CH_2CH_2O)_{\overline{n1}}CH_2CH_2\overset{O}{\underset{\|}{C}}H$<br>Aldehyde | SUNBIO P1PAL-5 MW = 5,000<br>SUNBIO P1PAL-10 MW = 10,000<br>SUNBIO P1PAL-20 MW = 20,000<br>SUNBIO P1PAL-30 MW = 30,000 |
| $CH_3-O-(CH_2CH_2O)_{\overline{n1}}CH_2\overset{O}{\underset{\|}{C}}NHCH_2CH_2\overset{O}{\underset{\|}{C}}H$<br>Amide Aldehyde | SUNBIO P1APAL-5 MW = 5,000<br>SUNBIO P1APAL-10 MW = 10,000<br>SUNBIO P1APAL-20 MW = 20,000<br>SUNBIO P1APAL-30 MW = 30,000 |
| $CH_3-O-(CH_2CH_2O)_{\overline{n1}}\overset{O}{\underset{\|}{C}}NHCH_2CH_2\overset{O}{\underset{\|}{C}}H$<br>Urethane Aldehyde | SUNBIO P1TPAL-5 MW = 5,000 |
| $CH_3-O-(CH_2CH_2O)_{n1}-CH_2CH_2CH_2\overset{O}{\underset{\|}{C}}H$<br>Aldehyde | SUNBIO P1BAL-5 MW = 5,000<br>SUNBIO P1BAL-10 MW = 10,000<br>SUNBIO P1BAL-20 MW = 20,000<br>SUNBIO P1BAL-30 MW = 30,000 |
| $CH_3-O-(CH_2CH_2O)_{\overline{n1}}CH_2\overset{O}{\underset{\|}{C}}NHCH_2CH_2CH_2\overset{O}{\underset{\|}{C}}H$<br>Amide Aldehyde | SUNBIO P1ABAL-5 MW = 5,000<br>SUNBIO P1ABAL-10 MW = 10,000<br>SUNBIO P1ABAL-20 MW = 20,000<br>SUNBIO P1ABAL-30 MW = 30,000 |
| $CH_3-O-(CH_2CH_2O)_{\overline{n1}}\overset{O}{\underset{\|}{C}}NHCH_2CH_2CH_2\overset{O}{\underset{\|}{C}}H$<br>Urethane Aldehyde | SUNBIO P1TBAL-5 MW = 5,000 |
| $R_1O(CH_2CH_2O)n-C(O)_x-(CH_2)_y-C(O)-O-N\text{-succinimide}$<br>N-hydroxysuccinimide ester | X = 0, y = 1 SUNBRIGHT-AS<br>X = 0, y = 5, SUNBRIGHT-HS<br>X = 1, y = 2 SUNBRIGHT-CS<br>X = 1, y = 3 SUNBRIGHT-GS |

TABLE D1-continued

Exemplary Activated Linear PEGs

| Structure/Functionality | Abbreviation & Molecular Weight Range (in Da) |
|---|---|
| 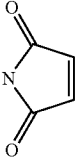 $R_1O(CH_2CH_2O)_n$—$(CH_2)_3NH$—$(CH_2)_z$—N(maleimide)<br><br>Maleimide | z = 2 SUNBRIGHT-MA<br>z = 5 SUNBRIGHT-MA3 |

TABLE D2

Exemplary Activated Branched PEGs

| Structure/Functionality | Abbreviation & Molecular Weight Range (in Da) |
|---|---|
| $R_1$—O—$(CH_2CH_2O)_{n1}$—$CH_2$<br>$R_1$—O—$(CH_2CH_2O)_{n2}$—CH<br>$H_2C$—$OCH_2CH_2CH_2NHC(O)(CH_2)_3CO$—N(succinimide)<br><br>N-hydroxysuccinimide ester | SUNBRIGHT GL2-200GS2 MW = 20,000<br>SUNBRIGHT GL2-400GS2 MW = 40,000<br>SUNBRIGHT GL2-400GS2 MW = 60,000<br>SUNBRIGHT GL2-800GS2 MW = 80,000 |
| $R_1$—O—$(CH_2CH_2O)_{n1}$—$CH_2$<br>$R_1$—O—$(CH_2CH_2O)_{n2}$—CH<br>$H_2C$—$OCO$—C$_6$H$_4$—$NO_2$<br><br>p-Nitrophenyl | SUNBRIGHT GL2-100NP MW = 10,000<br>SUNBRIGHT GL2-200NP MW = 20,000<br>SUNBRIGHT GL2-400NP MW = 40,000<br>SUNBRIGHT GL2-600NP MW = 60,000<br>SUNBRIGHT GL2-800NP MW = 80,000 |
| $R_1$—O—$(CH_2CH_2O)_{n1}$—$CH_2$<br>$R_1$—O—$(CH_2CH_2O)_{n2}$—CH<br>$H_2C$—$OCO$—N(succinimide)<br><br>N-hydroxysuccinimide ester | SUNBRIGHT GL2-200TS MW = 20,000<br>SUNBRIGHT GL2-400TS MW = 40,000<br>SUNBRIGHT GL2-600TS MW = 60,000<br>SUNBRIGHT GL2-800TS MW = 80,000 |
| $R_1$—O—$(CH_2CH_2O)_{n1}$—$CH_2$<br>$R_1$—O—$(CH_2CH_2O)_{n2}$—CH<br>$H_2C$—$OCNHCH_2CH_2CH$—<br><br>Aldehyde | SUNBRIGHT GL2-200AL3 MW = 20,000<br>SUNBRIGHT GL2-400AL3 MW = 40,000<br>SUNBRIGHT GL2-600AL3 MW = 60,000<br>SUNBRIGHT GL2-800AL3 MW = 80,000 |
| $R_1$—O—$(CH_2CH_2O)_{n1}$—$CH_2$<br>$R_1$—O—$(CH_2CH_2O)_{n2}$—CH<br>$H_2C$—$OCNH(CH_2)_3O(CH_2CH_2O)_{n3}$—$CH_2CH_2CH$<br><br>Aldehyde | SUNBRIGHT GL3-400AL100U MW = 50,000 |

TABLE D2-continued

Exemplary Activated Branched PEGs

| Structure/Functionality | Abbreviation & Molecular Weight Range (in Da) |
|---|---|
| p-Nitrophenyl | SUNBRIGHT GL3-400NP100U<br>MW = 50,000 |
| N-hydroxysuccinimide ester | SUNBRIGHT GL3-400GS100U<br>MW = 50,000 |
| N-hydroxysuccinimide ester | SUNBRIGHT GL3-400HS100U<br>MW = 50,000 |
| N-hydroxysuccinimide ester | SUNBRIGHT LY-400NS<br>MW = 40,000 |
| | MW = 40,000 |

The PEGylated C-peptide can be purified after neutralization of the reaction buffer, by any convenient approach, e.g., by precipitation with isopropyl-ether followed by reverse phase HPLC or ion exchange chromatography.

IV. Therapeutic Forms of C-peptide

The terms "C-peptide" or "proinsulin C-peptide" as used herein includes all naturally-occurring and synthetic forms of C-peptide that retain C-peptide activity. Such C-peptides include the human peptide, as well as peptides derived from other animal species and genera, preferably mammals. Preferably, "C-peptide" refers to human C-peptide having the amino acid sequence EAEDLQVGQVELGGGPGAGSLQ-PLALEGSLQ (SEQ. ID. No. 1 in Table D3).

C-peptides from a number of different species have been sequenced, and are known in the art to be at least partially functionally interchangeable. It would thus be a routine matter to select a variant being a C-peptide from a species or genus other than human. Several such variants of C-peptide (i.e., representative C-peptides from other species) are shown in Table D3 (see SEQ. ID. Nos. 1-29).

TABLE D3

| | | C-peptide Variants | |
|---|---|---|---|
| human M-proisulin | Human (SEQ. ID. No. 1) | EAEDLQVGQVELGGGPGAGSLQPLALEGSLQ | gb\|AAA72531.1\| dbj\|BAH59081.1\| |
| *Pan troglodytes* | (SEQ. ID. No. 1) Alignment (SEQ. ID. No. 2) Identities = 31/31 (100%), Positives = 31/31 (100%), Gaps = 0/31 (0%) | EAEDLQVGQVELGGGPGAGSLQPLALEGSLQ EAEDLQVGQVELGGGPGAGSLQPLALEGSLQ EAEDLQVGQVELGGGPGAGSLQPLALEGSLQ | NP_001008996.1\| emb\|CAA43403.1\| GENE ID: 449570 INS |
| *Gorilla gorilla* | (SEQ. ID. No. 1) Alignment (SEQ. ID. No. 3) Identities = 31/31 (100%), Positives = 31/31 (100%), Gaps = 0/31 (0%) | EAEDLQVGQVELGGGPGAGSLQPLALEGSLQ EAEDLQVGQVELGGGPGAGSLQPLALEGSLQ EAEDLQVGQVELGGGPGAGSLQPLALEGSLQ | gb\|AAN06935.1\| |
| *Pongo pygmaeus* (Bornean orangutan) | (SEQ. ID. No. 1) (SEQ. ID. No. 4) Identities = 31/31 (100%), Positives = 31/31 (100%), Gaps = 0/31 (0%) | EAEDLQVGQVELGGGPGAGSLQPLALEGSLQ EAEDLQVGQVELGGGPGAGSLQPLALEGSLQ EAEDLQVGQVELGGGPGAGSLQPLALEGSLQ | gb\|AAN06937.1\| |
| *Chlorocebus aethiops* (Monkey) | (SEQ. ID. No. 1) (SEQ. ID. No. 5) Identities = 30/31 (96%), Positives = 30/31 (96%), Gaps = 0/31 (0%) | EAEDLQVGQVELGGGPGAGSLQPLALEGSLQ EAED QVGQVELGGGPGAGSLQPLALEGSLQ EAEDPQVGQVELGGGPGAGSLQPLALEGSLQ | emb\|CAA43405.1\| |
| *Canis lupus familiaris* (Dog) | (SEQ. ID. No. 1) (SEQ. ID. No. 6) Identities = 23/31 (74%), Positives = 24/31 (77%), Gaps = 0/31 (0%) | EAEDLQVGQVELGGGPGAGSLQPLALEGSLQ E EDLQV VEL G PG G LQPLALEG+LQ EVEDLQVRDVELAGAPGEGGLQPLALEALQ | ref\|NP_001123565.1\| sp\|P01321.1\|INS_ CANFAemb\|CAA23475.1\| GENE ID: 483665 INS |
| *Oryctolagus cuniculus* (Rabbit) | (SEQ. ID. No. 1) (SEQ. ID. No. 7) Identities = 23/31 (74%), Positives = 25/31 (80%), Gaps = 0/31 (0%) | EAEDLQVGQVELGGGPGAGSLQPLALEGSLQ E E+LQVGQ ELGGGP AG LQP ALE +LQ EVEELQVGQAELGGGPDAGGLQPSALELALQ | gb\|ACK44319.1\| |
| *Rattus norvegicus* | (SEQ. ID. No. 1) (SEQ. ID. No. 8) Identities = 22/31 (70%), Positives = 24/31 (77%), Gaps = 0/31 (0%) | EAEDLQVGQVELGGGPGAGSLQPLALEGSLQ E ED QV Q+ELGGGPGAG LQ LALE + Q EVEDPQVAQLELGGGPGAGDLQTLALEVARQ | ref\|NP_062003.1\| sp\|P01323.1\| INS2_RAT emb\|CAA24560.1\| GENE ID: 24506 Ins2 |
| *Apodemus semotus* (Taiwan field mouse) | (SEQ. ID. No. 1) (SEQ. ID. No. 9) Identities = 22/31 (70%), Positives = 24/31 (77%), Gaps = 0/31 (0%) | EAEDLQVGQVELGGGPGAGSLQPLALEGSLQ E ED QV Q+ELGGGPGAG LQ LALE + Q EVEDPQVAQLELGGGPGAGDLQTLALEVARQ | gb\|ABB89748.1\| |
| *Geodia cydonium* sponge | (SEQ. ID. No. 1) (SEQ. ID. No. 10) Identities = 23/31 (74%), Positives = 24/31 (77%), Gaps = 0/31 (0%) | EAEDLQVGQVELGGGPGAGSLQPLALEGSLQ E ED QVGQVELG GPGAGS Q LALE + Q EVEDPQVGQVELGAGPGAGSEQTLALEVARQ | pir\|\|S09278 |
| *Mus musculus* | (SEQ. ID. No. 1) (SEQ. ID. No. 11) Identities = 21/27 (77%), Positives = 22/27 (81%), Gaps = 0/27 (0%) | EAEDLQVGQVELGGGPGAGSLQPLALE E ED QV Q+ELGGGPGAG LQ LALE EVEDPQVAQLELGGGPGAGDLQTLALE | ref\|NP_032413.1\| sp\|P01326.1\| INS2_MOUSEemb\| CAA28433.1\| GENE ID: 16334 Ins2 |
| *Mus caroli* (Ryukyu mouse) | (SEQ. ID. No. 1) (SEQ. ID. No. 12) Identities = 21/27 (77%), Positives = 22/27 (81%), Gaps = 0/27 (0%) | EAEDLQVGQVELGGGPGAGSLQPLALE E ED QV Q+ELGGGPGAG LQ LALE EVEDPQVAQLELGGGPGAGDLQTLALE | gb\|ABB89749.1\| |
| *Rattus norvegicus* | (SEQ. ID. No. 1) (SEQ. ID. No. 13) Identities = 22/31 (70%), Positives = 24/31 (77%), Gaps = 0/31 (0%) | EAEDLQVGQVELGGGPGAGSLQPLALEGSLQ E ED QV Q+ELGGGPGAG LQ LALE + Q EVEDPQVPQLELGGGPGAGDLQTLALEVARQ | prf\|\|720460B |

TABLE D3-continued

C-peptide Variants

| | | |
|---|---|---|
| *Rattus losea* | (SEQ. ID. No. 1) EAEDLQVGQVELGGGPGAGSLQPLALEGSLQ<br>E ED QV Q ELGGGPGAG LQ LALE + Q<br>(SEQ. ID. No. 14) EVEDPQVAQQELGGGPGAGDLQTLALEVARQ<br>Identities = 22/31 (70%), Positives = 23/31<br>(74%), Gaps = 0/31 (0%) | gb\|ABB89747.1\| |
| *Niviventer coxingi* (Coxing's white bellied rat) | (SEQ. ID. No. 1) EAEDLQVGQVELGGGPGAGSLQPLALEGSLQ<br>E ED QV Q+ELGGGPG G LQ LALE + Q<br>(SEQ. ID. No. 15) EVEDPQVPQLELGGGPGTGDLQTLALEVARQ<br>Identities = 21/31 (67%), Positives = 23/31<br>(74%), Gaps = 0/31 (0%) | gb\|ABB89750.1\| |
| *Microtus kikuchii* (Taiwan vole) | (SEQ. ID. No. 1) AEDLQVGQVELGGGPGAGSLQPLALE<br>ED QV Q+ELGGGPGAG LQ LALE<br>(SEQ. ID. No. 16) VEDPQVAQLELGGGPGAGDLQTLALE<br>Identities = 20/26 (76%), Positives = 21/26<br>(80%), Gaps = 0/26 (0%) | gb\|ABB89752.1\| |
| *Rattus norvegicus* insulin1 precursor | (SEQ. ID. No. 1) EAEDLQVGQVELGGGPGAGSLQPLALEGSLQ<br>E ED QV Q+ELGGGP AG LQ LALE + Q<br>(SEQ. ID. No. 17) EVEDPQVPQLELGGGPEAGDLQTLALEVARQ<br>Identities = 21/31 (67%), Positives = 23/31<br>(74%), Gaps = 0/31 (0%) | ref\|NP_062002.1\|<br>gb\|AAA41439.1\|<br>gb\|AAA41442.1\|<br>emb\|CAA24559.1\|<br>gb\|EDL94407.1\|<br>GENE ID:<br>24505 Ins1 |
| *Felis catus* (Domestic cat) | (SEQ. ID. No. 1) EAEDLQVGQVELGGGPGAGSLQPLALEGSLQ<br>EAEDLQ ELG PGAG LQP ALE LQ<br>(SEQ. ID. No. 18) EAEDLQGKDAELGEAPGAGGLQPSALEAPLQ<br>Identities = 21/31 (67%), Positives = 21/31<br>(67%), Gaps = 0/31 (0%) | ref\|NP_001009272.1\|<br>sp\|P06306.2\|<br>INS_FELCA<br>dbj\|BAB84110.1\|<br>GENE ID:<br>493804 INS |
| Golden hamster | (SEQ. ID. No. 1) AEDLQVGQVELGGGPGAGSLQPLALE<br>ED QV Q+ELGGGPGA LQ LALE<br>(SEQ. ID. No. 19) VEDPQVAQLELGGGPGADDLQTLALE<br>Identities = 19/26 (73%), Positives = 20/26<br>(76%), Gaps = 0/26 (0%) | sp\|P01313.2\|<br>INS_CRILO<br>pir\|\|I48166<br>gb\|AAA37089.1\| |
| *Niviventer coxingi* (Coxing's white bellied rat) | (SEQ. ID. No. 1) EAEDLQVGQVELGGGPGAGSLQPLALEGSLQ<br>E ED QV Q+ELG GP AG LQ LALE + Q<br>(SEQ. ID. No. 20) EVEDPQVAQLELGEGPEAGDLQTLALEVARQ<br>Identities = 20/31 (64%), Positives = 22/31<br>(70%), Gaps = 0/31 (0%) | gb\|ABB89746.1\| |
| *Apodemus semotus* (Taiwan field mouse) | (SEQ. ID. No. 1) EAEDLQVGQVELGGGPGAGSLQPLALEGSLQ<br>E ED QV Q+ELGG PG G L+ LALE + Q<br>(SEQ. ID. No. 21) EVEDPQVEQLELGGAPGTGDLETLALEVARQ<br>Identities = 19/31 (61%), Positives = 22/31<br>(70%), Gaps = 0/31 (0%) | gb\|ABB89744.1\| |
| *Rattus losea* | (SEQ. ID. No. 1) EAEDLQVGQVELGGGPGAGSLQPLALEGSLQ<br>E ED QV Q+ELGG P AG LQ LALE + Q<br>(SEQ. ID. No. 22) EVEDPQVPQLELGGSPEAGDLQTLALEVARQ<br>Identities = 20/31 (64%), Positives = 22/31<br>(70%), Gaps = 0/31 (0%) | gb\|ABB89743.1\| |
| *Meriones unguiculatus* (Mongolian gerbil) | (SEQ. ID. No. 1) AEDLQVGQVELGGGPGAGSLQPLALEGSLQ<br>ED Q+ Q+ELGG PGAG LQ LALE + Q<br>(SEQ. ID. No. 23) VEDPQMPQLELGGSPGAGDLQALALEVARQ<br>Identities = 19/30 (63%), Positives = 22/30<br>(73%), Gaps = 0/30 (0%) | gb\|ABB89751.1\| |
| *Psammomys obesus* (Fat sand rat) | (SEQ. ID. No. 1) AEDLQVGQVELGGGPGAGSLQPLALEGSLQ<br>+D Q+ Q+ELGG PGAG L+ LALE + Q<br>(SEQ. ID. No. 24) VDDPQMPQLELGGSPGAGDLRALALEVARQ<br>Identities = 17/30 (56%), Positives = 22/30<br>(73%), Gaps = 0/30 (0%) | sp\|Q62587.1\|<br>INS_PSAOB<br>emb\|CAA66897.1\| |
| *Sus scrofa* (Pig) | (SEQ. ID. No. 1) EAEDLQVGQVELGGGPGAGSLQPLALEG<br>EAE+ Q G VELGG G G LQ LALEG<br>(SEQ. ID. No. 25) EAENPQAGAVELGG--GLGGLQALALEG<br>Identities = 19/28 (67%), Positives = 20/28<br>(71%), Gaps = 2/28 (7%) | ref\|NP_001103241.1\| |

TABLE D3-continued

C-peptide Variants

| Species | Sequence | Accession |
|---|---|---|
| *Rhinolophus ferrumequinum* | (SEQ. ID. No. 26) EVEDPQAGQVELGGGPGTGGLQSLALEGPPQ | gb\|ACC68945.1\| |
| *Equus przewalskii* (Horse) | (SEQ. ID. No. 27) EAEDPQVGEVELGGGPGLGGLQPLALAGPQQ | GENE ID: 100060077 LOC100060077 gb\|AAB25818.1\| |
| *Bos Taurus* (Bovine) | (SEQ. ID. No. 28) EVEGPQVGALELAGGPGAGGLEGPPQ | gb\|AAI42035.1\| |
| *Otolemur garnettii* (Small-eared galago) | (SEQ. ID. No. 29) DTEDPQVGQVGLGGSPITGDLQSLALDVPPQ | gb\|ACH53103.1\| |

Thus all such homologues, orthologs, and naturally-occurring isoforms of C-peptide from human as well as other species (SEQ. ID Nos. 1-29) are included in any of the methods and pharmaceutical compositions of the invention, as long as they retain detectable C-peptide activity.

The C-peptides may be in their native form, i.e., as different variants as they appear in nature in different species which may be viewed as functionally equivalent variants of human C-peptide, or they may be functionally equivalent natural derivatives thereof, which may differ in their amino acid sequence, e.g., by truncation (e.g., from the N- or C-terminus or both) or other amino acid deletions, additions, insertions, substitutions, or post-translational modifications. Naturally-occurring chemical derivatives, including post-translational modifications and degradation products of C-peptide, are also specifically included in any of the methods and pharmaceutical compositions of the invention including, e.g., pyroglutamyl, iso-aspartyl, proteolytic, phosphorylated, glycosylated, oxidatized, isomerized, and deaminated variants of C-peptide.

It is known in the art to synthetically modify the sequences of proteins or peptides, while retaining their useful activity, and this may be achieved using techniques which are standard in the art and widely described in the literature, e.g., random or site-directed mutagenesis, cleavage, and ligation of nucleic acids, or via the chemical synthesis or modification of amino acids or polypeptide chains. Similarly it is within the skill in the art to address and/or mitigate immunogenicity concerns if they arise using C-peptide variants, e.g., by the use of automated computer recognition programs to identify potential T cell epitopes, and directed evolution approaches to identify less immunogenic forms.

Any such modifications, or combinations thereof, may be made and used in any of the methods and pharmaceutical compositions of the invention, as long as activity is retained. The C-terminal end of the molecule is known to be important for activity. Preferably, therefore, the C-terminal end of the C-peptide should be preserved in any such C-peptide variants or derivatives, more preferably the C-terminal pentapeptide of C-peptide (EGSLQ) (SEQ. ID. No. 31) should be preserved or sufficient (see Henriksson M et al.: *Cell Mol. Life. Sci.* 62: 1772-1778, (2005)). As mentioned above, modification of an amino acid sequence may be by amino acid substitution, e.g., an amino acid may be replaced by another that preserves the physicochemical character of the peptide (e.g., A may be replaced by G or vice versa, V by A or L; E by D or vice versa; and Q by N). Generally, the substituting amino acid has similar properties, e.g., hydrophobicity, hydrophilicity, electronegativity, bulky side chains, etc., to the amino acid being replaced.

Modifications to the mid-part of the C-peptide sequence (e.g., to residues 13 to 25 of human C-peptide) allow the production of functional derivatives or variants of C-peptide. Thus, C-peptides which may be used in any of the methods or pharmaceutical compositions of the invention may have amino acid sequences which are substantially homologous, or substantially similar to the native C-peptide amino acid sequences, e.g., to the human C-peptide sequence of SEQ. ID. No. 1 or any of the other native C-peptide sequences shown in Table D3. Alternatively, the C-peptide may have an amino acid sequence having at least 30% preferably at least 40, 50, 60, 70, 75, 80, 85, 90, 95, 98, or 99% identity with the amino acid sequence of any one of SEQ. ID. Nos. 1-29 as shown in Table D3, preferably with the native human sequence of SEQ. ID. No. 1. In a preferred embodiment, the C-peptide for use in any of the methods or pharmaceutical compositions of the present invention is at least 80% identical to a sequence selected from Table D3. In another aspect, the C-peptide for use in any of the methods or pharmaceutical compositions of the invention is at least 80% identical to human C-peptide (SEQ. ID. No. 1). Although any amino acid of C-peptide may be altered as described above, it is preferred that one or more of the glutamic acid residues at positions 3, 11, and 27 of human C-peptide (SEQ. ID. No. 1) or corresponding or equivalent positions in C-peptide of other species, are conserved. Preferably, all of the glutamic acid residues at positions 3, 11, and 27 (or corresponding Glu residues) of SEQ. ID. No. 1 are conserved. Alternatively, it is preferred that Glu27 of human C-peptide (or a corresponding Glu residue of a non-human C-peptide) is conserved. An exemplary functional equivalent form of C-peptide which may be used in any of the methods or pharmaceutical compositions of the invention includes the amino acid sequences:

(SEQ. ID. No. 30)
EXEXXQXXXXELXXXXXXXXXXXXALBXXXQ.

(SEQ. ID. No. 33)
GXEXXQXXXXELXXXXXXXXXXXXALBXXXQ.

As used herein, X is any amino acid. The N-terminal residue may be either Glu or Gly (SEQ. ID. No. 30 or SEQ. ID. No. 33, respectively). Functionally equivalent derivatives or variants of native C-peptide sequences may readily be prepared according to techniques well-known in the art, and include peptide sequences having a functional, e.g., a biological activity of a native C-peptide.

Fragments of native or synthetic C-peptide sequences may also have the desirable functional properties of the peptide from which they were derived and may be used in any of the methods or pharmaceutical compositions of the invention. The term "fragment" as used herein thus includes fragments of a C-peptide provided that the fragment retains the biological or therapeutically beneficial activity of the whole molecule. The fragment may also include a C-terminal fragment of C-peptide. Preferred fragments comprise residues 15-31 of native C-peptide, more especially residues 20-31. Peptides comprising the pentapeptide EGSLQ (SEQ. ID. No. 31) (residues 27-31 of native human C-peptide) are also preferred. The fragment may thus vary in size from, e.g., 4 to 30 amino acids or 5 to 20 residues. Suitable fragments are disclosed in WO 98/13384 the contents of which are incorporated herein by reference.

The fragment may also include an N-terminal fragment of C-peptide, typically having the sequence EAEDLQVGQVEL (SEQ. ID. No. 32), or a fragment thereof which comprises 2 acidic amino acid residues, capable of adopting a conformation where said two acidic amino acid residues are spatially separated by a distance of 9-14 Å between the alpha-carbons thereof. Also included are fragments having N- and/or C-terminal extensions or flanking sequences. The length of such extended peptides may vary, but typically are not more than 50, 30, 25, or 20 amino acids in length. Representative suitable fragments are described in U.S. Pat. No. 6,610,649, which is hereby incorporated by reference in its entirety.

In such a case it will be appreciated that the extension or flanking sequence will be a sequence of amino acids which is not native to a naturally-occurring or native C-peptide, and in particular a C-peptide from which the fragment is derived. Such a N- and/or C-terminal extension or flanking sequence may comprise, e.g., from 1 to 10, 1 to 6, 1 to 5, 1 to 4, or 1 to 3 amino acids.

The term "derivative" as used herein thus refers to C-peptide sequences or fragments thereof, which have modifications as compared to the native sequence. Such modifications may be one or more amino acid deletions, additions, insertions, and/or substitutions. These may be contiguous or non-contiguous. Representative variants may include those having 1 to 6, or more preferably 1 to 4, 1 to 3, or 1 or 2 amino acid substitutions, insertions, and/or deletions as compared to any of SEQ. ID. Nos. 1-33. The substituted amino acid may be any amino acid, particularly one of the well-known 20 conventional amino acids (Ala (A); Cys (C); Asp (D); Glu (E); Phe (F); Gly (G); His (H); Ile (I); Lys (K); Leu (L); Met (M); Asn (N); Pro (P); Gin (O); Arg (R); Ser (S); Thr (T); Val (V); Trp (W); and Tyr (Y)). Any such variant or derivative of C-peptide may be used in any of the methods or pharmaceutical compositions of the invention.

Isomers of the native L-amino acids, e.g., D-amino acids may be incorporated in any of the above forms of C-peptide, and used in any of the methods or pharmaceutical compositions of the invention. Additional variants may include amino and/or carboxyl terminal fusions as well as intrasequence insertions of single or multiple amino acids. Longer peptides may comprise multiple copies of one or more of the C-peptide sequences, such as any of SEQ. ID. Nos. 1-33. Insertional amino acid sequence variants are those in which one or more amino acid residues are introduced at a site in the protein. Deletional variants are characterized by the removal of one or more amino acids from the sequence. Variants may include, e.g., different allelic variants as they appear in nature, e.g., in other species or due to geographical variation. All such variants, derivatives, fusion proteins, or fragments of C-peptide are included, may be used in any of the methods, claims, or pharmaceutical compositions disclosed herein, and are subsumed under the term "C-peptide".

The PEGylated forms of C-peptide, C-peptide variants, derivatives, and fragments thereof are functionally equivalent in that they have detectable C-peptide activity. More particularly, they exhibit at least about 1%, at least about 5%, at least about 10%, at least about 15%, at least about 20%, at least about 30%, at least about 40%, at least about 50%, at least about 60%, at least about 70%, at least about 80%, at least about 90%, at least about 100%, or higher than 100% of the activity of native proinsulin C-peptide, particularly human C-peptide. Thus, they are capable of functioning as proinsulin C-peptide, i.e., can substitute for C-peptide itself. Such activity means any activity exhibited by a native C-peptide, whether a physiological response exhibited in an in vivo or in vitro test system, or any biological activity or reaction mediated by a native C-peptide, e.g., in an enzyme assay or in binding to test tissues, membranes, or metal ions. Thus, it is known that C-peptide causes an influx of calcium and initiates a range of intracellular signalling cascades such as phosphorylation of the MAP-kinase pathway including phosphorylation of ERK 1 and 2, CREB, PKC, GSK3, PI3K, NF-kappaB, and PPARgamma, resulting in an increased expression of eNOS, Na+K+ATPase and a wide range of transcription factors. An assay for C-peptide activity can thus be made by assaying for the activation or up-regulation of any of these pathways upon addition or administration of the peptide (e.g., fragment or derivative) in question to cells from relevant target tissues including endothelial, kidney, fibroblast and immune cells. Such assays are described in, e.g., Ohtomo Y et al. (*Diabetologia* 39: 199-205, (1996)), Kunt T et al. (*Diabetologia* 42(4): 465-471, (1999)), Shafqat J et al. (*Cell Mol. Life. Sci.* 59: 1185-1189, (2002)). Kitamura T et al. (*Biochem. J.* 355: 123-129, (2001)), Hills and Brunskill (Exp Diab Res 2008), as described in WO 98/13384 or in Ohtomo Y et al. (supra) or Ohtomo Y et al. (*Diabetologia* 41: 287-291, (1998)). An assay for C-peptide activity based on endothelial nitric oxide synthase (eNOS) activity is also described in Kunt T et al. (supra) using bovine aortic cells and a reporter cell assay. Binding to particular cells may also be used to assess or assay for C-peptide activity, e.g., to cell membranes from human renal tubular cells, skin fibroblasts, and saphenous vein endothelial cells using fluorescence correlation spectroscopy, as described, e.g., in Rigler R et al. (*PNAS USA* 96: 13318-13323, (1999)), Henriksson M et al. (*Cell Mol. Life. Sci.* 57: 337-342, (2000)) and Pramanik A et al. (*Biochem Biophys. Res. Commun.* 284: 94-98, (2001)).

In another aspect of any of the claimed PEGylated C-peptides, the PEGylated C-peptide has a plasma or sera pharmacokinetic AUC profile at least about 5-fold greater than unmodified C-peptide when subcutaneously administered to a mammal.

In another aspect of any of the claimed PEGylated C-peptides, the PEGylated C-peptide has a plasma or sera pharmacokinetic AUC profile at least about 6-fold greater than unmodified C-peptide when subcutaneously administered to a mammal.

In another aspect of any of the claimed PEGylated C-peptides, the PEGylated C-peptide has a plasma or sera pharmacokinetic AUC profile at least about 7-fold greater than unmodified C-peptide when subcutaneously administered to a mammal.

In another aspect of any of the claimed PEGylated C-peptides, the PEGylated C-peptide has a plasma or sera pharmacokinetic AUC profile at least about 8-fold greater than unmodified C-peptide when subcutaneously administered to a mammal.

In another aspect of any of the claimed PEGylated C-peptides, the PEGylated C-peptide has a plasma or sera pharmacokinetic AUC profile at least about 10-fold greater than unmodified C-peptide when subcutaneously administered to a mammal.

In another aspect of any of the claimed PEGylated C-peptides, the PEGylated C-peptide has a plasma or sera pharmacokinetic AUC profile at least about 15-fold greater than unmodified C-peptide when subcutaneously administered to a mammal.

In another aspect of any of the claimed PEGylated C-peptides, the PEGylated C-peptide has a plasma or sera pharmacokinetic AUC profile at least about 20-fold greater than unmodified C-peptide when subcutaneously administered to a mammal.

In another aspect of any of the claimed PEGylated C-peptides, the PEGylated C-peptide has a plasma or sera pharmacokinetic AUC profile at least about 25-fold greater than unmodified C-peptide when subcutaneously administered to a mammal.

In another aspect of any of the claimed PEGylated C-peptides, the PEGylated C-peptide has a plasma or sera pharmacokinetic AUC profile at least about 50-fold greater than unmodified C-peptide when subcutaneously administered to a mammal.

In another aspect of any of the claimed PEGylated C-peptides, the PEGylated C-peptide has a plasma or sera pharmacokinetic AUC profile at least about 75-fold greater than unmodified C-peptide when subcutaneously administered to a mammal.

In another aspect of any of the claimed PEGylated C-peptides, the PEGylated C-peptide has a plasma or sera pharmacokinetic AUC profile at least about 100-fold greater than unmodified C-peptide when subcutaneously administered to a mammal.

In one aspect the mammal is a dog. In one aspect the mammal is a rat. In one aspect the mammal is a human.

V. C-peptide and PEGylated C-peptide Production

C-peptide may be produced synthetically using standard solid-phase peptide synthesis, or by recombinant technology, e.g., as a by-product in the production of human insulin from human proinsulin, or using genetically modified host (see generally WO 1999007735; Jonasson P, et al., *J Biotechnol.* (2000) 76(2-3):215-26; Jonasson P, et al., *Gene* (1998);210 (2):203-10; Li S X, Tian et al., Sheng Wu Hua Xue Yu Sheng Wu Wu Li Xue Bao (Shanghai) (2003) 35(11):986-92; Nilsson J, et al., *J Biotechnol.* (1996) 48(3):241-50; Huang Y B, et al., *Acta Biochim Biophys Sin* (Shanghai) (2006) 38(8):586-92).

In an alternative approach to direct coupling to the N-terminus, the PEG reagent, or a lysine residue, may be incorporated at a desired position of the C-peptide during peptide synthesis. In this way, site-selective introduction of one or more PEGs can be achieved. See, e.g., International Patent Publication No. WO 95/00162, which describes the site selective synthesis of conjugated peptides.

C-peptide can be produced by expressing a DNA sequence encoding the C-peptide in question in a suitable host cell by well known techniques used for insulin biosynthesis as disclosed in, e.g., U.S. Pat. No. 6,500,645. The C-peptide may be expressed directly, or as a multimerized construct to increase the yield of product as disclosed in U.S. Pat. No. 6,558,924. The multimerized product is cleaved in vitro after isolation from the culture broth.

The polynucleotide sequence coding for the C-peptide may be prepared synthetically by established standard methods, e.g., the phosphoamidite method described by Beaucage et al. (1981) *Tetrahedron Letters* 22:1859-1869, or the method described by Matthes et al. (1984) *EMBO Journal* 3:801-805. According to the phosphoramidite method, oligonucleotides are synthesized, e.g., in an automatic DNA synthesizer, purified, duplexed and ligated to form the synthetic DNA construct. A currently preferred way of preparing the DNA construct is by polymerase chain reaction (PCR).

The polynucleotide sequences may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The recombinant method will typically make use of a vector which is capable of replicating in the selected microorganism or host cell and which carries a polynucleotide sequence encoding the parent single-chain insulin of the invention. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

The recombinant expression vector is capable of replicating in yeast. Examples of sequences which enable the vector to replicate in yeast are the yeast plasmid 2 pm replication genes REP 1-3 and origin of replication. The vector may contain one or more selectable markers which permit easy selection of transformed cells. A selectable marker is a gene the product of which provides for biocide or viral resistance, resistance to heavy metals, prototroph to auxotroph, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyl-transferase), pyrG (orotidine-5'-phosphate decarboxylase) and trpC (anthranilate synthase. Suitable markers for yeast host cells are ADE2, H153, LEU2, LYS2, MET3, TRP1, and URA3. A well-suited selectable marker for yeast is the *Schizosaccharomyces* pompe TPI gene (Russell (1985) *Gene* 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intracellular polypeptides either homologous or heterologous to the host cell.

Examples of suitable promoters for directing the transcription in a bacterial host cell are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Mal, TPI, ADH, or PGK promoters. The polynucleotide sequence encoding the C-peptide of the invention will also typically be operably connected to a suitable terminator. In yeast a suitable terminator is the TPI terminator (Alber et al. (1982) *J. Mol. Appl. Genet.* 1:419-434).

The procedures used to ligate the polynucleotide sequence encoding the parent single-chain insulin of the invention, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the single-chain insulins of the invention, and subsequently inserting this fragment into a suitable expression vector, or by sequentially inserting DNA fragments encoding genetic information for the individual elements followed by ligation.

The vector comprising the polynucleotide sequence encoding the C-peptide of the invention is introduced into a host cell so that the vector is maintained as a chromosomal integrant or as a self-replicating extra-chromosomal vector. The term "host cell" encompasses any progeny of a parent cell that is not identical to the parent cell due to mutations that occur during replication. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, Streptomyces cell, or gram negative bacteria such as *E. coli* and *Pseudomonas* sp. Eukaryote cells may be mammalian, insect, plant, or fungal cells. In one embodiment, the host cell is a yeast cell. The yeast organism may be any suitable yeast organism which, on cultivation, produces large amounts of the single chain insulin of the invention. Examples of suitable yeast organisms are strains selected from the yeast species *Saccharomyces cerevisiae, Saccharomyces kluyveri, Schizosaccharomyces pombe, Sacchoromyces uvarum, Kluyvero-myces lactis, Hansenula polymorpha, Pichia pastoris, Pichia methanolica, Pichia kluyveri, Yarrowia ilpolytica, Candida* sp., *Candida utilis, Candida cacaoi, Geotrichum* sp., and *Geotrichum fermentans*.

The transformation of the yeast cells may for instance be effected by protoplast formation followed by transformation in a manner known per se. The medium used to cultivate the cells may be any conventional medium suitable for growing yeast organisms. The secreted single-chain insulin, a significant proportion of which will be present in the medium in correctly processed form, may be recovered from the medium by conventional procedures including separating the yeast cells from the medium by centrifugation, filtration or catching the insulin precursor by an ion exchange matrix or by a reverse phase absorption matrix, precipitating the proteinaceous components of the supernatant or filtrate by means of a salt, e.g., ammonium sulphate, followed by purification by a variety of chromatographic procedures, e.g., ion exchange chromatography, affinity chromatography, or the like.

VI. Methods of Use

In one aspect, the present invention includes a method for maintaining C-peptide levels above the minimum effective therapeutic level in a patient in need thereof, comprising administering to the patient a therapeutic dose of any of the claimed PEGylated C-peptides.

In another aspect, the present invention includes a method for treating one or more long-term complications of diabetes in a patient in need thereof, comprising administering to the patient a therapeutic dose of any of the claimed PEGylated C-peptides.

In another aspect, the present invention includes a method for treating a patient with diabetes comprising administering to the patient a therapeutic dose of any of the claimed PEGylated C-peptides in combination with insulin.

In another aspect, the present invention includes any of the claimed PEGylated C-peptides for use as a C-peptide replacement therapy or dose in a patient in need thereof.

In broad terms, diabetes refers to the situation where the body either fails to properly respond to its own insulin, does not make enough insulin, or both. The primary result of impaired insulin production is the accumulation of glucose in the blood, and a C-peptide deficiency leading to various short- and long-term complications. Three principal forms of diabetes exist:

Type 1: Results from the body's failure to produce insulin and C-peptide. It is estimated that 5-10% of Americans who are diagnosed with diabetes have type 1 diabetes. Presently almost all persons with type 1 diabetes must take insulin injections. The term "type 1 diabetes" has replaced several former terms, including childhood-onset diabetes, juvenile diabetes, and insulin-dependent diabetes mellitus (IDDM). For patients with type 1 diabetes, basal levels of C-peptide are typically less than about 0.20 nM (Ludvigsson et al.: *New Engl. J. Med.* 359: 1909-1920, (2008)).

Type 2: Results from tissue insulin resistance, a condition in which cells fail to respond properly to insulin, sometimes combined with relative insulin deficiency. The term "type 2 diabetes" has replaced several former terms, including adult-onset diabetes, obesity-related diabetes, and non-insulin-dependent diabetes mellitus (NIDDM). For type 2 patients in the basal state, C-peptide levels of about 0.8 nM (range 0.64 to 1.56 nM), and glucose stimulated levels of about 5.7 nM (range 3.7 to 7.7 nM) have been reported. (Retnakaran R et al.: *Diabetes Obes. Metab.* (2009) DOI 10.11 111/j.1463-1326.2009.01129.x; Zander et al.: *Lancet* 359: 824-830, (2002)).

In addition to type 1 and type 2 diabetics, there is increasing recognition of a subclass of diabetes referred to as latent autoimmune diabetes in the adult (LADA) or late-onset autoimmune diabetes of adulthood, or "slow onset type 1" diabetes, and sometimes also "type 1.5" or "type one-and-a-half" diabetes. In this disorder, diabetes onset generally occurs in ages 35 and older, and antibodies against components of the insulin-producing cells are always present, demonstrating that autoimmune activity is an important feature of LADA. It is primarily antibodies against glutamic acid decarboxylase (GAD) that are found. Some LADA patients show a phenotype similar to that of type 2 patients with increased body mass index (BMI) or obesity, insulin resistance, and abnormal blood lipids. Genetic features of LADA are similar to those for both type 1 and type 2 diabetes. During the first 6-12 months after debut the patients may not require insulin administration and they are able to maintain relative normoglycemia via dietary modification and/or oral anti-diabetic medication. However, eventually all patients become insulin dependent, probably as a consequence of progressive autoimmune activity leading to gradual destruction of the pancreatic islet β-cells. At this stage the LADA patients show low or absent levels of endogenous insulin and C-peptide, and they are prone to develop long-term complications of diabetes involving the peripheral nerves, the kidneys, or the eyes similar to type 1 diabetes patients and thus become candidates for C-peptide therapy (Palmer et al.: Diabetes 54(suppl 2): S62-67, (2005); Desai et al.: *Diabetic Medicine* 25(suppl 2): 30-34, (2008); Fourlanos et al.: *Diabetologia* 48: 2206-2212, (2005)).

Gestational diabetes: Pregnant women who have never had diabetes before but who have high blood sugar (glucose) levels during pregnancy are said to have gestational diabetes. Gestational diabetes affects about 4% of all pregnant women. It may precede development of type 2 (or rarely type 1) diabetes.

Several other forms of diabetes mellitus are categorized separately from these. Examples include congenital diabetes due to genetic defects of insulin secretion, cystic fibrosis-related diabetes, steroid diabetes induced by high doses of glucocorticoids, and several forms of monogenic diabetes.

Accordingly in any of these methods, the term "patient" refers to an individual who has one or more of the symptoms of any of diabetes. In one aspect of any of these methods, the term "patient" refers to an individual who has one or more of the symptoms of any of insulin-dependent diabetes. In one aspect of any of these methods, the term "patient" refers to an individual who has one or more of the symptoms of any of type 2 diabetes. In one aspect of any of these methods, the term "patient" refers to an individual who has one or more of the symptoms of LADA. In one aspect of any of these methods, the term "patient" refers to an individual who has one or more of the symptoms of gestational diabetes. Accordingly in one aspect of any of these methods, the term "patient" refers to an individual who has a fasting C-peptide level of less than about 0.4 nM. In another aspect of any of these methods, the term "patient" refers to an individual who has a fasting C-peptide level of less than about 0.2 nM.

Acute complications of diabetes include hypoglycemia, diabetic ketoacidosis, or nonketotic hyperosmolar coma that may occur if the disease is not adequately controlled. Serious long-term complications can also occur, and are discussed in more detail below.

In another aspect, the present invention includes a method for treating one or more long-term complications of diabetes in a patient in need thereof, comprising administering to the patient a therapeutic dose of any of the claimed PEGylated C-peptides.

In another aspect, the present invention includes a method for treating a patient with diabetes comprising administering to the patient a therapeutic dose of any of the claimed PEGylated C-peptides in combination with insulin.

In this context "in combination" means: 1) part of the same unitary dosage form; 2) administration separately, but as part of the same therapeutic treatment program or regimen, typically but not necessarily, on the same day. In one aspect, any of the claimed PEGylated C-peptides may be administered at a fixed daily dosage, and the insulin taken on an as needed basis.

In another aspect, the present invention includes any of the claimed PEGylated C-peptides for use for treating one or more long-term complications of diabetes in a patient in need thereof.

In any of these methods, the terms "long-term complication of type 1 diabetes", or "long-term complications of diabetes" refers to the long-term complications of impaired glycemic control, and C-peptide deficiency associated with insulin-dependent diabetes. Typically long-term complications of type 1 diabetes are associated with type 1 diabetics. However the term can also refer to long-term complications of diabetes that arise in type 1.5 and type 2 diabetic patients who develop a C-peptide deficiency as a consequence of losing pancreatic islet β-cells and therefore also become insulin dependent. In broad terms, many such complications arise from the primary damage of blood vessels (angiopathy), resulting in subsequent problems that can be grouped under "microvascular disease" (due to damage to small blood vessels) and "macrovascular disease" (due to damage to the arteries).

Specific diseases and disorders included within the term long-term complications of diabetes include, without limitation; retinopathy including early stage retinopathy with microaneurysms, proliferative retinopathy, and macular edema; peripheral neuropathy including sensorimotor polyneuropathy, painful sensory neuropathy, acute motor neuropathy, cranial focal and multifocal polyneuropathies, thoracolumbar radiculoneuropathies, proximal diabetic neuropathies, and focal limb neuropathies including entrapment and compression neuropathies; autonomic neuropathy involving the cardiovascular system, the gastrointestinal tract, the respiratory system, the urigenital system, sudomotor function and papillary function; and nephropathy including disorders with microalbuminuria, overt proteinuria, and end-stage renal disease.

Impaired microcirculatory perfusion appears to be crucial to the pathogenesis of both neuropathy and retinopathy in diabetics. This in turn reflects a hyperglycemia-mediated perturbation of vascular endothelial function that results in: overactivation of protein kinase C, reduced availability of nitric oxide (NO), increased production of superoxide and endothelin-1 (ET-1), impaired insulin function, diminished synthesis of prostacyclin/PGE1, and increased activation and endothelial adherence of leukocytes. This is ultimately a catastrophic group of clinical events.

Accordingly in some embodiments, the term "patient" refers to an individual who has one or more of the symptoms of the long-term complications of diabetes.

Diabetic retinopathy is an ocular manifestation of the systemic damage to small blood vessels leading to microangiopathy. In retinopathy, growth of friable and poor-quality new blood vessels in the retina as well as macular edema (swelling of the macula) can lead to severe vision loss or blindness. As new blood vessels form at the back of the eye as a part of proliferative diabetic retinopathy (PDR), they can bleed (hemorrhage) and blur vision. It affects up to 80% of all patients who have had diabetes for 10 years or more.

The symptoms of diabetic retinopathy are often slow to develop and subtle and include blurred version and progressive loss of sight. Macular edema, which may cause vision loss more rapidly, may not have any warning signs for some time. In general, however, a person with macular edema is likely to have blurred vision, making it hard to do things like read or drive. In some cases, the vision will get better or worse during the day.

Accordingly in some embodiments, the term "patient" refers to an individual who has one of more of the symptoms of diabetic retinopathy.

Diabetic neuropathies are neuropathic disorders that are associated with diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy.

Diabetic neuropathy affects all peripheral nerves: pain fibers, motor neurons, autonomic nerves. It therefore necessarily can affect all organs and systems since all are innervated. There are several distinct syndromes based on the organ systems and members affected, but these are by no means exclusive. A patient can have sensorimotor and autonomic neuropathy or any other combination. Symptoms vary depending on the nerve(s) affected and may include symptoms other than those listed. Symptoms usually develop gradually over years.

Symptoms of diabetic neuropathy may include: numbness and tingling of extremities, dysesthesia (decreased or loss of sensation to a body part), diarrhea, erectile dysfunction, urinary incontinence (loss of bladder control), impotence, facial, mouth and eyelid drooping, vision changes, dizziness, muscle weakness, difficulty swallowing, speech impairment, fasciculation (muscle contractions), anorgasmia, and burning or electric pain.

Additionally, different nerves are affected in different ways by neuropathy. Sensorimotor polyneuropathy, in which longer nerve fibers are affected to a greater degree than shorter ones, because nerve conduction velocity is slowed in proportion to a nerve's length. In this syndrome, decreased sensation and loss of reflexes occurs first in the toes on each foot, then extends upward. It is usually described as glove-stocking distribution of numbness, sensory loss, dysesthesia, and night-time pain. The pain can feel like burning, pricking sensation, achy, or dull. Pins and needles sensation is common. Loss of proprioception, the sense of where a limb is in space, is affected early. These patients cannot feel when they are stepping on a foreign body, like a splinter, or when they are developing a callous from an ill-fitting shoe. Consequently, they are at risk for developing ulcers and infections on the feet and legs, which can lead to amputation. Similarly, these patients can get multiple fractures of the knee, ankle, or foot, and develop a Charcot joint. Loss of motor function results in dorsiflexion, contractures of the toes, loss of the interosseous muscle function, and leads to contraction of the digits, so called hammer toes. These contractures occur not only in the foot, but also in the hand where the loss of the musculature makes the hand appear gaunt and skeletal. The loss of muscular function is progressive.

Autonomic neuropathy impacts the autonomic nervous system serving the heart, gastrointestinal system, and genitourinary system. The most commonly recognized autonomic dysfunction in diabetics is orthostatic hypotension, or fainting when standing up. In the case of diabetic autonomic neuropathy, it is due to the failure of the heart and arteries to appropriately adjust heart rate and vascular tone to keep blood continually and fully flowing to the brain. This symptom is usually accompanied by a loss of the usual change in heart rate seen with normal breathing. These two findings suggest autonomic neuropathy.

Gastrointestinal system symptoms include delayed gastric emptying, gastroparesis, nausea, bloating, and diarrhea. Because many diabetics take oral medication for their diabetes, absorption of these medicines is greatly affected by the delayed gastric emptying. This can lead to hypoglycemia when an oral diabetic agent is taken before a meal and does not get absorbed until hours, or sometimes days later, when there is normal or low blood sugar already. Sluggish movement of the small intestine can cause bacterial overgrowth, made worse by the presence of hyperglycemia. This leads to bloating, gas, and diarrhea.

Genitourinary system symptoms include urinary frequency, urgency, incontinence, and retention. Urinary retention can lead to bladder diverticula, stones, reflux nephropathy, and frequent urinary tract infections. Accordingly in any of these methods, the term "patient" refers to an individual who has one of more of the symptoms of autonomic neuropathy.

Accordingly in some embodiments, the term "patient" refers to an individual who has one of more of the symptoms of diabetic neuropathy. In another aspect of any of these methods, the patient has "established peripheral neuropathy" which is characterized by reduced sensory nerve conduction velocity (SCV) in the sural nerves (less than −1.5 SD from a body height-corrected reference value for a matched normal individual). In certain embodiments, the term "patient" refers to an individual who has one of more of the symptoms of incipient neuropathy.

Accordingly in certain embodiments, the current invention includes a method of treating or preventing a decrease in a subject's, or patient's, height-adjusted sensory or motor nerve conduction velocity. In one aspect of this method, the motor nerve conduction velocity is initial nerve conduction velocity. In another embodiment, the motor nerve conduction velocity is the peak nerve conduction velocity.

In certain embodiments the subject is a patient with diabetes. In certain embodiments, the subject has at least one long term complication of diabetes. In one aspect, the patient exhibits a peak nerve conduction velocity that is at least about 2 standard deviations from the mean peak nerve conduction velocity for a similar height-matched subject group. In one aspect, the patients have a peak nerve conduction velocity of greater than about 35 m/s. In one aspect of any of the claimed methods, the patients have a peak nerve conduction velocity of greater than about 40 m/s. In one aspect, the patients have a peak nerve conduction velocity of greater than about 45 m/s. In one aspect, the patients have a peak nerve conduction velocity of greater than about 50 m/s.

In one aspect of any of the claimed methods, treatment results in an improvement in nerve conduction velocity of at least about 1.5 m/s. In another aspect of these methods, treatment results in an improvement in nerve conduction velocity of at least about 2.0 m/s. In another aspect of these methods, treatment results in an improvement in nerve conduction velocity of at least about 2.5 m/s. In another aspect of these methods, treatment results in an improvement in nerve conduction velocity of at least about 3.0 m/s. In another aspect of these methods, treatment results in an improvement in nerve conduction velocity of at least about 3.5 m/s. In another aspect of these methods, treatment results in an improvement in nerve conduction velocity of at least about 4.0 m/s. In another aspect of these methods, treatment results in an improvement in nerve conduction velocity of at least about 4.5 m/s. In another aspect of these methods, treatment results in an improvement in nerve conduction velocity of at least about 5.0 m/s. In another aspect of these methods, treatment results in an improvement in nerve conduction velocity of at least about 5.5 m/s. In another aspect of these methods, treatment results in an improvement in nerve conduction velocity of at least about 6.0 m/s. In another aspect of these methods, treatment results in an improvement in nerve conduction velocity of at least about 7.0 m/s. In another aspect of these methods, treatment results in an improvement in nerve conduction velocity of at least about 8.0 m/s. In another aspect of these methods, treatment results in an improvement in nerve conduction velocity of at least about 9.0 m/s. In another aspect of these methods, treatment results in an improvement in nerve conduction velocity of at least about 10.0 m/s. In another aspect of these methods, treatment results in an improvement in nerve conduction velocity of at least about 15.0 m/s. In another aspect of these methods, treatment results in an improvement in nerve conduction velocity of at least about 20.0 m/s.

In certain embodiments, of any of these methods, treatment results in an improvement of at least 10% in peak nerve conduction velocity compared to peak nerve conduction velocity prior to starting PEGylated C-peptide therapy. In certain embodiments, of any of these methods, treatment results in an improvement of at least 15% in peak nerve conduction velocity compared to peak nerve conduction velocity prior to starting PEGylated C-peptide therapy. In certain embodiments, of any of these methods, treatment results in an improvement of at least 20% in peak nerve conduction velocity compared to peak nerve conduction velocity prior to starting PEGylated C-peptide therapy. In certain embodiments, of any of these methods, treatment results in an improvement of at least 25% in peak nerve conduction velocity compared to peak nerve conduction velocity prior to starting PEGylated C-peptide therapy. In certain embodiments, of any of these methods, treatment results in an improvement of at least 30% in peak nerve conduction velocity compared to peak nerve conduction velocity prior to starting PEGylated C-peptide therapy. In certain embodiments, of any of these methods, treatment results in an improvement of at least 40% in peak nerve conduction velocity compared to peak nerve conduction velocity prior to starting PEGylated C-peptide therapy. In certain embodiments, of any of these methods, treatment results in an improvement of at least 50% in peak nerve conduction velocity compared to peak nerve conduction velocity prior to starting PEGylated C-peptide therapy.

Diabetic nephropathy is a progressive kidney disease caused by angiopathy of capillaries in the kidney glomeruli. It is characterized by nephrotic syndrome and diffuse glomerulosclerosis. It is due to long-standing diabetes mellitus, and is a prime cause for dialysis in many Western countries.

The symptoms of diabetic nephropathy can be seen in patients with chronic diabetes (15 years or more after onset). The disease is progressive and is more frequent in men. Diabetic nephropathy is the most common cause of chronic kidney failure and end-stage kidney disease in the United States. People with both type 1 and type 2 diabetes are at risk. The risk is higher if blood-glucose levels are poorly controlled. Further, once nephropathy develops, the greatest rate of progression is seen in patients with poor control of their blood pressure. Also people with high cholesterol level in their blood have much more risk than others.

The earliest detectable change in the course of diabetic nephropathy is an abnormality of the glomerular filtration barrier. At this stage, the kidney may start allowing more serum albumin than normal in the urine (albuminuria), and this can be detected by sensitive medical tests for albumin. This stage is called "microalbuminuria". As diabetic nephropathy progresses, increasing numbers of glomeruli are destroyed by nodular glomerulosclerosis. Now the amounts of albumin being excreted in the urine increases, and may be detected by ordinary urinalysis techniques. At this stage, a kidney biopsy clearly shows diabetic nephropathy.

Kidney failure provoked by glomerulosclerosis leads to fluid filtration deficits and other disorders of kidney function. There is an increase in blood pressure (hypertension) and fluid retention in the body plus a reduced plasma oncotic pressure causes edema. Other complications may be arteriosclerosis of the renal artery and proteinuria.

Throughout its early course, diabetic nephropathy has no symptoms. They develop in late stages and may be a result of excretion of high amounts of protein in the urine or due to renal failure. Symptoms include, edema; swelling, usually around the eyes in the mornings; later, general body swelling may result, such as swelling of the legs, foamy appearance or excessive frothing of the urine (caused by the proteinura), unintentional weight gain (from fluid accumulation), anorexia (poor appetite), nausea and vomiting, malaise (general ill feeling), fatigue, headache, frequent hiccups, and generalized itching.

Accordingly in some embodiments, the term "patient" refers to an individual who has one of more of the symptoms of diabetic nephropathy.

Diabetic cardiomyopathy (DCM), damage to the heart, leading to diastolic dysfunction and eventually heart failure. Aside from large vessel disease and accelerated atherosclerosis, which is very common in diabetes, DCM is a clinical condition diagnosed when ventricular dysfunction develops in patients with diabetes in the absence of coronary atherosclerosis and hypertension. DCM may be characterized functionally by ventricular dilation, myocyte hypertrophy, prominent interstitial fibrosis, and decreased or preserved systolic function in the presence of a diastolic dysfunction.

One particularity of DCM is the long latent phase, during which the disease progresses but is completely asymptomatic. In most cases, DCM is detected with concomitant hypertension or coronary artery disease. One of the earliest signs is mild left ventricular diastolic dysfunction with little effect on ventricular filling. Also, the diabetic patient may show subtle signs of DCM related to decreased left ventricular compliance or left ventricular hypertrophy or a combination of both. A prominent "a" wave can also be noted in the jugular venous pulse, and the cardiac apical impulse may be overactive or sustained throughout systole. After the development of systolic dysfunction, left ventricular dilation and symptomatic heart failure, the jugular venous pressure may become elevated and the apical impulse would be displaced downward and to the left. Systolic mitral murmur is not uncommon in these cases. These changes are accompanied by a variety of electrocardiographic changes that may be associated with DCM in 60% of patients without structural heart disease, although usually not in the early asymptomatic phase. Later in the progression, a prolonged QT interval may be indicative of fibrosis. Given that the definition of DCM excludes concomitant atherosclerosis or hypertension, there are no changes in perfusion or in atrial natriuretic peptide levels up until the very late stages of the disease, when the hypertrophy and fibrosis become very pronounced.

In certain embodiments, the term "patient" refers to an individual who has one of more of the symptoms of diabetic cardiomyopathy.

Macrovascular diseases of diabetes include coronary artery disease, leading to angina or myocardial infarction ("heart attack"), stroke (mainly the ischemic type), peripheral vascular disease, which contributes to intermittent claudication (exertion-related leg and foot pain), as well as diabetic foot and diabetic myonecrosis ("muscle wasting").

In certain embodiments, the term "patient" refers to an individual who has one or more of the symptoms of a macrovascular disease of diabetes.

Methods for Preventing Hypoglycemia.

In certain embodiments, the present invention includes the use of any of the disclosed PEGylated C-peptides to reduce the risk of hypoglycemia in a human patient with insulin dependent diabetes, in a regimen which additionally comprises the administration of insulin, comprising; a) administering insulin to said patient; b) administering a therapeutic dose of PEGylated C-peptide in a different site as that used for said patient's insulin administration; c) adjusting the dosage amount, type, or frequency of insulin administered based on said patient's altered insulin requirements resulting from said therapeutic dose of PEGylated C-peptide.

In another aspect, the present invention includes a method of reducing insulin usage in an insulin-dependent human patient, comprising the steps of; a) administering insulin to said patient; b) administering subcutaneously to said patient a therapeutic dose of any of the disclosed PEGylated C-peptides in a different site as that used for said patient's insulin administration; c) adjusting the dosage amount, type, or frequency of insulin administered based on monitoring said patient's altered insulin requirements resulting from said therapeutic dose of PEGylated C-peptide, wherein said adjusted dose of insulin does not induce hyperglycemia, wherein said adjusted dose of insulin is at least 10% less than said patient's insulin dose prior to starting PEGylated C-peptide. (See for example U.S. Pat. No. 7,855,177, which is herein incorporated by reference).

In any of these methods, the term "hypoglycemia" or "hypoglycemic events" refers to all episodes of abnormally low plasma glucose concentration that exposes the patient to potential harm. The American Diabetes Association Workgroup has recommended that people with insulin-dependent diabetes become concerned about the possibility of developing hypoglycemia at a plasma glucose concentration of less than 70 mg/dL (3.9 mmoL/L). Accordingly in one aspect of any of the claimed methods, the terms hypoglycemia or hypoglycemic event refers to the situation where the plasma glucose concentration of the patient drops to less than about 70 mg/dL (3.9 mmoL/L).

Hypoglycemia is a serious medical complication in the treatment of diabetes, and causes recurrent morbidity in most people with type 1 diabetes and many with advanced type 2 diabetes and is sometimes fatal. In addition, hypoglycemia compromises physiological and behavioral defenses against subsequent falling plasma glucose concentrations and thus causes a vicious cycle of recurrent hypoglycemia. Accordingly the prevention of hypoglycemia is of significant importance in the treatment of diabetes, as well as the treatment of the long-term complications of diabetes.

Unfortunately hypoglycemia is a fact of life for most people with type 1 diabetes (Cryer P E et al.: *Diabetes* 57: 3169-3176, (2008)). The average patient has untold numbers of episodes of asymptomatic hypoglycemia and suffers two episodes of symptomatic hypoglycemia per week, with thousands of such episodes over a lifetime of diabetes. He or she suffers one or more episodes of severe, temporarily disabling hypoglycemia often with seizure or coma, per year.

Overall, hypoglycemia is less frequent in type 2 diabetes; however, the risk of hypoglycemia becomes progressively more frequent and limiting to glycemic control later in the course of type 2 diabetes. The prospective, population-based data of Donnelly et al. (*Diabetes Med.* 22: 749-755, (2005)) indicate that the overall incidence of hypoglycemia in insulin-treated type 2 diabetes is approximately one third of that in type 1 diabetes. The incidence of any hypoglycemia and of severe hypoglycemia was 4,300 and 115 episodes per 100 patient years, respectively, in type 1 diabetes and 1600 and 35 episodes per 100 patient years, respectively, in insulin-treated type 2 diabetes.

Hypoglycemia may be classified based on the severity of the hypoglycemic event. For example, the American Diabetes Association Workgroup has suggested the following classification of hypoglycemia in diabetes: 1) severe hypoglycemia (i.e., hypoglycemic coma requiring assistance of another person); 2) documented symptomatic hypoglycemia (with symptoms and a plasma glucose concentration of less than 70 mg/dL); 3) asymptomatic hypoglycemia (with a plasma glucose concentration of less than 70 mg/dL without symptoms); 4) probable symptomatic hypoglycemia (with symptoms attributed to hypoglycemia, but without a plasma glucose measurement); and 5) relative hypoglycemia (with a plasma glucose concentration of greater than 70 mg/dL but falling towards that level).

Thus in another aspect of any of the methods disclosed herein, the term "hypoglycemia" refers to severe hypoglycemia, and/or hypoglycemic coma. In another aspect of any of these methods, the term "hypoglycemia" refers to symptomatic hypoglycemia. In another aspect of any of these methods, the term "hypoglycemia" refers to probable symptomatic hypoglycemia. In another aspect of any of these methods, the term "hypoglycemia" refers to asymptomatic hypoglycemia. In another aspect of any of these methods, the term "hypoglycemia" refers to relative hypoglycemia.

Insulin Types and Administration Forms

There are over 180 individual insulin preparations available worldwide which have been developed to provide different lengths of activity (activity profiles). Approximately 25% of these are soluble insulin (unmodified form); about 35% are long- or intermediate-acting basal insulins (mixed with NPH [neutral protamine Hagedorn] insulin or Lente insulin [insulin zinc suspension], or forms that are modified to have an increased isoelectric point [insulin glargine], or acylation [insulin detemir]; these forms have reduced solubility, slow subcutaneous absorption, and long duration of action relative to soluble insulins); about 2% are rapid-acting insulins (e.g., which are engineered by amino acid change, and have reduced self-association and increased subcutaneous absorption); and about 38% are pre-mixed insulins (e.g., mixtures of short-, intermediate-, and long-acting insulins; these preparations have the benefit of a reduced number of daily injections).

Short-acting insulin preparations that are commercially available in the US include regular insulin and rapid-acting insulins. Regular insulin has an onset of action of 30-60 minutes, peak time of effect of 1.5 to 2 hours, and duration of activity of 5 to 12 hours. Rapid-acting insulins, such as Aspart (Novo Rapid), Lispro (HUMALOG®), and Glulisine (APIDRA®), have an onset of action of 10-30 minutes, peak time of effect of around 30 minutes, and a duration of activity of 3 to 5 hours.

Intermediate-acting insulins, such as NPH and Lente insulins, have an onset of action of 1 to 2 hours, peak time of effect of 4 to 8 hours, and a duration of activity of 10 to 20 hours.

Long-acting insulins, such as ULTRALENTE® insulin, have an onset of action of 2 to 4 hours, peak time of effect of 8 to 20 hours, and a duration of activity of 16 to 24 hours. Other examples of long-acting insulins include Glargine and Determir. Glargine insulin has an onset of action of 1 to 2 hours, and a duration of action of 24 hours, but with no peak effect.

In many cases, regimens that use insulin in the management of diabetes combine long-acting and short-acting insulin. For example, LANTUS®, from Aventis Pharmaceuticals Inc., is a recombinant human insulin analog that is a long-acting, parenteral blood-glucose-lowering agent whose longer duration of action (up to 24 hours) is directly related to its slower rate of absorption. LANTUS® is administered subcutaneously once a day, preferably at bedtime, and is said to provide a continuous level of insulin, similar to the slow, steady (basal) secretion of insulin provided by the normal pancreas. The activity of such a long-acting insulin results in a relatively constant concentration/time profile over 24 hours with no pronounced peak, thus allowing it to be administered once a day as a patient's basal insulin. Such long-acting insulin has a long-acting effect by virtue of its chemical composition, rather than by virtue of an addition to insulin when administered.

More recently automated wireless controlled systems for continuous infusion of insulin, such as the system sold under the trademark OMNIPOD™ Insulin Management System (Insulet Corporation, Bedford, Mass.) have been developed. These systems provide continuous subcutaneous insulin delivery with blood glucose monitoring technology in a discreet two-part system. This system eliminates the need for daily insulin injections, and does not require a conventional insulin pump which is connected via tubing.

OMNIPOD™ is a small lightweight device that is worn on the skin like an infusion set. It delivers insulin according to pre-programmed instructions transmitted wirelessly from the Personal Diabetes Manager (PDM). The PDM is a wireless, hand-held device that is used to program the OMNIPOD™ Insulin Management System with customized insulin delivery instructions, monitor the operation of the system, and check blood glucose levels using blood glucose test strips sold under the trademark FREESTYLE™. There is no tubing connecting the device to the PDM. OMNIPOD™ Insulin Management System is worn beneath the clothing, and the PDM can be carried separately in a backpack, briefcase, or purse. Similar to currently available insulin pumps, the OMNIPOD™ Insulin Management System features fully programmable continuous subcutaneous insulin delivery with multiple basal rates and bolus options, suggested bolus calculations, safety checks, and alarm features.

The aim of insulin treatment of diabetics is typically to administer enough insulin such that the patient will have blood glucose levels within the physiological range and normal carbohydrate metabolism throughout the day. Because the pancreas of a diabetic individual does not secrete sufficient insulin throughout the day, in order to effectively control diabetes through insulin therapy, a long-lasting insulin treatment, known as basal insulin, must be administered to provide the slow and steady release of insulin that is needed to control blood glucose concentrations and to keep cells supplied with energy when no food is being digested. Basal insulin is necessary to suppress glucose production between meals and overnight and preferably mimics the patient's normal pancreatic basal insulin secretion over a 24-hour period. Thus, a diabetic patient may administer a single dose of a long-acting insulin each day subcutaneously, with an action lasting about 24 hours.

Furthermore, in order to effectively control diabetes through insulin therapy by dealing with postprandial rises in glucose levels, a bolus, fast-acting treatment must also be administered. The bolus insulin, which is generally administered subcutaneously, provides a rise in plasma insulin levels at approximately 1 hour after administration, thereby limiting hyperglycemia after meals. Thus, these additional quantities of regular insulin, with a duration of action of, e.g., 5 to 6 hours, may be subcutaneously administered at those times of the day when the patient's blood glucose level tends to rise too high, such as at meal times. As an alternative to administering basal insulin in combination with bolus insulin, repeated and regular lower doses of bolus insulin may be administered in place of the long-acting basal insulin, and bolus insulin may be administered postprandially as needed.

Currently, regular subcutaneously injected insulin is recommended to be dosed at 30 to 45 minutes prior to mealtime. As a result, diabetic patients and other insulin users must engage in considerable planning of their meals and of their insulin administrations relative to their meals. Unfortunately, intervening events that may take place between administration of insulin and ingestion of the meal may affect the anticipated glucose excursions.

Furthermore, there is also the potential for hypoglycemia if the administered insulin provides a therapeutic effect over too great a time, e.g., after the rise in glucose levels that occur as a result of ingestion of the meal has already been lowered. As outlined in the Examples, this risk of hypoglycemia is increased in patients who have been treated with C-peptide due to a reduced requirement for insulin.

Accordingly, in one aspect of any of the methods disclosed herein, the present invention includes a method for reducing the risk of the patient developing hypoglycemia by reducing the average daily dose of insulin administered to the patient by about 5% to about 50% after starting PEGylated C-peptide therapy. In another aspect, the dose of insulin administered is reduced by about 5% to about 45% compared to the patient's insulin dose prior to starting PEGylated C-peptide treatment. In another aspect, the dose of insulin administered is reduced by about 5% to about 40% compared to the patient's insulin dose prior to starting PEGylated C-peptide treatment. In another aspect, the dose of insulin administered is reduced by about 5% to about 35% compared to the patient's insulin dose prior to starting PEGylated C-peptide treatment. In another aspect, the dose of insulin administered is reduced by about 5% to about 30% compared to the patient's insulin dose prior to starting PEGylated C-peptide treatment. In another aspect, the dose of insulin administered is reduced by about 5% to about 25% compared to the patient's insulin dose prior to starting PEGylated C-peptide treatment. In another aspect, the dose of insulin administered is reduced by about 5% to about 20% compared to the patient's insulin dose prior to starting PEGylated C-peptide treatment. In another aspect, the dose of insulin administered is reduced by about 5% to about 15% compared to the patient's insulin dose prior to starting PEGylated C-peptide treatment. In another aspect, the dose of insulin administered is reduced by about 5% to about 10% compared to the patient's insulin dose prior to starting PEGylated C-peptide treatment.

In another aspect, the dose of insulin administered is reduced by about 2% to about 10% compared to the patient's insulin dose prior to starting PEGylated C-peptide treatment. In another aspect, the dose of insulin administered is reduced by about 2% to about 15% compared to the patient's insulin dose prior to starting PEGylated C-peptide treatment. In another aspect, the dose of insulin administered is reduced by about 2% to about 20% compared to the patient's insulin dose prior to starting PEGylated C-peptide treatment.

In another aspect, the dose of insulin administered is reduced by about 10% to about 50% compared to the patient's insulin dose prior to starting PEGylated C-peptide treatment. In another aspect, the dose of insulin administered is reduced by about 10% to about 45% compared to the patient's insulin dose prior to starting PEGylated C-peptide treatment. In another aspect, the dose of insulin administered is reduced by about 10% to about 40% compared to the patient's insulin dose prior to starting PEGylated C-peptide treatment. In another aspect, the dose of insulin administered is reduced by about 10% to about 35% compared to the patient's insulin dose prior to starting C-peptide treatment. In another aspect, the dose of insulin administered is reduced by about 10% to about 30% compared to the patient's insulin dose prior to starting PEGylated C-peptide treatment. In another aspect, the dose of insulin administered is reduced by about 10% to about 25% compared to the patient's insulin dose prior to starting PEGylated C-peptide treatment. In another aspect, the dose of insulin administered is reduced by about 10% to about 20% compared to the patient's insulin dose prior to starting PEGylated C-peptide treatment. In another aspect, the dose of insulin administered is reduced by at least 10% compared to the patient's insulin dose prior to starting PEGylated C-peptide treatment.

In one aspect of any of these methods, the dose of short-acting insulin administered is selectively reduced by any of the prescribed ranges listed above. In another aspect of any of these methods, the dose of intermediate-acting insulin administered is selectively reduced by any of the prescribed ranges. In one aspect of any of these methods, the dose of long-acting insulin administered is selectively reduced by any of the prescribed ranges listed above.

In another aspect of any of these methods, the dose of intermediate- and long-acting insulin administered is independently reduced by any of the prescribed ranges listed above, while the dose of short-acting insulin remains substantially unchanged.

In one aspect of these methods, the dose of short-acting insulin administered is reduced by about 5% to about 50% compared to the patient's insulin dose prior to starting PEGylated C-peptide treatment. In another embodiment, the dose of short-acting insulin administered is reduced by about 5% to about 35% compared to the patient's insulin dose prior to starting PEGylated C-peptide treatment. In another embodiment, the dose of short-acting insulin administered is reduced by about 10% to about 20% compared to the patient's insulin dose prior to starting PEGylated C-peptide treatment. In one aspect of these methods, the dose of short-acting insulin administered preprandially for a meal is reduced. In another aspect of these methods, the dose of short-acting insulin administered in the morning or at nighttime is reduced. In another aspect of any of these methods, the dose of short-acting insulin administered is reduced while the dose of long-acting and/or intermediate-acting insulin administered to the patient is substantially unchanged.

In another aspect of any of the methods disclosed herein, the present invention includes a method for reducing the risk of the patient developing hypoglycemia by reducing the average daily dose of intermediate-acting insulin administered to the patient by about 5% to about 35% after starting PEGylated C-peptide therapy. In one aspect of these methods, the dose of intermediate-acting insulin administered is reduced by about 5% to about 50% compared to the patient's insulin dose prior to starting PEGylated C-peptide treatment. In another embodiment, the dose of intermediate-acting insulin administration is reduced by about 5% to about 35% compared to the patient's insulin dose prior to starting PEGylated C-peptide treatment. In another embodiment, the dose of intermediate-acting insulin administered is reduced by about 10% to about 20% compared to the patient's insulin dose prior to starting PEGylated C-peptide treatment. In another aspect of these methods, the dose of intermediate-acting insulin administered in the morning or at nighttime is reduced. In another aspect of any of these methods, the dose of intermediate-acting insulin administered is reduced while the dose of short-acting insulin administered to the patient is substantially unchanged.

In another aspect of any of the methods disclosed herein, the present invention includes a method for reducing the risk of the patient developing hypoglycemia by reducing the average daily dose of long-acting insulin administered to the patient by about 5% to about 50% after starting PEGylated C-peptide therapy. In one embodiment, the dose of long-acting insulin administered is reduced by about 5% to about 35% compared to the patient's insulin dose prior to starting PEGylated C-peptide treatment. In another embodiment, the dose of long-acting insulin administered is reduced by about 10% to about 20% compared to the patient's insulin dose prior to starting PEGylated C-peptide treatment. In another aspect of these methods, the dose of long-acting insulin administered in the morning or at nighttime is reduced. In another aspect of any of these methods, the dose of long-acting insulin administered is reduced while the dose of short-acting insulin administered to the patient is substantially unchanged.

In certain preferred embodiments, the patient achieves improved insulin utilization and insulin sensitivity while experiencing a reduced risk of developing hypoglycemia after treatment with PEGylated C-peptide as compared with baseline levels prior to treatment. Preferably, the improved insulin utilization and insulin sensitivity are measured by a statistically significant decline in HOMA (Homeostasis Model Assessment) (Turner et al.: *Metabolism* 28(11): 1086-1096, (1979)).

Subcutaneous administration of the PEGylated C-peptide will typically not be into the same site as that most recently used for insulin administration, i.e. PEGylated C-peptide and insulin will be injected into different sites. Specifically in one aspect, the site of PEGylated administration will typically be at least about 10 cm way from the site most recently used for insulin administration. In another aspect, the site of PEGylated C-peptide administration will typically be at least about 15 cm away from the site most recently used for insulin administration. In another aspect, the site of PEGylated C-peptide administration will typically be at least about 20 cm away from the site most recently used for insulin administration.

Examples of different sites include for example, and without limitation, injections into the left and right arm, or injections into the left and right thigh, or injections into the left or right buttock, or injections into the opposite sides of the abdomen. Other obvious variants of different sites include injections in an arm and thigh, or injections in an arm and buttock, or injections into an arm and abdomen, etc.

Moreover one of ordinary skill in the art, i.e. a physician, or diabetic patient, will recognize and understand how to inject PEGylated C-peptide and insulin into any other combination of different sites, based on the prior art teaching, and numerous text books and guides on insulin administration that provide disclosure on how to select different insulin injection sites. See for example, the following representative text books (Learning to live well with diabetes, Ed. Cheryl Weiler, (1991) DCI Publishing, Minneapolis, Minn.; American Diabetes Association Complete Guide to Diabetes, ISBN 0-945448-64-3 (1996)).

In one aspect of any of the claimed methods, PEGylated C-peptide is administered to the opposite side of the abdomen to the site most recently used for insulin administration, approximately 15 to 20 cm apart.

VII. Pharmaceutical Compositions

In one aspect, the present invention includes a pharmaceutical composition comprising PEGylated C-peptide, and a pharmaceutically acceptable carrier, diluent or excipient.

Pharmaceutical compositions suitable for the delivery of PEGylated C-peptide and methods for their preparation will be readily apparent to those skilled in the art and may comprise any of the known carriers, diluents, or excipients. Such compositions and methods for their preparation may be found, e.g., in *Remington's Pharmaceutical Sciences,* 19th Edition (Mack Publishing Company, 1995).

In one aspect, the pharmaceutical compositions may be in the form of sterile aqueous solutions and/or suspensions of the pharmaceutically active ingredients, aerosols, ointments, and the like. Formulations which are aqueous solutions are most preferred. Such formulations typically contain the PEGylated C-peptide itself, water, and one or more buffers which act as stabilizers (e.g., phosphate-containing buffers) and optionally one or more preservatives. Such formulations containing, e.g., about 1 to 200 mg, about 3 to 100 mg, about 3 to 80 mg, about 3 to 60 mg, about 3 to 40 mg, about 3 to 30 mg, about 0.3 to 3.3 mg, about 1 to 3.3 mg, about 1 to 2 mg, about 1 to 3.3 mg, about 2 to 3.3 mg or any of the ranges mentioned herein, e.g., about 200 mg, about 150 mg, about 120 mg, about 100 mg, about 80 mg, about 60 mg, about 50 mg, about 40 mg, about 30 mg, about 20 mg, or about 10 mg, or about 8 mg, or about 6 mg, or about 5 mg, or about 4 mg, or about 3 mg, or about 2 mg, or about 1 mg, or about 0.5 mg of the PEGylated C-peptide and constitute a further aspect of the invention.

Pharmaceutical compositions may include pharmaceutically acceptable salts of PEGylated C-peptide. For a review on suitable salts, see *Handbook of Pharmaceutical Salts: Properties, Selection, and Use* by Stahl and Wermuth (Wiley-VCH, 2002). Suitable base salts are formed from bases which form non-toxic salts. Representative examples include the aluminium, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts. In one embodiment, PEGylated C-peptide may be prepared as a gel with a pharmaceutically acceptable positively charged ion.

In one aspect, the positively charged ion may be a monovalent metal ion. In one aspect, the metal ion is selected from sodium and potassium.

In one aspect, the positively charged ion may be a divalent metal ion. In one aspect, the metal ion is selected from calcium, magnesium, and zinc.

The PEGylated C-peptide may be administered at any time during the day. For humans, the dosage used may range from about 0.1 to 200 mg/week of PEGylated C-peptide, e.g., from about 0.1 to 0.3 mg/week, about 0.3 to 1.5 mg/week, about 1 mg to about 3.5 mg/week, about 1.5 to 2.25 mg/week, about 2.25 to 3.0 mg/week, about 3.0 to 6.0 mg/week, about 6.0 to 10 mg/week, about 10 to 20 mg/week, about 20 to 40 mg/week, about 40 to 60 mg/week, about 60 to 80 mg/week, about 80 to 100 mg/week, about 100 to 120 mg/week, about 120 to 140 mg/week, about 140 to 160 mg/week, about 160 to 180 mg/week, and about 180 to about 200 mg/week.

Preferably the total weekly dose used of PEGylated C-peptide is about 1 mg to about 3.5 mg, about 1 mg to about 20 mg, about 20 mg to about 50 mg, about 50 mg to about 100 mg, about 100 mg to about 150 mg, or about 150 mg to about 200 mg.

The total weekly dose of PEGylated C-peptide may be about 0.1 mg, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 7 mg, about 8 mg, about 9 mg, about 10 mg, about 12 mg, about 15 mg, about 18 mg, about 21 mg, about 24 mg, about 27 mg, about 30 mg, about 33 mg, about 36 mg, about 39 mg, about 42 mg, about 45 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg. (It will be appreciated that masses of PEGylated C-peptide referred to above are dependent on the bioavailability of the delivery system and based on the use of PEGylated C-peptide with a molecular mass of approximately 40,000 Da.)

In another aspect of any of these methods and pharmaceutical compositions, the therapeutic dose of PEGylated C-peptide comprises a weekly dose ranging from about 1 mg to about 45 mg. In another aspect of any of these methods and pharmaceutical compositions, the therapeutic dose of PEGylated C-peptide comprises a weekly dose ranging from about 3 mg to about 15 mg. In another aspect of any of these methods and pharmaceutical compositions, the therapeutic dose of PEGylated C-peptide comprises a weekly dose ranging from about 30 mg to about 60 mg. In another aspect of any of these methods and pharmaceutical compositions, the therapeutic dose of PEGylated C-peptide comprises a weekly dose ranging from about 60 mg to about 120 mg.

In another aspect of any of these methods and pharmaceutical compositions, the therapeutic dose of PEGylated C-peptide maintains the average steady-state concentration of PEGylated C-peptide ($C_{ss\text{-}ave}$) in the patient's plasma of between about 0.2 nM and about 6 nM.

In another aspect of any of these methods and pharmaceutical compositions, the therapeutic dose of PEGylated C-peptide is provided to the patient so as to maintain the average steady-state concentration of PEGylated C-peptide in the patient's plasma between about 0.2 nM and about 6 nM when using a dosing interval of 3 days or longer. In another aspect of any of these methods and pharmaceutical compositions, the therapeutic dose of PEGylated C-peptide is provided to the patient so as to maintain the average steady-state concentration of PEGylated C-peptide in the patient's plasma between about 0.2 nM and about 6 nM when using a dosing interval of 4 days or longer. In another aspect of any of these methods and pharmaceutical compositions, the therapeutic dose of PEGylated C-peptide is provided to the patient so as to maintain the average steady-state concentration of PEGylated C-peptide in the patient's plasma between about 0.2 nM and about 6 nM when using a dosing interval of 5 days or longer. In another aspect of any of these methods and pharmaceutical compositions, the therapeutic dose of PEGylated C-peptide is provided to the patient so as to maintain the average steady-state concentration of PEGylated C-peptide in the patient's plasma between about 0.2 nM and about 6 nM when using a dosing interval of at least one week. In any of these methods and pharmaceutical compositions, the therapeutic dose is administered by daily subcutaneous injections. In another aspect of any of these methods and pharmaceutical compositions, the therapeutic dose is administered by a sustained release formulation or device.

In another aspect of any of these methods and pharmaceutical compositions, the therapeutic dose of PEGylated C-peptide is provided to the patient so as to maintain the average steady-state concentration of PEGylated C-peptide in the patient's plasma between about 0.4 nM and about 8 nM when using a dosing interval of 3 days or longer. In another aspect of any of these methods and pharmaceutical compositions, the therapeutic dose of PEGylated C-peptide is provided to the patient so as to maintain the average steady-state concentration of PEGylated C-peptide in the patient's plasma between about 0.4 nM and about 8 nM when using a dosing interval of 4 days or longer. In another aspect of any of these methods and pharmaceutical compositions, the therapeutic dose of PEGylated C-peptide is provided to the patient so as to maintain the average steady-state concentration of PEGylated C-peptide in the patient's plasma between about 0.4 nM and about 8 nM when using a dosing interval of 5 days or longer. In another aspect of any of these methods and pharmaceutical compositions, the therapeutic dose of PEGylated C-peptide is provided to the patient so as to maintain the average steady-state concentration of PEGylated C-peptide in the patient's plasma between about 0.4 nM and about 8 nM when using a dosing interval of 7 days or longer.

In another aspect of any of these methods and pharmaceutical compositions, the therapeutic dose of PEGylated C-peptide is provided to the patient so as to maintain the average steady-state concentration of PEGylated C-peptide in the patient's plasma between about 0.6 nM and about 8 nM when using a dosing interval of 3 days or longer. In another aspect of any of these methods and pharmaceutical compositions, the therapeutic dose of PEGylated C-peptide is provided to the patient so as to maintain the average steady-state concentration of PEGylated C-peptide in the patient's plasma between about 0.6 nM and about 8 nM when using a dosing interval of 4 days or longer. In another aspect of any of these methods and pharmaceutical compositions, the therapeutic dose of PEGylated C-peptide is provided to the patient so as to maintain the average steady-state concentration of PEGylated C-peptide in the patient's plasma between about 0.6 nM and about 8 nM when using a dosing interval of 5 days or longer. In another aspect of any of these methods and pharmaceutical compositions, the therapeutic dose of PEGylated C-peptide is provided to the patient so as to maintain the average steady-state concentration of PEGylated C-peptide in the patient's plasma between about 0.6 nM and about 8 nM when using a dosing interval of 7 days or longer.

The dose may or may not be in solution. If the dose is administered in solution, it will be appreciated that the volume of the dose may vary, but will typically be 20 µL-2 mL. Preferably the dose for S.C. administration will be given in a volume of 2000 µL, 1500 µL, 1200 µL, 1000 µL, 900 µL, 800 µL, 700 µL, 600 µL, 500 µL, 400 µL, 300 µL, 200 µL, 100 µL, 50 µL, or 20 µL.

PEGylated C-peptide doses in solution can also comprise a preservative and/or a buffer. For example, the preservatives m-cresol, or phenol can be used. Typical concentrations of preservatives include 0.5 mg/mL, 1 mg/mL, 2 mg/mL, 3 mg/mL, 4 mg/mL, or 5 mg/mL. Thus, a range of concentration of preservative may include 0.2 to 10 mg/mL, particularly 0.5 to 6 mg/mL, or 0.5 to 5 mg/mL. Examples of buffers that can be used include histidine (pH 6.0), sodium phosphate buffer (pH 6 to 7.5), or sodium bicarbonate buffer (pH 7 to 7.5). It will be appreciated that the PEGylated C-peptide dose may comprise one or more of a native or intact C-peptide, fragments, derivatives, or other functionally equivalent variants of C-peptide.

VIII. Methods for Administration

A dose of PEGylated C-peptide may comprise full-length human C-peptide (SEQ. ID. No. 1) and the C-terminal C-peptide fragment EGSLQ (SEQ. ID. No. 31) and/or a C-peptide homolog or C-peptide derivative. Further, the dose may if desired only contain a fragment of C-peptide, e.g., EGSLQ. Thus, the term "C-peptide" may encompass a single C-peptide entity or a mixture of different "C-peptides". Administration of the PEGylated C-peptide may be by any suitable method known in the medicinal arts, including oral, parenteral, topical, or subcutaneous administration, inhalation, or the implantation of a sustained delivery device or composition. In one aspect, administration is by subcutaneous administration.

Pharmaceutical compositions of the invention suitable for oral administration may, e.g., comprise PEGylated C-peptide in sterile purified stock powder form preferably covered by an envelope or envelopes (enterocapsules) protecting from degradation of the drug in the stomach and thereby enabling absorption of these substances from the gingiva or in the small intestines. The total amount of active ingredient in the composition may vary from 99.99 to 0.01 percent of weight.

For oral administration a pharmaceutical composition comprising a PEGylated C-peptide can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

Pharmaceutical compositions to be used in the invention suitable for parenteral administration are typically sterile aqueous solutions and/or suspensions of the pharmaceutically active ingredients preferably made isotonic with the blood of the recipient. Such compositions generally comprise excipients, salts, carbohydrates, and buffering agents (preferably to a pH of from 3 to 9), such as sodium chloride, glycerin, glucose, mannitol, sorbitol, and the like.

For some applications, pharmaceutical compositions for parenteral administration may be suitably formulated as a sterile non-aqueous solution or as a dried form to be used in conjunction with a suitable vehicle such as sterile, pyrogen-free water. The preparation of parenteral formulations under sterile conditions, e.g., by lyophilization, may readily be accomplished using standard pharmaceutical techniques well-known to those skilled in the art.

Pharmaceutical compositions comprising PEGylated C-peptide for use in the present invention may also be administered topically, (intra)dermally, or transdermally to the skin or mucosa. Pharmaceutical compositions for topical administration may be formulated to be immediate and/or modified release. Modified release formulations include delayed, sustained, pulsed, controlled, targeted and programmed release. Typical formulations for this purpose include gels, hydrogels, lotions, solutions, creams, ointments, dusting powders, dressings, foams, films, skin patches, wafers, implants, sponges, fibers, bandages, and microemulsions. Liposomes may also be used. Typical carriers include alcohol, water, mineral oil, liquid petrolatum, white petrolatum, glycerin, polyethylene glycol, and propylene glycol. Penetration enhancers may be incorporated—see, e.g., Finnin and Morgan: *J. Pharm. Sci.* 88(10): 955-958, (1999). Other means of topical administration include delivery by electroporation, iontophoresis, phonophoresis, sonophoresis, and microneedle or needle-free (e.g., POWDERJECT™, BIOJECT™) injection.

Pharmaceutical compositions of PEGylated C-peptide for parenteral administration may be administered directly into the blood stream, into muscle, or into an internal organ. Suitable means for parenteral administration include intravenous, intra-arterial, intraperitoneal, intrathecal, intraventricular, intraurethral, intrasternal, intracranial, intramuscular, intrasynovial, and subcutaneous. Suitable devices for parenteral administration include needle (including microneedle) injectors, needle-free injectors, and infusion techniques.

Subcutaneous administration of PEGylated C-peptide will typically not be into the same site as that most recently used for insulin administration. In one aspect of any of the claimed methods and pharmaceutical compositions, PEGylated C-peptide is administered to the opposite side of the abdomen to the site most recently used for insulin administration. In another aspect of any of the claimed methods and pharmaceutical compositions, PEGylated C-peptide is administered to the upper arm. In another aspect of any of the claimed methods and pharmaceutical compositions, PEGylated C-peptide is administered to the abdomen. In another aspect of any of the claimed methods and pharmaceutical compositions, PEGylated C-peptide is administered to the upper area of the buttock. In another aspect of any of the claimed methods and pharmaceutical compositions, PEGylated C-peptide is administered to the front of the thigh.

Formulations for parenteral administration may be formulated to be immediate and/or sustained release. Sustained release compositions include delayed, modified, pulsed, controlled, targeted and programmed release. Thus PEGylated C-peptide may be formulated as a suspension or as a solid, semi-solid, or thixotropic liquid for administration as an implanted depot providing sustained release. Examples of such formulations include without limitation, drug-coated stents and semi-solids and suspensions comprising drug-loaded poly(DL-lactic-co-glycolic)acid (PGLA), poly(DL-lactide-co-glycolide) (PLG) or poly(lactide) (PLA) lamellar vesicles or microparticles, hydrogels (Hoffman A S: *Ann. N.Y. Acad. Sci.* 944: 62-73 (2001)), poly-amino acid nanoparticles systems, such as the Medusa system developed by Flamel Technologies Inc., nonaqueous gel systems such as ATRIGEL® developed by Atrix, Inc., and SABER® (Sucrose Acetate Isobutyrate Extended Release) developed by Durect Corporation, and lipid-based systems such as DEPOFOAM® developed by SkyePharma.

Sustained release devices capable of delivering desired doses of PEGylated C-peptide over extended periods of time are known in the art. For example, U.S. Pat. Nos. 5,034,229; 5,557,318; 5,110,596; 5,728,396; 5,985,305; 6,113,938; 6,156,331; 6,375,978; and 6,395,292; teach osmotically-driven devices capable of delivering an active agent formulation, such as a solution or a suspension, at a desired rate over an extended period of time (i.e., a period ranging from more than one week up to one year or more). Other exemplary sustained release devices include regulator-type pumps that provide constant flow, adjustable flow, or programmable flow of beneficial agent formulations, which are available from, e.g., OMNIPOD™ Insulin Management System (Insulet Corporation, Codman of Raynham, Mass., Medtronic of Minneapolis, Minn., Intarcia Therapeutics of Hayward, Calif., and Tricumed Medinzintechnik GmbH of Germany). Further examples of devices are described in U.S. Pat. Nos. 6,283,949; 5,976,109; 5,836,935; and 5,511,355.

Because they can be designed to deliver a desired active agent at therapeutic levels over an extended period of time, implantable delivery systems can advantageously provide long-term therapeutic dosing of a desired active agent without requiring frequent visits to a healthcare provider or repetitive self-medication. Therefore, implantable delivery devices can work to provide increased patient compliance, reduced irritation at the site of administration, fewer occupational hazards for healthcare providers, reduced waste hazards, and increased therapeutic efficacy through enhanced dosing control.

Among other challenges, two problems must be addressed when seeking to deliver biomolecular material over an extended period of time from an implanted delivery device. First, the biomolecular material must be contained within a formulation that substantially maintains the stability of the material at elevated temperatures (i.e., 37° C. and above) over the operational life of the device. Second, the biomolecular material must be formulated in a way that allows delivery of the biomolecular material from an implanted device into a desired environment of operation over an extended period of time. This second challenge has proven particularly difficult where the biomolecular material is included in a flowable composition that is delivered from a device over an extended period of time at low flow rates (i.e., ≤100 µL/day).

Peptide drugs such as C-peptide may degrade via one or more of several different mechanisms, including deamidation, oxidation, hydrolysis, and racemization. Significantly, water is a reactant in many of the relevant degradation pathways. Moreover, water acts as a plasticizer and facilitates the unfolding and irreversible aggregation of biomolecular materials. To work around the stability problems created by aqueous formulations of biomolecular materials, dry powder formulations of biomolecular materials have been created using known particle formation processes, such as by known lyophilization, spray drying, or desiccation techniques. Though dry powder formulations of biomolecular material have been shown to provide suitable stability characteristics, it would be desirable to provide a formulation that is not only stable over extended periods of time, but is also flowable and readily deliverable from an implantable delivery device.

Accordingly in one aspect of any of the claimed methods and pharmaceutical compositions, the PEGylated C-peptide is provided in a nonaqueous drug formulation, and is delivered from a sustained release implantable device, wherein the PEGylated C-peptide is stable for at least two months of time at 37° C.

Representative nonaqueous formulations for PEGylated C-peptide include those disclosed in International Publication Number WO00/45790 that describes nonaqueous vehicle formulations that are formulated using at least two of a polymer, a solvent, and a surfactant.

WO98/27962 discloses an injectable depot gel composition containing a polymer, a solvent that can dissolve the polymer and thereby form a viscous gel, a beneficial agent, and an emulsifying agent in the form of a dispersed droplet phase in the viscous gel.

WO04089335 discloses nonaqueous vehicles that are formed using a combination of polymer and solvent that results in a vehicle that is miscible in water. As it is used herein, the term "miscible in water" refers to a vehicle that, at a temperature range representative of a chosen operational environment, can be mixed with water at all proportions without resulting in a phase separation of the polymer from the solvent such that a highly viscous polymer phase is formed. For the purposes of the present invention, a "highly viscous polymer phase" refers to a polymer containing composition that exhibits a viscosity that is greater than the viscosity of the vehicle before the vehicle is mixed with water.

Accordingly in another aspect of any of the claimed methods, PEGylated C-peptide is provided in a sustained release device comprising: a reservoir having at least one drug delivery orifice, and a stable nonaqueous drug formulation. In one aspect of these methods and pharmaceutical compositions, the formulation comprises: at least PEGylated C-peptide; and a nonaqueous, single-phase vehicle comprising at least one polymer and at least one solvent, the vehicle being miscible in water, wherein the drug is insoluble in one or more vehicle components and the PEGylated C-peptide formulation is stable at 37° C. for at least two months. In one aspect, the solvent is selected from the group consisting of glycofurol, benzyl alcohol, tetraglycol, n-methylpyrrolidone, glycerol formal, propylene glycol, and combinations thereof.

In particular, a nonaqueous formulation is considered chemically stable if no more than about 35% of the PEGylated C-peptide is degraded by chemical pathways, such as by oxidation, deamidation, and hydrolysis, after maintenance of the formulation at 37° C. for a period of two months, and a formulation is considered physically stable if, under the same conditions, no more than about 15% of the C-peptide contained in the formulation is degraded through aggregation. A drug formulation is stable according to the present invention if at least about 65% of the PEGylated C-peptide remains physically and chemically stable after about two months at 37° C.

The PEGylated C-peptide can be administered intranasally or by inhalation, typically in the form of a dry powder (either alone, as a mixture, e.g., in a dry blend with lactose, or as a mixed component particle, e.g., mixed with phospholipids, such as phosphatidylcholine) from a dry powder inhaler, as an aerosol spray from a pressurized container, pump, spray, atomizer (preferably an atomizer using electro hydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, e.g., chitosan or cyclodextrin. The pressurized container, pump, spray, atomizer, or nebulizer contains a solution or suspension of the compound(s) of the invention comprising, e.g., ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 μm). This may be achieved by any appropriate method, such as spiral jet milling, fluid bed jet milling, supercritical fluid processing to form nanoparticles, high pressure homogenization, or spray drying.

The particle size of PEGylated C-peptide of this invention in the formulation delivered by the inhalation device is important with respect to the ability of C-peptide to make it into the lungs, and preferably into the lower airways or alveoli. Preferably, the PEGylated C-peptide of this invention is formulated so that at least about 10% of the PEGylated C-peptide delivered is deposited in the lung, preferably about 10% to about 20%, or more. It is known that the maximum efficiency of pulmonary deposition for mouth breathing humans is obtained with particle sizes of about 2 pm to about 3 pm. When particle sizes are above about 5 pm, pulmonary deposition decreases substantially. Particle sizes below about 1 pm cause pulmonary deposition to decrease, and it becomes difficult to deliver particles with sufficient mass to be therapeutically effective. Thus, particles of the PEGylated C-peptide delivered by inhalation have a particle size preferably less than about 10 pm, more preferably in the range of about 1 pm to about 5 pm. The formulation of the PEGylated C-peptide is selected to yield the desired particle size in the chosen inhalation device.

Advantageously for administration as a dry powder, a PEGylated C-peptide of this invention is prepared in a particulate form with a particle size of less than about 10 pm, preferably about 1 to about 5 pm. The preferred particle size is effective for delivery to the alveoli of the patient's lung. Preferably, the dry powder is largely composed of particles produced so that a majority of the particles have a size in the desired range. Advantageously, at least about 50% of the dry powder is made of particles having a diameter less than about 10 pm. Such formulations can be achieved by spray drying, milling, or critical point condensation of a solution containing the PEGylated C-peptide of this invention and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Capsules (made, e.g., from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose, and trehalose.

A suitable solution formulation for use in an atomizer using electro hydrodynamics to produce a fine mist may contain from 100 μg to 200 mg of PEGylated C-peptide per actuation and the actuation volume may vary from 1 μL to 100 μL. A typical formulation may comprise PEGylated C-peptide propylene glycol, sterile water, ethanol, and sodium chloride. Alternative solvents that may be used instead of propylene glycol include glycerol and polyethylene glycol. Suitable flavors, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release using, e.g., PGLA. Modified release formulations include delayed, sustained, pulsed, controlled, targeted, and programmed release.

In the case of dry powder inhalers and aerosols, the dosage unit is determined by means of a valve that delivers a metered amount. Units in accordance with the invention are typically arranged to administer a metered dose or "puff" containing from 1 mg to 200 mg of PEGylated C-peptide. The overall daily dose will typically be in the range 1 mg to 200 mg that may be administered in a single dose or, more usually, as divided doses throughout the day.

Examples of commercially available inhalation devices suitable for the practice of the invention are sold under the trademarks TURBHALER™ (Astra), ROTAHALER® (Glaxo), DISKUS®, SPIROS™ inhaler (Dura), devices marketed by Inhale Therapeutics under the trademarks AERX™ (Aradigm), and ULTRAVENT® nebulizer (Mallinckrodt), ACORN II® nebulizer (Marquest Medical Products), VENTOLIN® metered dose inhaler (Glaxo), and the SPINHALER® powder inhaler (Fisons), and the like.

Kits are also contemplated for this invention. A typical kit would comprise a container, preferably a vial, for the PEGylated C-peptide formulation comprising PEGylated C-peptide in a pharmaceutically acceptable formulation, and instructions, and/or a product insert or label. In one aspect, the instructions include a dosing regimen for administration of said PEGylated C-peptide to an insulin-dependent patient to reduce the risk, incidence, or severity of hypoglycemia. In one aspect, the kit includes instructions to reduce the administration of insulin by about 5% to about 35% when starting PEGylated C-peptide therapy. In another aspect, the instructions include directions for the patient to closely monitor their blood glucose levels when starting PEGylated C-peptide therapy. In another aspect, the instructions include directions for the patient to avoid situations or circumstances that might predispose the patient to hypoglycemia when starting PEGylated C-peptide therapy.

EXAMPLES

Abbreviations. The following abbreviations have been used in the specification and examples: ACN=acetonitrile; Bzl=Bn=benzyl; DIEA=N,N-diisopropylethylamine; DMF=N,N-dimethylformamide; tBu=tert-butyl; TSTU=O—(N-succinimidyl)-1,1,3,3-tetramethyluronium tetrafluoroborate; THF=tetrahydrofuran; EtOAc=ethyl acetate; DIPEA=DIEA=diisopropylethylamine; HOAt=1-hydroxy-7-azabenzotriazole; NMP=N-methylpyrrolidin-2-one; TEA=triethyl amine; SA=sinapinic acid; Su=1-succinimidyl=2,5-dioxo-pyrrolidin-1-yl; TFA=trifluoroacetic acid; DCM=dichloromethane; DMSO=dimethyl sulphoxide; RT=room temperature; General Procedures: The following examples and general procedures refer to intermediate compounds and final products identified in the specification. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius (° C.) and unless otherwise indicated, all parts and percentages are by weight (i.e., w/w) when referring to yields and all parts are by volume (i.e., v/v) when referring to solvents and eluents.

Example 1

Preparation of Branched Chain PEGylated C-Peptides

Where $R_1$=Methyl, and $n_1$ and $n_2$ are about 450 to about 520.

One (1) g of human C— peptide (SEQ. ID. No. 1) (0.33 mM) was dissolved in 25 mL DMF/water (20 mL/5 mL). The pH was adjusted to 7.8 with N-methylmorpholine (NMM). A solution of SUNBRIGHT® GL2-400GS2 (NOF Corporation) approximate molecular weight 40,000 Da (1.85 g of the activated PEG (0.04 mM) in DMF/water/ACN (25 mL/5 mL/10 mL) was then added and the reaction was stirred overnight at room temperature.

The solution was diluted with purified water to 700 mL. The DMF concentration was 6% v/v. The pH was adjusted to 4 to 4.5 with acetic acid and filtered. The solution was purified by HPLC using a YMC-ODS column (2.5×30 cm) using an 0.5% acetic acid (mobile phase A)/100 mM sodium acetate (mobile phase B)/ACN (mobile phase C) gradient. Separations were completed by equilibrating the column with three column volumes of 90% A/10% C. PEGylated C-peptide was loaded on to, and washed with, 90% B/10% C (three column volumes), followed by isocratic washing with one column volume of 90% A/10% C. Elution was achieved via a multilinear gradient starting with 90% A/10% C to 70% A/30% C over two column volumes, followed by a linear gradient consisting of 70% A/30% C and rising to 50% A/50% C over five column volumes.

The pool from the HPLC (140 mL) was diluted with 70 mL purified water and evaporated to a volume of 130 mL at 25° C. The final concentration was 12 g/L. The solution was lyophilized to yield 1500 mg of PEGylated C-peptide (80% yield).

Fractions collected after purification were analyzed by reverse phase and size exclusion HPC. Reverse phase HPLC was conducted using a Waters UPLCBEH C18 17 μM column, using a mobile phase of ACN and 0.1% TFA using a two component linear gradient of 24% to 40% ACN over 3 minutes, followed by 40% to 90% ACN over 1 minute, at a flow rate of 0.25 mL/min, a column temperature of 40° C., and a sample concentration of 5 mg/mL. A representative chromatogram is presented in FIG. 1.

Figure 2:
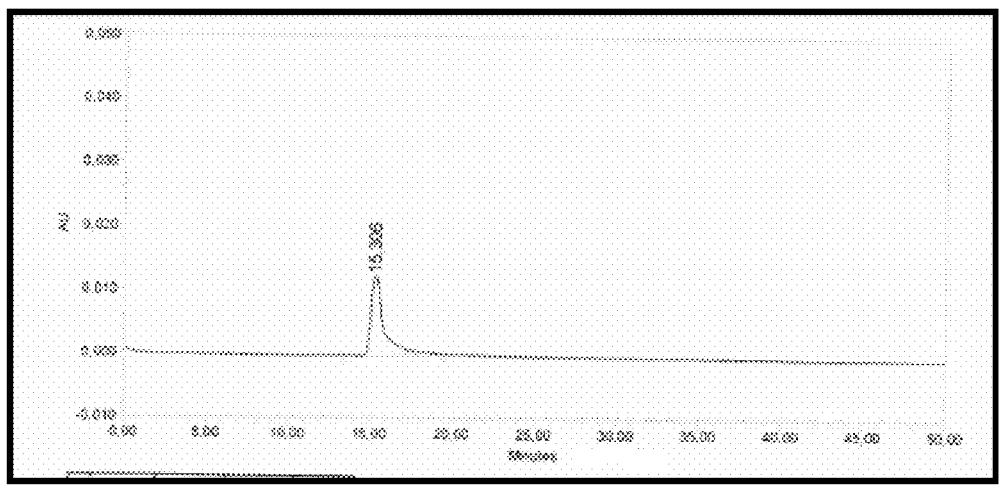
FIG. 2 shows a size exclusion chromatogram of a 40 kDa branched chain PEGylated C-peptide of the invention.

Size exclusion chromatography was conducted using a Superdex 75, 10/300GL column using an isocratic elution with a mobile phase of 0.1 M phosphate buffer pH 7.4 containing 2.7 mM KCl and 0.137 M NaCl at a flow rate of 0.5 mL/min. A representative chromatogram is presented in FIG. 2.

Example 2

Preparation of Additional Branched Chain PEGylated C-Peptides

Using similar reaction conditions as described for Example 1, and using the following reagents in the place of SUNBRIGHT® GL2-400GS2, the following PEGylated C-peptides of MW 10 kDa to 80 kDa may be readily prepared.

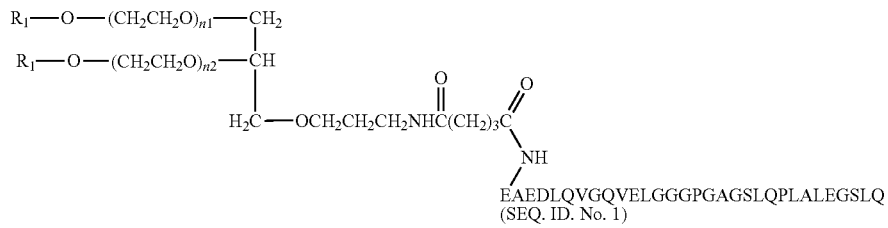

Use of SUNBRIGHT® GL2-400TS yields:

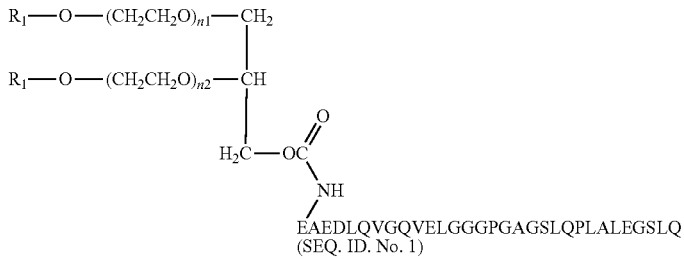

EAEDLQVGQVELGGGPGAGSLQPLALEGSLQ
(SEQ. ID. No. 1)

Where $R_1$=Methyl.

Use of SUNBRIGHT® GL3-400TS100U yields:

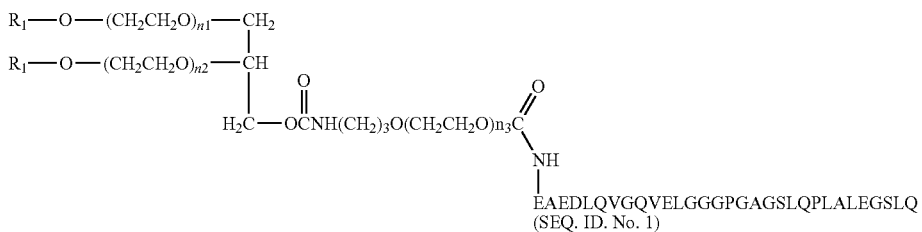

EAEDLQVGQVELGGGPGAGSLQPLALEGSLQ
(SEQ. ID. No. 1)

Where $R_1$=Methyl.

Use of SUNBRIGHT® GL3-400GS100U yields:

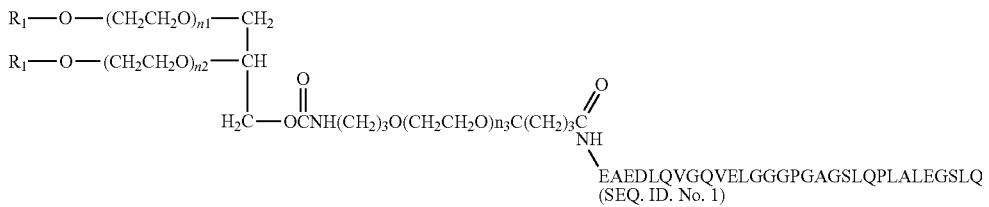

EAEDLQVGQVELGGGPGAGSLQPLALEGSLQ
(SEQ. ID. No. 1)

Where $R_1$=Methyl.

Use of SUNBRIGHT® GL3-400HS100U yields:

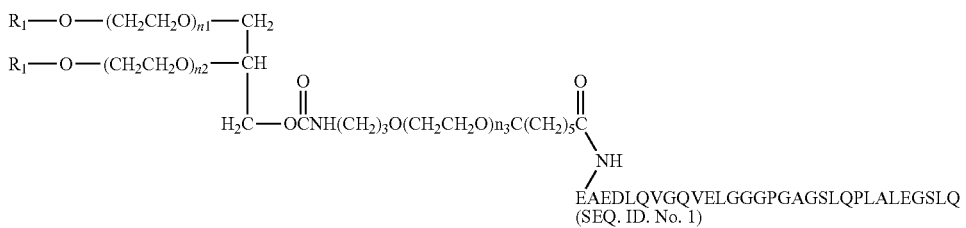

EAEDLQVGQVELGGGPGAGSLQPLALEGSLQ
(SEQ. ID. No. 1)

Where $R_1$=Methyl.
Use of SUNBRIGHT® LY-400NS yields:

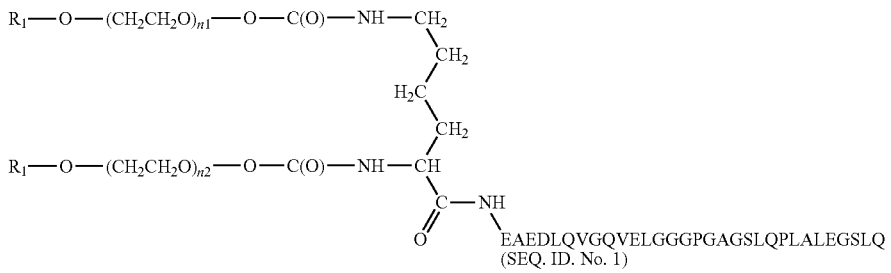
(SEQ. ID. No. 1)

Where $R_1$=Methyl.
Use of the active intermediate

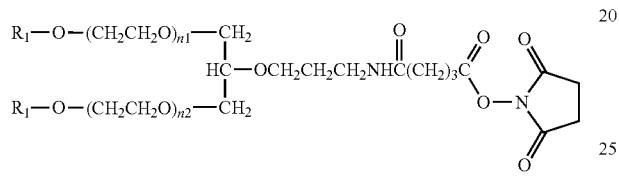

yields:

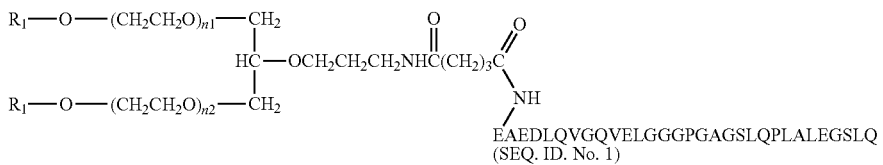
(SEQ. ID. No. 1)

Where $R_1$=methyl.

Example 3

Preparation of Linear Chain PEGylated C-Peptides

Using similar reaction conditions as described for Example 1, and using the following reagents in the place of SUNBRIGHT® GL2-400GS2, the following PEGylated C-peptides of MW 5 kDa to 80 kDa may be readily prepared.
SUNBRIGHT® ME-200GS.

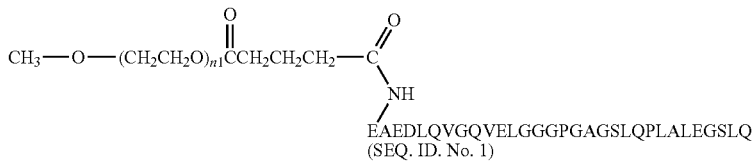
(SEQ. ID. No. 1)

Figure 3:
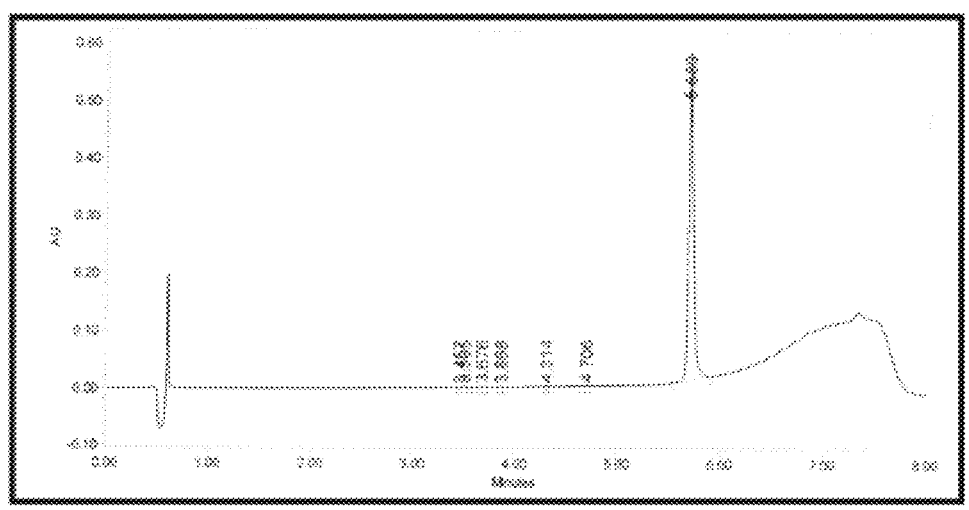
FIG. 3 shows a reverse phase chromatogram of a 20 kDa linear chain PEGylated C-peptide of the invention.

Fractions collected after purification were analyzed by reverse phase and size exclusion HPC. Reverse phase HPLC was conducted using a Waters UPLCBEH C18 17 µM column, using a mobile phase of ACN and 0.1% TFA using a two component linear gradient of 24% to 40% ACN over 3 minutes, followed by 40% to 90% ACN over 1 minute, at a flow rate of 0.25 mL/min, a column temperature of 40° C. and a sample concentration of 5 mg/mL. A representative chromatogram is presented in FIG. 3.

Figure 4:
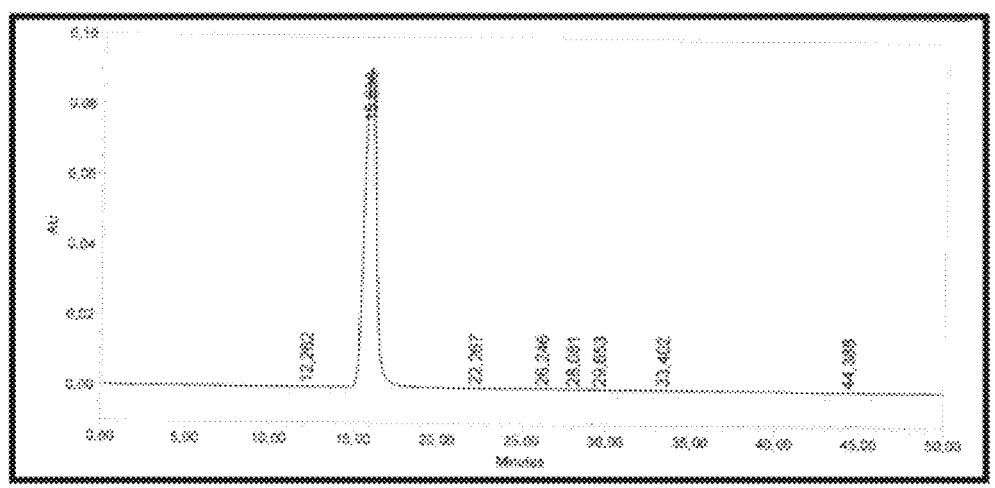
FIG. 4 shows a size exclusion chromatogram of a 20 kDa linear chain PEGylated C-peptide of the invention.

Size exclusion chromatography was conducted using a Superdex 75, 10/300GL column using an isocratic elution with a mobile phase of 0.1 M phosphate buffer pH 7.4 containing 2.7 mM KCl and 0.137 M NaCl at a flow rate of 0.5 mL/min. A representative chromatogram is presented in FIG. 4.

Example 4

Preparation of Additional Linear Chain PEGylated C-Peptides

Using similar reaction conditions as described for Example 1, and using the following reagents in the place of SUNBRIGHT® GL2-400GS2, the following linear PEGylated C-peptides of MW 5 kDa to 80 kDa may be readily prepared.

Use of SUNBRIGHT® ME-200CS yields:

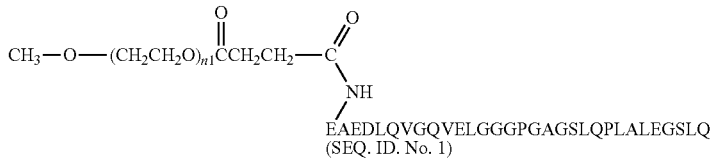

Use of SUNBRIGHT® ME-200HS yields:

Use of SUNBRIGHT® ME-200TS yields:

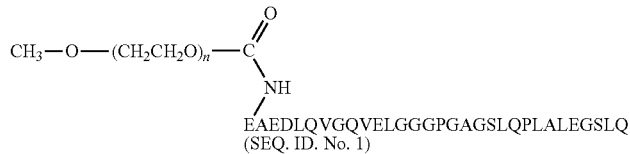

Use of SUNBIO® P1PAL-30 yields:

Use of SUNBIO® P1APAL-30 yields:

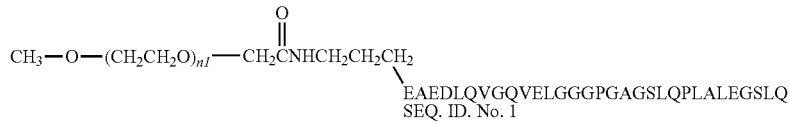

Use of SUNBIO® P1TPAL-5 yields:

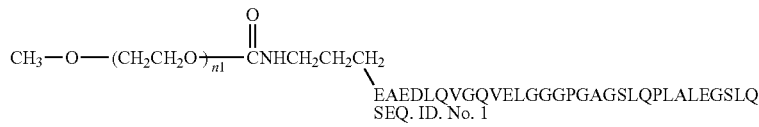

Use of SUNBIO® P1BAL-30 yields:

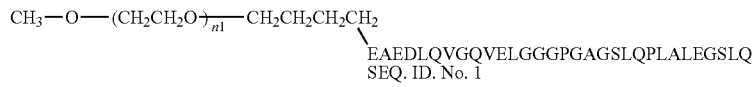

EAEDLQVGQVELGGGPGAGSLQPLALEGSLQ
SEQ. ID. No. 1

Use of SUNBIO® P1ABAL-30 yields:

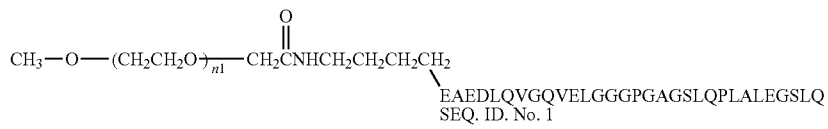

EAEDLQVGQVELGGGPGAGSLQPLALEGSLQ
SEQ. ID. No. 1

Use of SUNBIO® P1TBAL-5 yields:

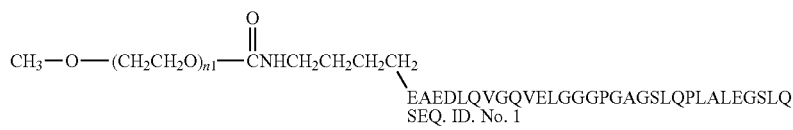

EAEDLQVGQVELGGGPGAGSLQPLALEGSLQ
SEQ. ID. No. 1

Example 5

Measurement of Pharmacokinetic Characteristics in Dogs

A pharmacokinetic (PK) study was conducted to determine the C-peptide PK profile with unmodified C-peptide in beagle dogs.

Methods:

Two male and one female dog received S.C. the unmodified synthetic human C-peptide (0.5 mg/kg; 0.025 mL/kg) formulated in phosphate buffered saline (20 mg/mL). Dogs were bled by venipuncture and blood samples were collected at predetermined time points over 14 days. Plasma samples were obtained after centrifugation of the blood (3,000 rpm for 10 minutes) and stored at −80° C. until analysis. A CRO with Good Laboratory Practice (GLP) capabilities (MicroConstants, Inc.; San Diego, Calif.) performed the bioanalytical work. Plasma levels of C-peptide were measured by an enzyme-linked immunosorbant assay (ELISA) technique based on a commercial kit for human C-peptide determination (Mercodia; catalog number 10-1136-01) using the manufacturer's instructions. Results were expressed as C-peptide concentrations. For the PK analysis, the below quantitation level (BQL) was treated as zero and nominal time points were used for all calculations. PK parameters were determined by standard model independent methods based on the individual plasma concentration-time data for each animal using model 200 in WinNonlin Professional 5.2.1 (Pharsight Corp., Mountain View, Calif.).

Results:

All animals survived the duration of the study. Each treatment was well tolerated based on the absence of clinical abnormalities. The mean±standard deviation (SD) for C-peptide maximum concentration ($C_{max}$) and area under the curve ($AUC_{(0-t)}$) values following S.C. dosing of the unmodified C-peptide in dogs are presented in Table E1 below. The corresponding mean±SD C-peptide plasma concentration-time profiles on a linear scale after 1 day and 12 days post dose are presented in FIG. 5A and FIG. 5B, respectively. Single-dose administration of unmodified C-peptide resulted in a rapid peak accumulation, and then rapid loss of C-peptide from the circulation in dogs. The use of unmodified C-peptide resulted in circulating levels of C-peptide that were BQL within half a day.

TABLE E1

Mean PK Parameters of C-Peptide in Dogs Following a Single S.C. Dose of Unmodified Aqueous C-peptide (CP-AQ)

| | $C_{max}$ (ng/mL) | | $AUC_{(0-t)}$ (ng · day/mL)[a] | |
|---|---|---|---|---|
| | Mean | SD | Mean | SD |
| CP-AQ | 757 | 192 | 77.4 | 6.82 |

[a]$AUC_{(0-t)}$ is the area under the plasma concentration-time curve from immediate post dose to the last measurable sampling time and is calculated by the linear trapezoidal rule.

A second PK study was conducted to determine the C-peptide PK profiles using two representative PEGylated C-peptides of different molecular weights (a 20 kDa linear PEG (Example 3) and a 40 kDa branched PEG (Example 1)) in beagle dogs. Results were compared to those for unmodified C-peptide.

Methods:

Three male dogs received S.C. the 20 kDa PEGylated synthetic human C-peptide (0.5 mg/kg equivalents of C-peptide; 0.09 mL/kg) formulated in phosphate buffered saline (50.8 mg/mL PEGylated C-peptide) and three male dogs received S.C. the 40 kDa PEGylated synthetic human C-peptide (0.5 mg/kg equivalents of C-peptide; 0.012 mL/kg) formulated in phosphate buffered saline (82.5 mg/mL PEGylated C-peptide). Dogs were bled by venipuncture and blood samples were collected at predetermined time points over 21 days. Plasma samples were obtained after centrifugation of the blood (3,000 rpm for 10 minutes) and stored at −80° C. until analysis. A CRO with GLP capabilities (MicroConstants, Inc.; San Diego, Calif.) performed the bioanalytical work. Plasma levels of C-peptide were measured by an ELISA technique based on a commercial kit for human C-peptide determination (Mercodia; catalog number 10-1136-01) using PEGylated C-peptide quality control standards. Results were expressed as C-peptide concentrations. For the PK analysis, the BQL was treated as zero and nominal time points were used for all calculations. PK parameters were determined by standard model independent methods based on the individual plasma concentration-time data for each animal using model 200 in WinNonlin Professional 5.2.1 (Pharsight Corp., Mountain View, Calif.).

Results:

All animals survived the duration of the study. Each treatment was well tolerated based on the absence of clinical abnormalities. By comparison to unmodified C-peptide, the use of the PEGylated C-peptide extended C-peptide exposure in the dog to at least 4 days post dose with the 20 kDa linear PEGylated C-peptide, and to at least 15 days post dose with the 40 kDa branched chain PEGylated C-peptide.

Figure 6:
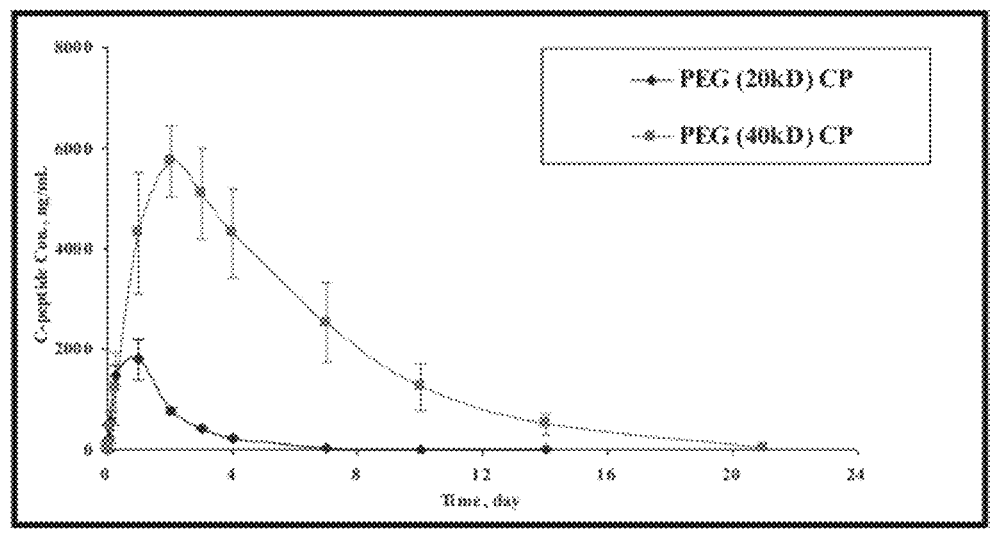
FIG. 6 shows the plasma concentration-time profiles of C-peptide in dogs following single subcutaneous doses of the 20 kDa linear chain PEGylated C-peptide (diamonds) and the 40 kDa branched chain PEGylated C-peptide (squares) using a linear scale. The term "CP" refers to C-peptide.
Figure 7:
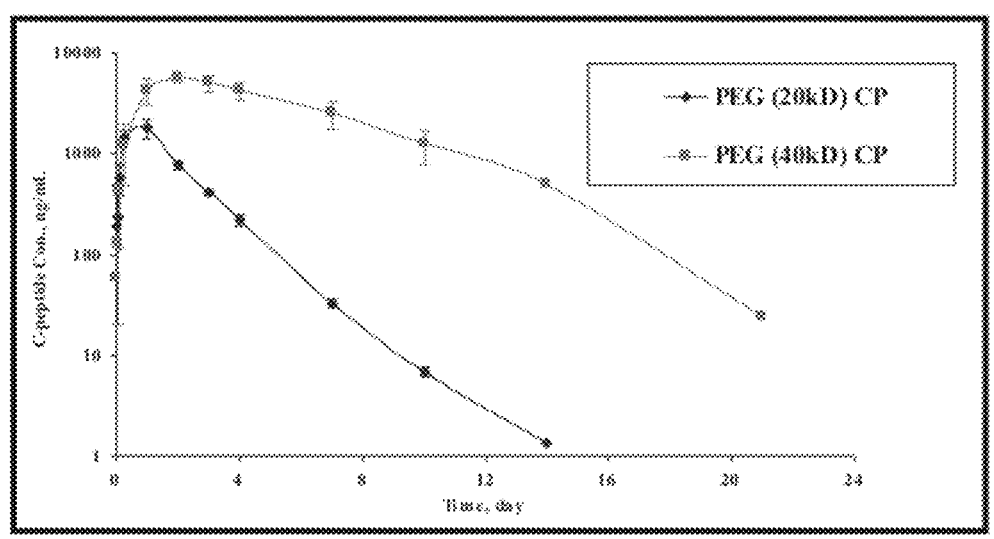
FIG. 7 shows the plasma concentration-time profiles of C-peptide in dogs following single subcutaneous doses of the 20 kDa linear chain PEGylated C-peptide (diamonds) and the 40 kDa branched chain PEGylated C-peptide (squares) using a semi-logarithmic scale. The term "CP" refers to C-peptide.

The mean±SD for C-peptide $C_{max}$, $AUC_{(0-t)}$, and half-life ($T_{1/2}$) values following S.C. dosing of the 20 kDa PEGylated C-peptide and the 40 kDa PEGylated C-peptide in dogs are presented in Table E2 below. The corresponding mean±SD C-peptide plasma concentration-time profiles on linear and semi-logarithmic scales are presented in FIG. 6 and FIG. 7, respectively.

TABLE E2

Mean PK Parameters of C-Peptide in Dogs Following a Single S.C. Dose of a 20 kDa and a 40 kDa PEGylated C-peptide (CP)

|  | PEG (20 kDa) CP | | PEG (40 kDa) CP | | Ratio of PEG (40 kDa) CP to PEG (20 kDa) CP |
|---|---|---|---|---|---|
|  | Mean | SD | Mean | SD |  |
| $C_{max}$ (ng/mL) | 1,800 | 400 | 5,790 | 642 | 2.26 |
| $AUC_{(0-t)}$ (ng · day/mL)$^a$ | 4,060 | 588 | 38,600 | 8,200 | 6.67 |
| $T_{1/2}{}^b$ (Day) | 1.39 | 0.197 | 2.02 | 0.217 | 1.45 |

$^a AUC_{(0-t)}$ is the area under the plasma concentration-time curve from immediate post dose to the last measurable sampling time and is calculated by the linear trapezoidal rule.
$^b T_{1/2}$ is the terminal half-life calculated by ln(2)/λ where λ represents the elimination rate constant for the log-linear portion of the terminal phase.

Surprisingly, the $C_{max}$ and $AUC_{(0-t)}$ values following S.C. dosing of the 40 kDa PEGylated C-peptide were 2.26- and 6.67-fold higher than the corresponding values of the 20 kDa PEGylated C-peptide, respectively. Thus, the 40 kDa branched chain PEGylated C-peptide provides for significantly improved PK properties compared to the 20 kDa PEGylated C-peptide, or compared to unmodified C-peptide. A third PK study was conducted in beagle dogs with lower doses of the 40 kDa branched chain PEGylated C-peptide (0.006, 0.025, and 0.1 mg/kg, via single-dose S.C. injection of PEGylated synthetic human C-peptide (40 kDa PEG; made via SUNBRIGHT® GL2-400GS2, Example 1)) formulated in phosphate buffered saline.

Methods:

Plasma levels of C-peptide were measured over 14 days. A nonclinical CRO (Bio-Quant, Inc.; San Diego, Calif.) performed the animal portion of the study. Nine male and female dogs weighed approximately 7-12 kg and 6-8 kg, respectively, on the day of dose administration (Day 0). Animals were fed during the study and food consumption was determined on Days 0, 1, and 2. Body weights were also determined on Days 7 and 14. The injection area on the back of each animal was shaved and cleaned two days prior to Day 0. There were three groups of dogs (n=2 males and 1 female/group):

Group 1 received a single S.C. injection via 25 G needle of 2 mg/mL PEGylated C-peptide at a dose of 0.05 mL/kg (containing 0.005 mg/kg equivalents of C-peptide).

Group 2 received a single S.C. injection via 25 G needle of 2 mg/mL PEGylated C-peptide at a dose of 0.0125 mL/kg (containing 0.00125 mg/kg equivalents of C-peptide).

Group 3 received a single S.C. injection via 25 G needle of 0.4 mg/mL PEGylated C-peptide at a dose of 0.015 mL/kg (containing 0.0003 mg/kg equivalents of C-peptide).

Dogs were bled by venipuncture and blood samples were collected at Day 0 (pre-dose, 30 minutes, 1 hour, 3 hour, and 6 hour) and Days 1, 2, 3, 4, 7, 10, and 14. Plasma samples were obtained after centrifugation of the blood (3,000 rpm for 10 minutes) and stored at −80° C. until analysis. A CRO with GLP capabilities (MicroConstants, Inc.; San Diego, Calif.) performed the bioanalytical work. Plasma levels of C-peptide were measured by an ELISA technique based on a commercial kit for human C-peptide determination (Mercodia; catalog number 10-1136-01) using PEGylated C-peptide quality control standards. Results were expressed as C-peptide concentrations. For the PK analysis, the BQL was treated as zero and nominal time points were used for all calculations. PK parameters were determined by standard model independent methods based on the individual plasma concentration-time data for each animal using model 200 in WinNonlin Professional 5.2.1 (Pharsight Corp., Mountain View, Calif.).

Results:

All animals survived the duration of the study. Each treatment was well tolerated based on the absence of clinical abnormalities. The mean±SD for C-peptide $C_{max}$, $AUC_{(0-t)}$, and $T_{1/2}$ values following single S.C. doses of PEGylated C-peptide in dogs are presented in Table E3. The corresponding mean±SD for C-peptide plasma concentration-time profiles on linear and semi-logarithmic scales are presented in FIG. 8A and FIG. 8B, respectively. The mean±SD for C-peptide $C_{max}$ and $AUC_{(0-t)}$ values are presented in FIG. 9A and FIG. 9B, respectively.

TABLE E3

Pharmacokinetic Parameters of C-Peptide in Dogs Following Single S. C. Doses of PEGylated C-peptide (40 kDa PEG)

|  | PEGylated C-peptide Dose (mg/kg equivalents of C-peptide) | | | | | |
|---|---|---|---|---|---|---|
|  | 0.005 | | 0.00125 | | 0.0003 | |
|  | Mean | SD | Mean | SD | Mean | SD |
| Cmax (ng/mL) | 73.2 | 2.23 | 19.0 | 4.00 | 1.74 | 1.53 |
| AUC(0-t) (ng · day/mL)a | 470 | 84.3 | 91.9 | 8.86 | 4.17 | 3.94 |
| T½b (day) | 2.44 | 0.599 | 1.93 | 0.530 | 1.76c | ND | aAUC(0-t) is the area under the plasma concentration-time curve from immediate post dose to the last measurable sampling time and is calculated by the linear trapezoidal rule.
bT½ is the terminal half-life calculated by ln(2)/λ where λ represents the elimination rate constant for the log-linear portion of the terminal phase.
cn = 1 and SD was ND (not determined)

In summary, following single S.C. escalating doses of 40 kDa PEGylated C-peptide in dogs, exposure of C-peptide is significantly increased. The results from the second and third PK studies in dogs confirm that the 40 kDa branched chain PEGylated C-peptide provides for significantly improved PK properties compared to the 20 kDa linear chain PEGylated C-peptide, or comparison to unmodified C-peptide (first PK study in dogs). Furthermore, the 40 kDa branched chain PEGylated demonstrated no significant adverse side effects at the doses tested.

Example 7

Pharmacokinetics in Sprague Dawley Rats Following Single Dose s.c. Administration The PK of the 40 kDa PEGylated C-peptide (Example 12) was assessed in Sprague Dawley rats (2/sex/group) following single-dose s.c. administration of 0.0413, 0.167, and 0.664 mg/kg. Blood samples were collected prior to and for 14 days after administration. Plasma samples were analyzed for PEGylated C-peptide using the ELISA method, as described above for the dog study. Individual PK parameters were estimated using "non-compartmental" methods. The mean (±SD) plasma concentration-time profiles following single-dose s.c. administration are illustrated in FIG. 10 with the corresponding PK parameters summarized in Table E4.

TABLE E4

PEGylated C-peptide pharmacokinetics in Sprague Dawley rats following single-dose subcutaneous administration

| Pharma-cokinetic Parameter[a] | CBX129801 Dose, mg/kg | | | | | |
|---|---|---|---|---|---|---|
| | 0.0413 | | 0.167 | | 0.664 | |
| | Mean | SD | Mean | SD | Mean | SD |
| $T_{1/2}$, day | 1.35 | 0.186 | 1.27 | 0.109 | 1.27 | 0.175 |
| $T_{max}$, day | 1.00 | 0.00 | 1.00 | 0.00 | 1.00 | 0.00 |
| $C_{max}$, nM | 3.38 | 0.869 | 12.3 | 2.61 | 34.1 | 10.4 |
| $AUC_{(0-7)}$, nM · day | 8.13 | 1.45 | 33.0 | 7.27 | 101 | 18.7 |
| $AUC_{(0-7)}$, ng · day/mL | 374 | 66.6 | 1,520 | 334 | 4,660 | 862 |
| $AUC_{(0-t)}$, nM · day | 8.13 | 1.45 | 33.9 | 8.31 | 107 | 19.6 |
| $AUC_{(0-t)}$, ng · day/mL | 374 | 66.6 | 1,560 | 382 | 4,920 | 900 |
| $AUC_{(0-inf)}$, nM · day | 8.48 | 1.43 | 34.6 | 7.88 | 108 | 19.4 |
| $AUC_{(0-inf)}$, ng · day/mL | 390 | 65.7 | 1,590 | 362 | 4,950 | 893 |
| CL/F, mL/day/kg | 109 | 20.5 | 109 | 25.5 | 138 | 25.5 |
| Vd/F, mL/kg | 214 | 62.0 | 201 | 50.6 | 250 | 42.9 |

[a]Refer to List of Abbreviations (Table A) for definition of terms.

Example 8

Pharmacokinetics in Cynomolgus Monkeys Following Single Dose s.c. Administration The PK of the 40 kDa PEGylated C-peptide (Example 12) was assessed in Cynomolgus monkeys (2/sex) following single-dose s.c. administration of 0.0827 mg/kg. Blood samples were collected prior to and for 14 days after administration. Plasma samples were analyzed for CBX129801 using the ELISA method as described above for the dog study. Individual PK parameters were estimated using "non-compartmental" methods. The mean (±SD) plasma concentration-time profile following single-dose s.c. administration is illustrated in FIG. 11 with the corresponding PK parameters summarized in Table E5.

TABLE E5

Pharmacokinetic Parameters of PEGylated C-peptide in Cynomolgus Monkeys, at 0.0827 mg/kg

| Pharmacokinetic Parameter[a] | Mean | SD |
|---|---|---|
| $T_{max}$, day | 2.00 | 0.816 |
| $T_{1/2}$, day | 5.44 | 2.05 |
| $C_{max}$, nM | 13.2 | 1.32 |
| $AUC_{(0-7)}$, nM · day | 67.5 | 7.01 |
| $AUC_{(0-7)}$, ng · day/mL | 3,110 | 323 |
| $AUC_{(0-14)}$, nM · day | 95.7 | 16.9 |
| $AUC_{(0-14)}$, ng · day/mL | 4,400 | 770 |
| $AUC_{(0-inf)}$, nM · day | 121 | 37.0 |
| $AUC_{(0-inf)}$, ng · day/mL | 5,560 | 1,710 |
| CL/F, mL/day/kg | 16.0 | 4.90 |
| Vd/F, ml/kg | 115 | 10.0 |

[a]Refer to List of Abbreviations (Table A) for definition of terms.

These results indicate that peak concentration occurred within 2 days; the $T_{1/2}$ is ~5.4 days. Since the monkeys were not fasted and because the detection antibody cross-reacts with monkey C-peptide, the results for the 40 kDa PEGylated C-peptide (Example 12) include endogenous C-peptide levels. Therefore at the later time points (i.e., Days 10 and 14) when the measured PEGylated C-peptide levels were lower, the contribution of endogenous monkey C-peptide could have confounded the results. With the Day 14 time point removed from the analysis, the $T_{1/2}$ is 3.7 days. In summary for these single-dose PK studies, following s.c. administration, the peak PEGylated C-peptide plasma concentration generally occurs within 1 to 5 days. AUC and $C_{max}$ increase with increasing dose and are generally dose proportional.

Example 9

Repeat-Dose Pharmacokinetic Studies with Unmodified C-Peptide

In the five GLP toxicology studies conducted with non-PEGylated C-peptide for up to 4 weeks in rats and 13 weeks in Cynomolgus monkeys, the C-peptide was continuously infused s.c. via implanted osmotic pumps. The plasma concentration of C-peptide was measured periodically throughout the studies and a steady-state concentration ($C_{ss}$) over the duration of exposure has been determined for each study as shown in Table E6.

TABLE E6

Summary of unmodified C-peptide concentrations in repeated-dose toxicity studies at the no observed effect level

| Species | Duration | No Observed Effect Level | C-peptide $C_{ss}$[a](nM) |
|---|---|---|---|
| Sprague Dawley rat | 14 days | 2 mg/kg/day | 27[b] |
| Sprague Dawley rat | 14 days | 2 mg/kg/day | 16[b] |
| Sprague Dawley rat | 4 weeks | 0.5 mg/kg/day | 4.2[c] |
| Cynomolgus monkey | 14 days | 2 mg/kg/day | 84[b] |
| Cynomolgus monkey | 13 weeks | 3.6 mg/kg/day | 40[d] |

[a]Test article delivered by continuous s.c. infusion.
[b]Mean $C_{ss}$ estimated from the C-peptide plasma levels on days 2, 10, and 14.
[c]Mean $C_{ss}$ estimated from the C-peptide plasma levels on days 2, 14, and 28.
[d]Mean $C_{ss}$ estimated from the C-peptide plasma levels on days 2, 28, 37/38, 56, and 91

In conclusion, there were sustained C-peptide levels throughout the duration of dosing in these toxicology studies.

Example 10

Repeat-Dose Pharmacokinetic Studies

The PK of the 40 kDa PEGylated C-peptide (Example 12) has been assessed following multiple dose administration in rats and monkeys. These studies are summarized below. Pharmacokinetics in Sprague Dawley Rats Following Repeated-Dose Subcutaneous Administration (Weekly) for 28 Days.

Methods:

The PK of the 40 kDa PEGylated C-peptide (Example 12) was assessed in Sprague Dawley rats (3/sex/group per time point) following multiple dose subcutaneous administration of 2.74, 8.22, and 27.4 mg/kg/week for 5 doses. Blood samples were collected prior to and for 7 days following the first dose. Trough blood samples were collected after the 2nd through 4th doses. Following the last dose ($5^{th}$ dose), blood samples were collected for 28 days. Plasma samples were analyzed for PEGylated C-peptide using an ELISA method, as described previously. PK parameters were estimated using "non-compartmental" methods and the mean concentration-time profile for each dose by gender.

Figure 12:
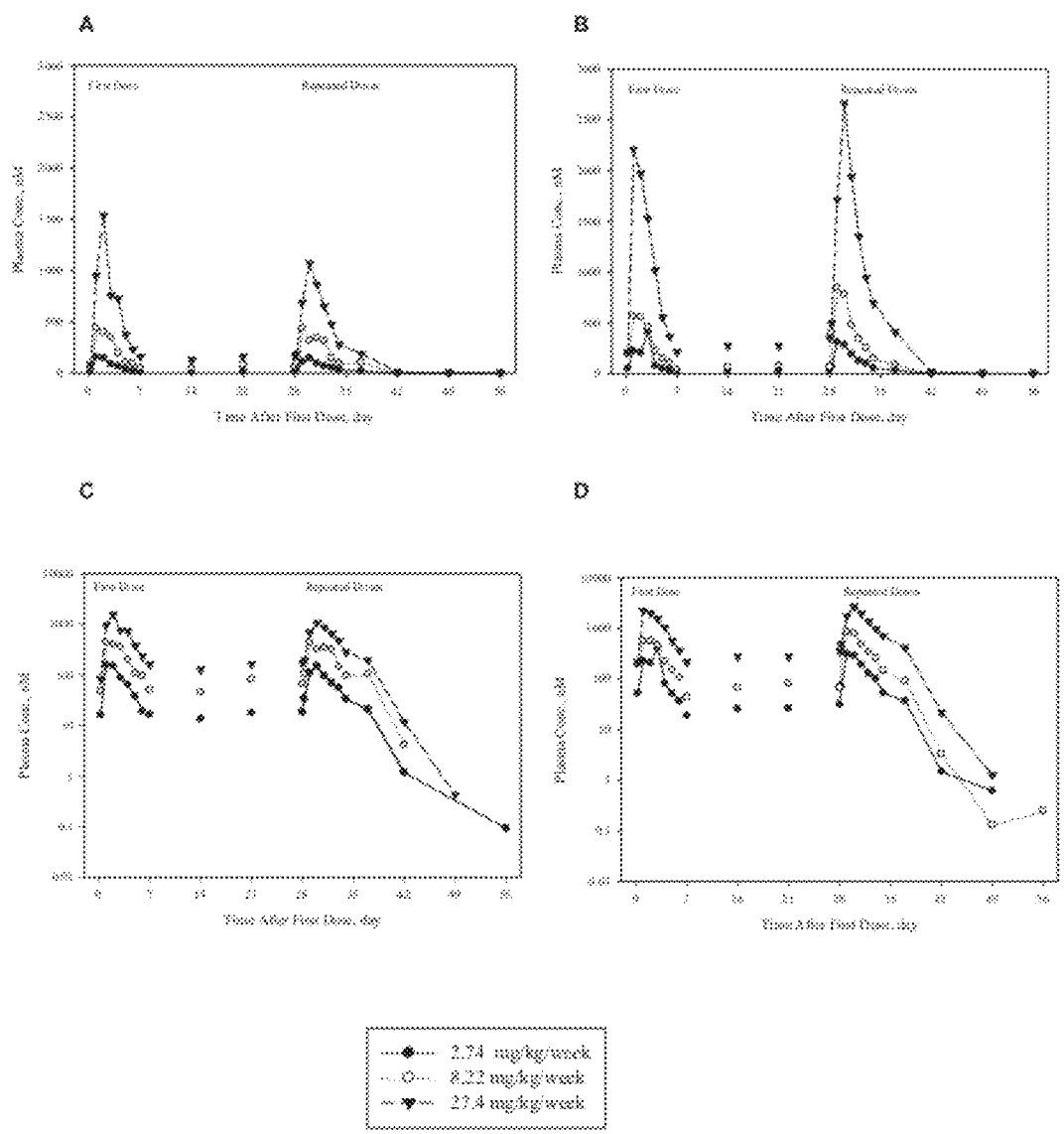
FIG. 12 shows mean C-peptide plasma concentration-time profile in Sprague Dawley rats following multiple dose subcutaneous administration of PEGylated C-peptide. Panel A Male, Linear scale; Panel B Female Linear scale; Panel C Male Semi-log scale; Panel D Female Semi-log scale.
Figure 13:
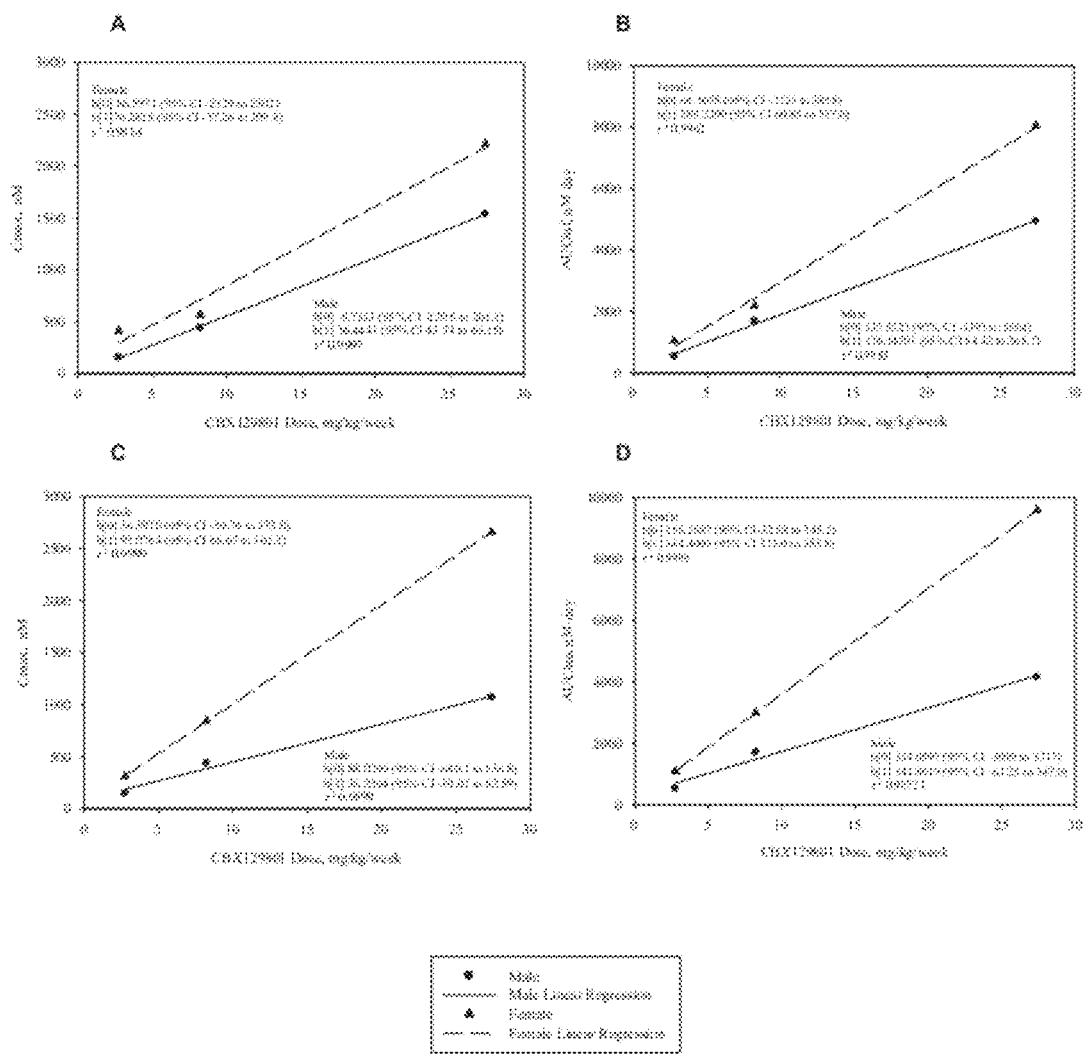
FIG. 13 shows the relationship between C. and $AUC_{(0-inf)}$ in Sprague Dawley rats as a function of dose; Panel A $C_{max}$, first dose; Panel B $AUC_{(0-inf)}$ first dose; Panel C $C_{max}$, last dose; Panel D $AUC_{(0-inf)}$ last dose. The term "CBX129801" refers to the PEGylated C-peptide of Example 12. The term "$C_{max}$" refers to the maximum serum or plasma concentration of drug which occurs during the period of release which is monitored. The term $AUC_{(0-t)}$ refers to the area under the plasma concentration-time curve from time zero to the time of the last quantifiable concentration.

Results:

The mean (±SD) plasma concentration-time profiles upon multiple dose s.c. administration by gender are illustrated in FIG. 12 with the corresponding PK parameters summarized in Table E7.

TABLE E7

Summary of Pharmacokinetic Characteristics in Sprague Dawley Rats Following Repeated-Dose Subcutaneous Administration (Weekly) for 28 Days

| | Sex | | | | | |
|---|---|---|---|---|---|---|
| | Male | | | Female | | |
| | Dose, mg/kg/week | | | | | |
| | 2.74 | 8.22 | 27.4 | 2.74 | 8.22 | 27.4 |
| First-Dose Parameters[a] | | | | | | |
| $C_{max}$, nM | 156 | 440 | 1,540 | 412 | 564 | 2,210 |
| $T_{max}$, day[b] | 1.00 | 1.00 | 2.00 | 3.00 | 1.00 | 1.00 |
| $T_{1/2}$, day | 1.52 | 1.49 | 1.62 | 1.47 | 1.26 | 1.46 |
| $AUC_{tau}$, nM · day | 507 | 1,580 | 4,580 | 1,020 | 2,110 | 7,590 |
| $AUC_{inf}$, nM · day | 539 | 1,690 | 4,950 | 1,060 | 2,190 | 8,050 |
| CL/F, mL/day/kg | 108 | 103 | 118 | 55.1 | 79.7 | 72.5 |
| $V_d$/F, mL/kg | 237 | 222 | 275 | 117 | 145 | 153 |
| $C_{max}$ Male/Female Ratio | 0.379 | 0.780 | 0.697 | — | — | — |
| $AUC_{inf}$ Male/Female Ratio | 0.508 | 0.772 | 0.615 | — | — | — |
| CL/F Male/Female Ratio | 1.96 | 1.30 | 1.63 | — | — | — |
| $V_d$/F Male/Female Ratio | 2.03 | 1.53 | 1.80 | — | — | — |
| Repeated-Dose Parameters[a] | | | | | | |
| $C_{max}$, nM | 147 | 438 | 1,070 | 311 | 846 | 2,660 |
| $T_{max}$, day[b] | 2.00 | 1.00 | 2.00 | 1.00 | 1.00 | 2.00 |
| $T_{1/2}$, day | 1.43 | 1.51 | 1.66 | 1.65 | 1.35 | 1.84 |
| $AUC_{tau}$, nM · day | 524 | 1,710 | 4,150 | 1,090 | 3,000 | 9,590 |
| CLss/F, mL/day/kg | 111 | 102 | 141 | 53.6 | 58.3 | 60.9 |
| $V_d$ss/F, mL/kg | 230 | 223 | 337 | 128 | 114 | 161 |
| $C_{max}$ Male/Female Ratio | 0.473 | 0.518 | 0.402 | — | — | — |
| $AUC_{tau}$ Male/Female Ratio | 0.481 | 0.570 | 0.433 | — | — | — |
| CLss/F Male/Female Ratio | 2.07 | 1.75 | 2.32 | — | — | — |
| $V_d$ss/F Male/Female Ratio | 1.80 | 1.96 | 2.09 | — | — | — |
| Repeated/1st Dose $C_{max}$ Ratio | 0.942 | 0.995 | 0.695 | 0.755 | 1.50 | 1.20 |

TABLE E7-continued

Summary of Pharmacokinetic Characteristics in Sprague Dawley Rats Following Repeated-Dose Subcutaneous Administration (Weekly) for 28 Days

| | Sex | | | | | |
|---|---|---|---|---|---|---|
| | Male | | | Female | | |
| | Dose, mg/kg/week | | | | | |
| | 2.74 | 8.22 | 27.4 | 2.74 | 8.22 | 27.4 |
| Repeated/1st Dose AUC$_{tau}$ Ratio | 1.03 | 1.08 | 0.906 | 1.07 | 1.42 | 1.26 |

[a]Refer to List of Abbreviations (Table A) for definition of terms;
[b]Expressed as median.

Overall, these results indicate that steady state is achieved by Day 14 to Day 21. Exposure increased with increasing dose with peak plasma concentrations occurring between Day 1 and Day 3. AUC and C$_{max}$ following the first and last dose appear to be dose proportional over the range assessed with AUC at steady state similar to that following the first dose (AUC steady-state to first dose ratio ranging from 0.7 to 1.5). The T$_{1/2}$ appears similar across the 3 doses and following the first and last dose (~1.5 days). Systemic exposure in females is ~2 fold higher than males. Detectable drug levels persisted for approximately 2 weeks at all doses in the 28-day recovery period following cessation of dosing with no detectable drug at the end of the recovery period except in one male (2.74 mg/kg/week) and one female (8.22 mg/kg/week). Due to initial technical difficulties with the anti-drug antibody (ADA) assay, results are not available for anti-PEGylated C-peptide antibodies. The high exposures, generally dose proportional results, and consistent clearance between the first and the last doses with PEGylated C-peptide supports the proposition that any antibody formation did not likely impact exposure to any significant degree.

Pharmacokinetics in Cynomolgus Monkeys Following Repeated-Dose Subcutaneous Administration (Weekly) for 28 Days.

Methods:

The PK of the 40 kDa PEGylated C-peptide (Example 12) was assessed in Cynomolgus monkeys (5/sex/group) upon multiple dose s.c. administration of 1.33, 4.0, and 13.3 mg/kg/week for 5 doses. Blood samples were collected prior to and for 7 days following the first dose. Trough blood samples were collected after the 2nd through 4th doses. Following the last dose (5th dose), blood samples were collected for up to 28 days. Plasma samples were analyzed for PEGylated C-peptide using an ELISA method, as described previously. PK parameters were estimated using "non-compartmental" methods.

Figure 14:
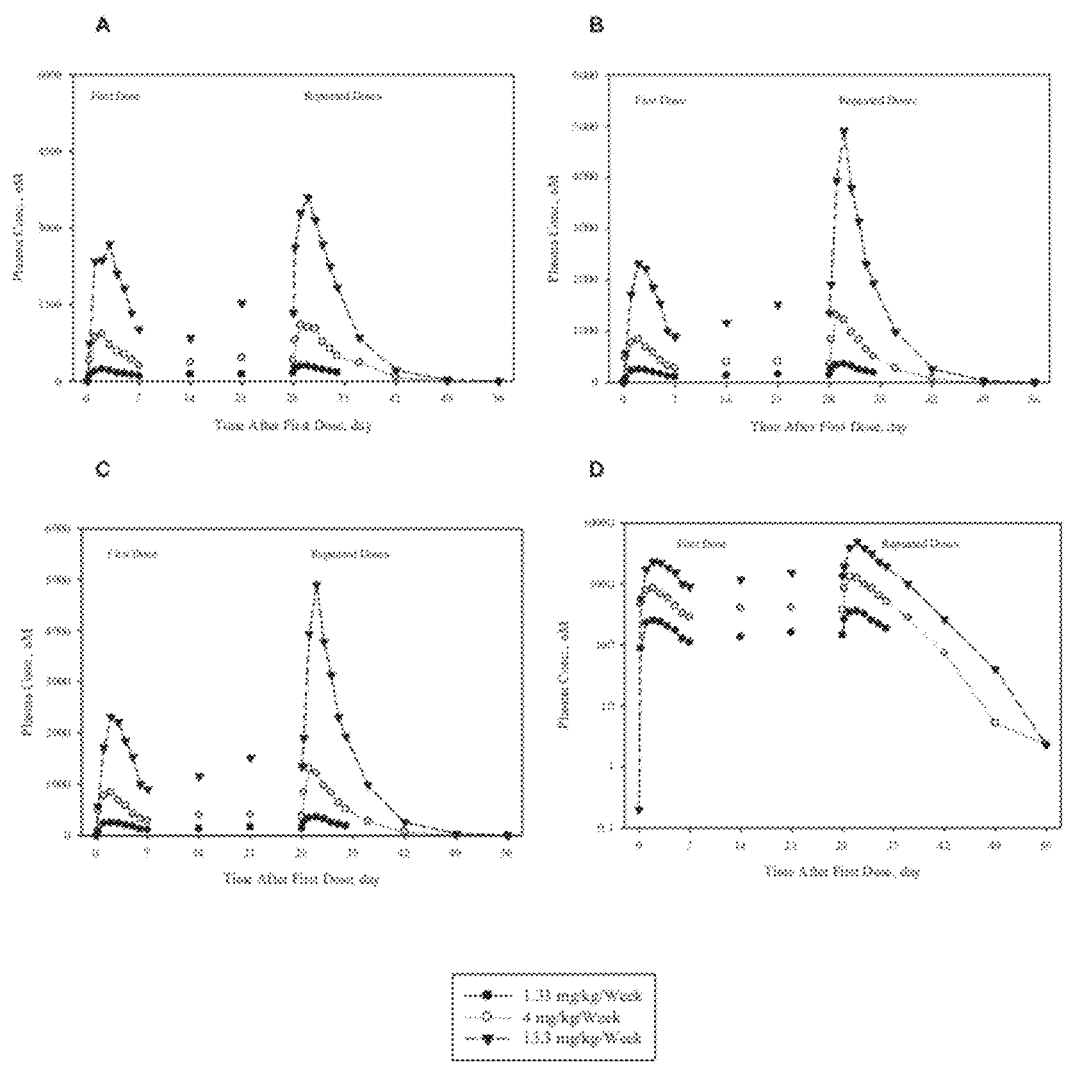
FIG. 14 shows Mean C-peptide plasma concentration-time profile in Cynomolgus monkeys upon multiple-dose subcutaneous administration Panel A Male, Linear scale; Panel B Female Linear scale; Panel C Male Semi-log scale; Panel D Female Semi-log scale.
Figure 15:
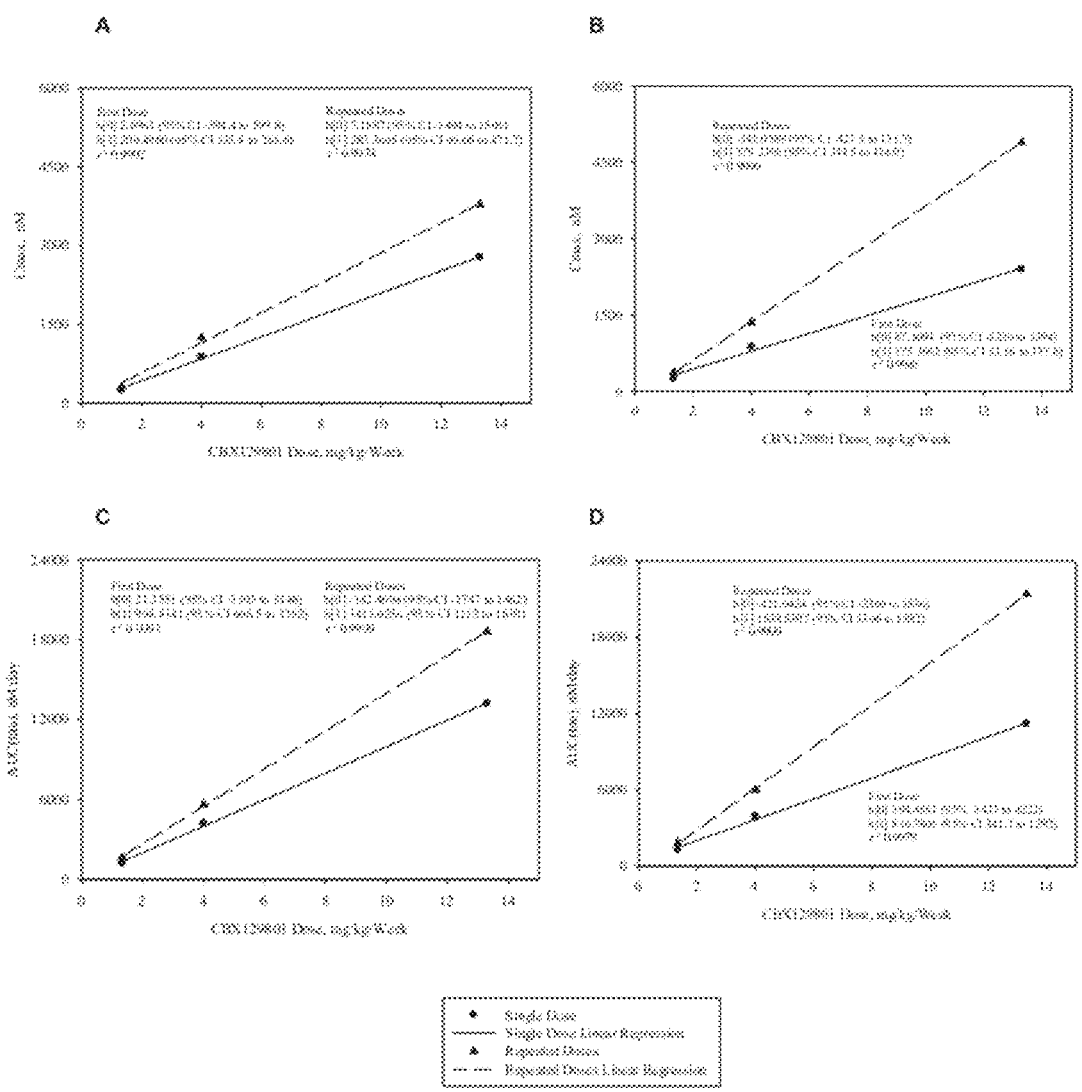
FIG. 15 shows the relationship between $C_{max}$ and $AUC_{(0-inf)}$ in Cynomolgus monkeys as a function of dose; Panel A $C_{max}$, first dose; Panel B $AUC_{(0-inf)}$ first dose; Panel C $C_{max}$, last dose; Panel D $AUC_{(0-inf)}$ last dose. The term "CBX129801" refers to the PEGylated C-peptide of Example 12. The term "$C_{max}$" refers to the maximum serum or plasma concentration of drug which occurs during the period of release which is monitored. The term $AUC_{(0-t)}$ refers to the area under the plasma concentration-time curve from time zero to the time of the last quantifiable concentration. The term "CBX129801" refers to the PEGylated C-peptide of Example 12. The term "$C_{max}$" refers to the maximum serum or plasma concentration of drug which occurs during the period of release which is monitored. The term $AUC_{(0-t)}$ refers to the area under the plasma concentration-time curve from time zero to the time of the last quantifiable concentration.

Results:

The mean plasma concentration-time profiles upon multiple dose s.c. administration by gender are illustrated in FIG. 14 with the corresponding PK parameters summarized in Table E8. The relationships between dose and the primary parameters of exposure (AUC and C$_{max}$) are shown FIG. 15.

TABLE E8

Summary of Pharmacokinetic Characteristics in Cynomolgus Monkeys Following Repeated-Dose Subcutaneous Administration (Weekly) for 28 Days

| | Male | | | Female | | | Pooled Gender | | |
|---|---|---|---|---|---|---|---|---|---|
| | Dose, mg/kg | | | | | | | | |
| | 1.33 | 4.0 | 13.3 | 1.33 | 4.0 | 13.3 | 1.33 | 4.0 | 13.3 |
| | First-Dose Parameters[a] | | | | | | | | |
| C$_{max}$, nM | 250 | 881 | 2,780 | 252 | 877 | 2,400 | 251 | 879 | 2,590 |
| T$_{max}$, day[b] | 2.00 | 1.00 | 2.00 | 2.00 | 2.00 | 2.00 | 2.00 | 1.50 | 2.00 |
| T$_{1/2}$, day | 4.67 | 3.30 | 2.85 | 3.33 | 3.53 | 2.63 | 4.00 | 3.42 | 2.74 |
| AUC$_{tau}$, nM · day | 1,180 | 4,210 | 13,200 | 1,280 | 3,920 | 11,200 | 1,230 | 4,060 | 12,200 |
| AUC$_{inf}$, nM · day | 1,920 | 5,770 | 17,700 | 1,800 | 5,410 | 14,400 | 1,860 | 5,590 | 16,000 |
| CL/F, mL/day/kg | 15.3 | 15.5 | 16.9 | 16.1 | 16.5 | 21.0 | 15.7 | 16.0 | 19.0 |
| V$_d$/F, mL/kg | 101 | 72.7 | 68.0 | 77.4 | 81.7 | 79.8 | 89.0 | 77.2 | 73.9 |
| C$_{max}$ M/F Ratio | 0.922 | 1.00 | 1.16 | — | — | — | — | — | — |
| AUC$_{tau}$ M/F Ratio | 0.922 | 1.07 | 1.18 | — | — | — | — | — | — |
| | Repeated-Dose Parameters[a] | | | | | | | | |
| C$_{max}$, nM | 308 | 1,250 | 3,780 | 371 | 1,350 | 4,900 | 340 | 1,300 | 4,340 |
| T$_{max}$, day[b] | 2.00 | 1.00 | 2.00 | 2.00 | 1.00 | 2.00 | 2.00 | 1.00 | 2.00 |
| T$_{1/2}$, day | 4.78 | 2.93 | 3.91 | 4.62 | 3.34 | 3.07 | 4.70 | 3.17 | 3.49 |

TABLE E8-continued

Summary of Pharmacokinetic Characteristics in Cynomolgus Monkeys Following
Repeated-Dose Subcutaneous Administration (Weekly) for 28 Days

|  | Male | | | Female | | | Pooled Gender | | |
|---|---|---|---|---|---|---|---|---|---|
|  | \multicolumn{9}{c}{Dose, mg/kg} |
|  | 1.33 | 4.0 | 13.3 | 1.33 | 4.0 | 13.3 | 1.33 | 4.0 | 13.3 |
| $AUC_{tau}$, nM·day | 1,650 | 5,610 | 18,600 | 1,860 | 6,000 | 21,400 | 1,750 | 5,810 | 20,000 |
| $AUC_{inf}$, nM·day | 2,740 | 7,330 | 28,300 | 2,910 | 8,240 | 28,300 | 2,820 | 7,790 | 28,300 |
| CLss/F, mL/day/kg | 18.3 | 15.7 | 15.8 | 15.9 | 14.7 | 13.6 | 17.1 | 15.2 | 14.7 |
| $V_d$ss/F, mL/kg | 121 | 67.8 | 86.0 | 110 | 71.4 | 61.0 | 116 | 69.6 | 73.5 |
| $C_{max}$ M/F Ratio | 0.830 | 0.926 | 0.771 | — | — | — | — | — | — |
| $AUC_{tau}$ M/F Ratio | 0.887 | 0.935 | 0.869 | — | — | — | — | — | — |
| Repeated/First Dose $C_{max}$ Ratio | 1.23 | 1.42 | 1.36 | 1.47 | 1.54 | 2.04 | 1.35 | 1.48 | 1.68 |
| Repeated/First Dose $AUC_{tau}$ Ratio | 1.40 | 1.33 | 1.41 | 1.45 | 1.53 | 1.91 | 1.42 | 1.43 | 1.64 |

[a]Refer to List of Abbreviations (Table A) for definition of terms;
[b]Expressed as median.

Overall, these results indicate that steady state is achieved by approximately Day 14. Exposure increased with increasing dose with peak plasma concentrations occurring between Day 1 and Day 2. AUC and $C_{max}$ following the first and last dose appear to be dose proportional over the range assessed with $AUC_{tau}$ at steady state approximately 30% to 90% higher than observed following the first dose. The $T_{1/2}$ appears similar across the 3 doses and following the first and last dose (~3 days). Systemic exposure in females was similar to that observed in males. Detectable drug levels persisted at both recovery doses (4.0 and 13.3 mg/kg/week) following cessation of dosing; however, the plasma concentrations of the PEGylated C-peptide markedly decreased over time and were substantially lower by the end of the recovery period for all doses (approximately 2-3 times the lower limit of quantitation). At the end of the recovery period, there was a modest ADA response at the lower two doses and a strong response at the high dose; however, as significant drug levels were present throughout and well after completion of dosing, the presence of antibodies did not meaningfully impact the monkeys' exposure to the PEGylated C-peptide.

Example 11

Effect on Nerve Conduction Velocity (NCV) in STZ Induced Diabetic Rats

To assess the effect of the PEGylated C-peptide on nerve conduction velocity in diabetic rats, the 40 kDa branched PEG (Example 12) was administered to STZ induced diabetic rats for 8 weeks. Results were also compared to those for unmodified human C-peptide, PEGylated rat C-peptide, which was coupled to the same 40 kDa branched PEG as described in Example 1, and unmodified rat C-peptide.

Protocols and Methods:

Streptozotocin (STZ) was administered I.V. at a dose of 50 mg/kg via the injection of 1 ml of a 50 mg/mL standard solution of STZ. Sprague Dawley male rats were obtained from Harlan. Rats had an average weight of around 400 g, fed a standard diet (TD2014) and housed individually in standard solid bottom 8-inch deep plastics with corn cob bedding. Animals were housed with a normal, 12 hours light, 12 hours dark light cycle and at an average temperature of 72±8° F. and relative humidity of: 30%-70% for the duration of the study. Animals were dosed for a period of 8 weeks, according to the dosing and formulations listed in Table E9.

TABLE E9

Summary of dosing protocols

| Grp | Compound | STZ Dose 50 mg/kg | Dose mg/kg | Dose Volume ml/kg | Route | Freq | # of An's | An #'s |
|---|---|---|---|---|---|---|---|---|
| 1 | Vehicle | No | 0 | 1 | SC | 1/wk** | 5 | 1-5 |
| 2 | Vehicle | Yes | 0 | 1 | SC | 1/wk** | 10 | 6-15 |
| 3 | PEGylated human C-peptide | Yes | 1 | 1 | SC | 1/wk** | 10 | 16-25 |

TABLE E9-continued

Summary of dosing protocols

| Grp | Compound | STZ Dose 50 mg/kg | Dose mg/kg | Dose Volume ml/kg | Route | Freq | # of An's | An #'s |
|---|---|---|---|---|---|---|---|---|
| 4 | PEGylated human C-peptide | Yes | 3 | 1 | SC | 1/wk** | 10 | 26-35 |
| 5 | Un modified Human C-peptide | Yes | 1.5* | pump | pump | Twice | 10 | 36-45 |
| 6 | Un modified Rat C-peptide | Yes | 0.3* | pump | pump | Twice | 10 | 46-55 |
| 7 | PEGylated rat C-peptide | Yes | 0.3 | 1 | SC | 1/wk** | 10 | 56-65 |
| | | | | | | TOTAL ANIMALS | | 65 |

*Per 24 hours;
**2/week in the first week of dosing.

The required dose of each drug administered to each animal was calculated based on the most recent body weight. Sterile phosphate-buffered saline was used as the vehicle.

Pretreatment Phase Study Conduct:

Prior to starting treatment animals were observed to identify any abnormalities, signs of pain or distress and any findings recorded, were discussed with a clinical veterinarian when observed. Body weights were determined before STZ treatment (day 1), for randomization to treatment groups, on day 7, and 11 and once weekly thereafter. Food Weights were determined pre-STZ (day 1), at randomization to treatment groups, and on days 7, and 11 and once weekly thereafter. Animals were randomized for the treatment phase based on C-peptide (<0.4 nM), whole blood glucose values (400-600 mg/dL) and body weight values. (See Table E5) Randomization was achieved using B.R.A.T. (block randomization allocation tool). Subcutaneous pump implants (Alzet pumps model 2mL4) were surgically implanted on day 10 and day 39.

Treatment Phase Study Conduct:

Blood was collected via a tail bleed on day 3 for randomization, day 7, day 11 and weekly thereafter for glucose and/or C-peptide. Animals were fasted for 6 hours prior to STZ injection, 3 hours prior to every glucose evaluation and fed ad lib for the remainder of the study. (See Table E10).

TABLE E10

Study Schedule

| Weekday | Day | Task |
|---|---|---|
| Monday | ~−7 | Animals arrive |
| Monday | 1 | 6 hour fast, body and food weights, IV administration of STZ (Zanosar) |
| Wednesday | 3 | 3 hour fast (6:00 am) prior to blood collection. Body and food weights. Tail bleed (9:00 am) for whole blood glucose evaluation in duplicate using glucometer and for EDTA plasma C-peptide analysis |
| Sunday | 7 | 3 hour fast (6:00 am) prior to blood collection. Body and food weights. Tail bleed (9:00 am) for whole blood glucose evaluation in duplicate using glucometer and for EDTA plasma C-peptide analysis |
| Monday | 8 | Randomize to treatment groups (am). Baseline NCV measurements (pm) |
| Tuesday | 9 | Baseline NCV measurements |
| Wednesday | 10 | Implantation of pumps and twice per week SC dosing (8:00 am) begins |
| Thursday | 11 | 3 hour fast (6:00 am) prior to blood collection. Body and food weights. Tail bleed (9:00 am) for whole blood glucose evaluation in duplicate using glucometer and for EDTA plasma C-peptide analysis (GROUPS 3, 4 and 7. The first five animals will be bleed 24 hours postdose, the second five will be bleed 48 hours postdose on day 12) |
| Friday | 12 | Blood collection for EDTA plasma on the second five animals from groups 3, 4 and 7-48 hour post dose collection. |
| Saturday | 13 | SC dosing (8:00 am) |
| Wednesday | 17 | 3 hour fast (6:00 am) prior to blood collection. Body and food weights. SC dosing (8:00 am). Tail bleed (9:00 am) for whole blood glucose evaluation in duplicate using glucometer and for EDTA plasma C-peptide analysis |
| Wednesday | 24 | 3 hour fast (6:00 am) prior to blood collection. Body and food weights. SC dosing (8:00 am). Tail bleed (9:00 am) for whole blood glucose evaluation in duplicate using glucometer and for EDTA plasma C-peptide analysis (GROUPS 3, 4 and 7. The |

TABLE E10-continued

Study Schedule

| Weekday | Day | Task |
|---|---|---|
| | | first five animals will be bleed 24 hours postdose, the second five will be bleed 48 hours postdose) |
| Thursday | 25 | Blood collection for EDTA plasma on the first five animals from groups 3, 4 and 7-24 hour post dose collection. |
| Friday | 26 | Blood collection for EDTA plasma on the second five animals from groups 3, 4 and 7-48 hour post dose collection. |
| Saturday | 27 | SC dosing (8:00 am) |
| Wednesday | 31 | 3 hour fast (6:00 am) prior to blood collection. Body and food weights. SC dosing (8:00 am). Tail bleed (9:00 am) for whole blood glucose evaluation in duplicate using glucometer. |
| Saturday | 34 | SC dosing (8:00 am) |
| Monday | 36 | 3 hour fast (6:00 am) prior to blood collection. Body and food weights. SC dosing (8:00 am). Tail bleed (9:00 am) for whole blood glucose evaluation in duplicate using glucometer and for EDTA plasma C-peptide analysis |
| Tuesday | 37 | NCV measurements |
| Wednesday | 38 | SC dosing (8:00 am), NCV measurements |
| Thursday | 39 | Removals of old pumps and implant new pumps. |
| Saturday | 41 | SC dosing (8:00 am) |
| Wednesday | 45 | 3 hour fast (6:00 am) prior to blood collection. Body and food weights. SC dosing (8:00 am). Tail bleed (9:00 am) for whole blood glucose evaluation in duplicate using glucometer |
| Saturday | 48 | SC dosing (8:00 am) |
| Wednesday | 52 | 3 hour fast (6:00 am) prior to blood collection. Body and food weights. SC dosing (8:00 am). Tail bleed (9:00 am) for whole blood glucose evaluation in duplicate using glucometer |
| Saturday | 55 | SC dosing (8:00 am) |
| Wednesday | 59 | 3 hour fast (6:00 am) prior to blood collection. Body and food weights. SC dosing (8:00 am). Tail bleed (9:00 am) for whole blood glucose evaluation in duplicate using glucometer |
| Saturday | 62 | SC dosing (8:00 am) |
| Monday | 64 | NCV measurements |
| Tuesday | 65 | NCV measurements |
| Wednesday | 66 | 3 hour fast (6:00 am) prior to blood collection. Body and food weights. SC dosing (8:00 am). Tail bleed (9:00 am) for whole blood glucose evaluation in duplicate using glucometer and for EDTA plasma C-peptide analysis Kidney Necropsy in the afternoon. |

Electrophysiologic Endpoints: Digital Nerve Action Potentials were recorded with the active recording electrode positioned at the ankle, behind the lateral malleolus and the stimulating cathode at the base of the second digit of the hindpaw. Velocity was calculated by dividing the distance between the stimulating cathode and the active electrode by the absolute onset latency of the initial depolarizing current.

Caudal Nerve Action Potentials were recorded with the active recording electrode positioned 10 mm below the hair line on the tail (determined visually) and the stimulating cathode 60-70 mm further distal. Velocity was calculated by dividing the distance between the stimulating cathode and the active electrode by the absolute onset latency of the initial depolarizing current.

Tibial Motor Conduction was recorded with the active electrode positioned in the intrinsic muscles of the hindpaw and the stimulating cathode proximal to the ankle, behind the lateral malleolus.

Preparation of Animals:

During all recording sessions, animals were anesthetized with isoflurane and placed in a prone position. Respiration and temperature was monitored during the electrophysiologic recording procedure.

Electrodes:

The placement of the active, reference and ground electrodes was tailored to each modality and positioned with respect to bony landmarks in each subject. Platinum needle electrodes (Grass-Telefactor, Co.), with impedances of approximately 50 kohms @ 1,000 Hz, were used as both active and reference leads for all PNS recordings.

Temperature Control:

Rectal temperature was maintained between 35.5 and 38.0 degrees C. throughout the recording sessions.

Data Processing:

Neuroelectric signals were impedance matched using unity gain preamplifiers, appropriately band-passed using multi-pole filters, and further differentially amplified using a gain factor of 0.5-50K. The filter settings were adjusted for each modality. Common mode rejection levels and gain factors were adjusted to minimize 60 Hz interference and to optimize the signal-to-noise ratio for each recording series. The amplified signal was time-locked to the evoking stimulus, multiplexed into selected channels and digitized at a rate greater than 5 times the highest frequency sampled. The data was scanned for artifacts (using a predetermined rejection level—80% of the digitized window) and digitally averaged for an epoch appropriate for the modality under study. The number of sweeps included in each average was adjusted for each measure to optimize the signal-to-noise ratio and facilitate the accurate assessment of both onset latency and peak amplitude measures.

Scoring of Data:

All electrophysiologic data was scored following optimization of the signal. Onset latency was measured from the stimulus artifact to the initiation of the depolarization to the nearest 0.01 msec; amplitude was measured from baseline to the peak of the depolarization to the nearest 0.01 µV for sensory responses, and to the nearest 0.01 mV for motor responses. All measurements were conducted with an internal computer cursor that follows the digitized trace. All wave forms were stored digitally and were available for further off-line analysis.

Calibration:

The amplifiers and filters were calibrated onsite on each day of electrophysiologic recordings.

Terminal Phase study conduct: Animals were anesthetized by $CO_2$ inhalation followed by cardiac puncture at specific time points.

Results:

Baseline measurements of Nerve Conduction Velocity (NCV)

Figure 16:
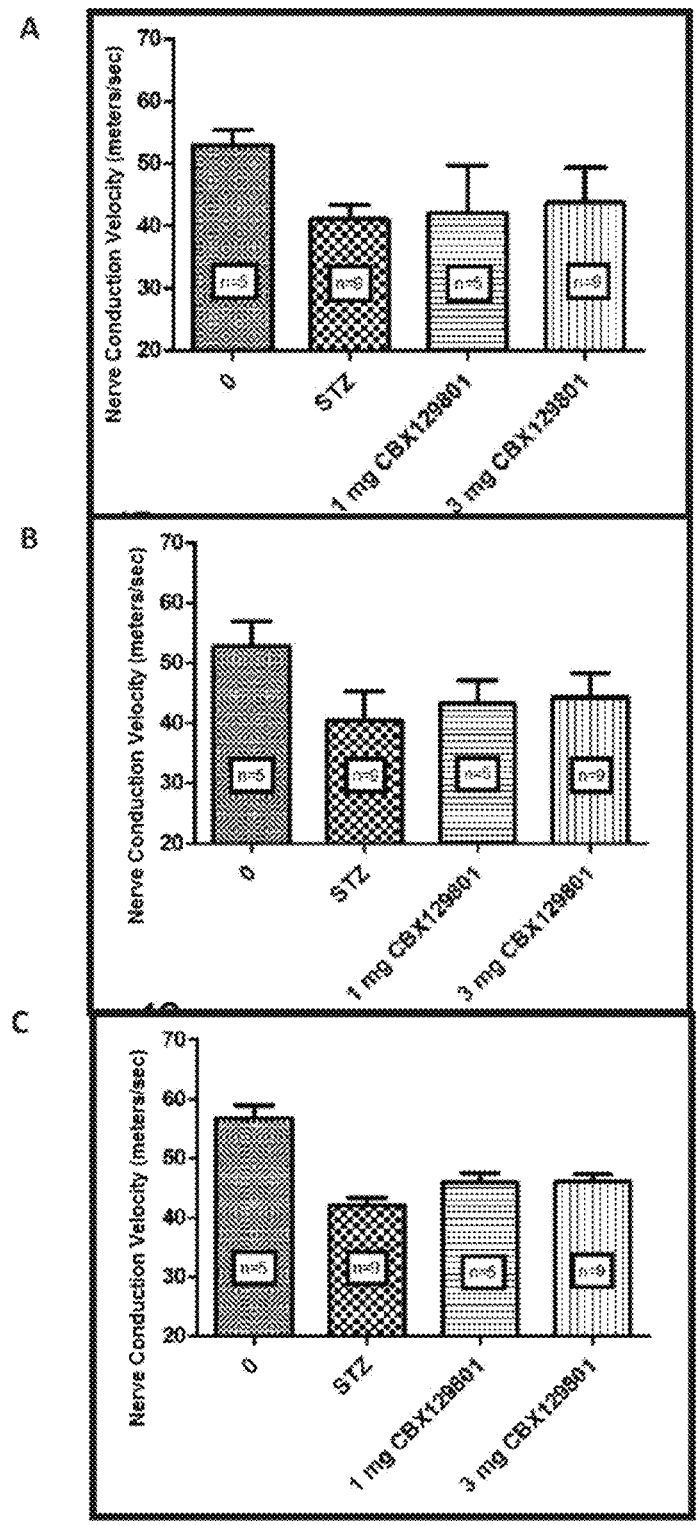
FIG. 16 shows the caudal Nerve Conduction Velocity (NCV, measured in meters/sec) in each of four treatment groups of rats treated for up to 8 weeks (See Example 6). In this figure, and the following three figures, Group 1 represents the vehicle control (no streptozotocin [STZ]), Group 2 represents the STZ treated group plus vehicle, Group 3 represents STZ plus 1.0 mg/kg/week (1.0 mg/ml) of human PEGylated C-peptide (Example 12), and Group 4 represents STZ plus 3.0 mg/kg/week (1.0 mg/ml) of human PEGylated C-peptide (Example 12).

The first NCV assessment occurred 8-9 days after the administration of STZ and after the presence of hyperglycemia was confirmed in each of the rats in Groups 2-4 (see Table E4 above). At that time point, which was prior to any administration of vehicle or PEGylated human C-peptide (ie., Baseline), there was clear and significant evidence of a STZ-induced peripheral polyneuropathy. At the Baseline assessment, maximal caudal NCV was reduced by slightly more than 10 msec (approximately 18%) in each of the STZ-treated groups compared to findings in the age-matched control group (FIG. 16A). At that time point, maximal digital NCV was reduced by 3-4 msec (FIG. 17A) and tibial distal latency was prolonged (consistent with slowed velocity) by approximately the same 10% value. Week 4 measurements of Nerve Conduction Velocity (NCV).

Figure 17:
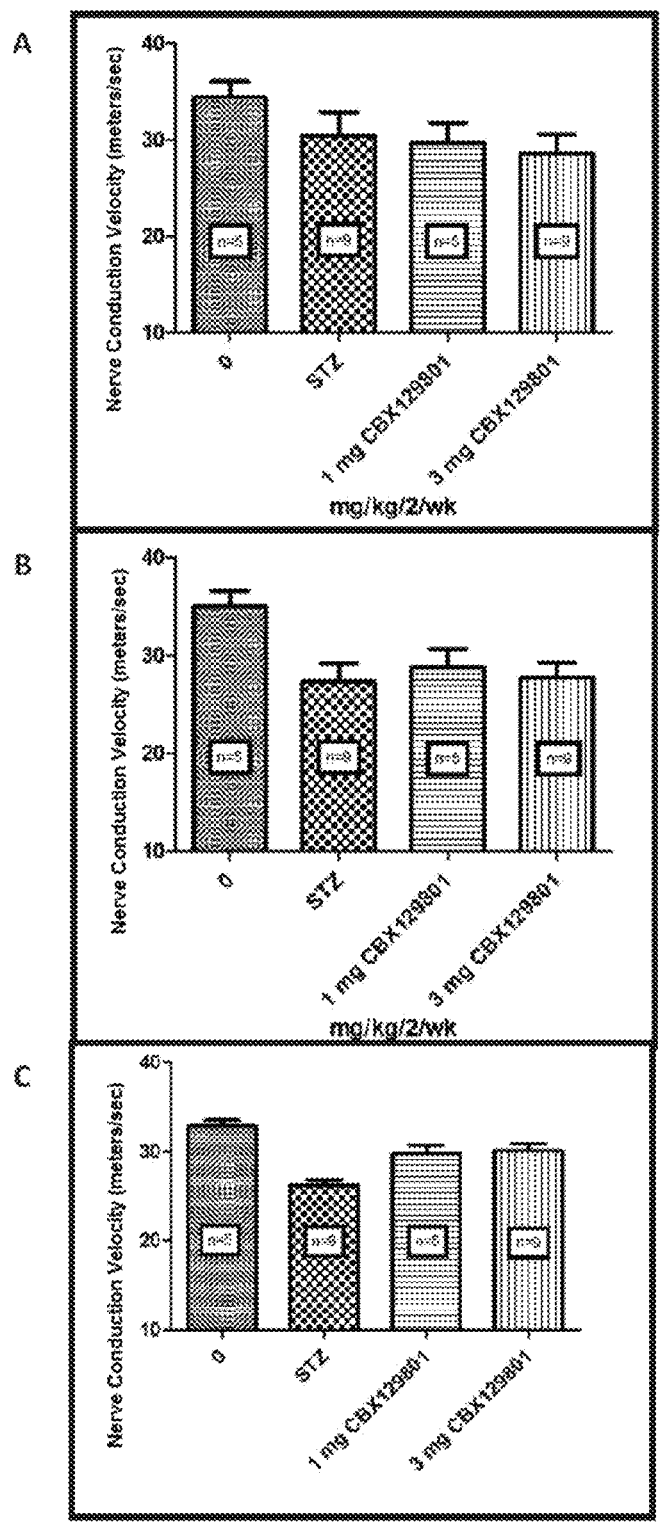
FIG. 17 shows the digital NCV (measured in meters/sec) in each of the same four groups of animals as described in FIG. 16.

FIGS. 16B and 17B illustrate the caudal and digital NCV in each of the four groups after a 4-week period (from Baseline) of administration of either vehicle alone or PEGylated human C-peptide at either 1.0 or 3.0 mg/kg/week. During this 4-week period, one rat in Group 2, five rats in Group 3 and one rat in Group 4 died. The Baseline values in FIGS. 16A and 17A have omitted data from these missing rats to keep the comparisons across the same subset of subjects.

Figure 18:
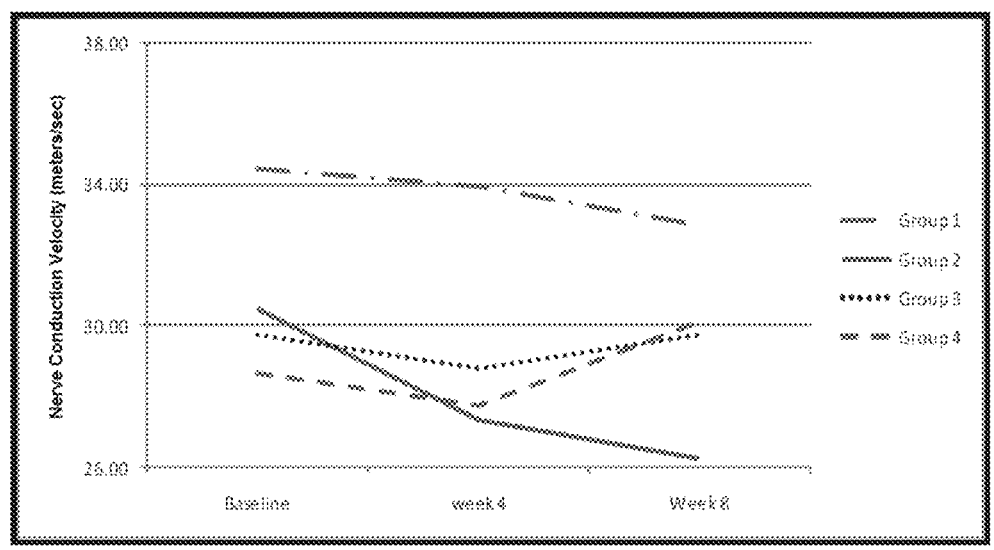
FIG. 18 shows the relative change in digital NCV (measured in meters/sec) in the same 4 treatment groups as described in FIG. 17, over the entire duration of the study.

NCV in the control group remained relatively constant for both the caudal and digital nerves over the examined 4-week period (FIG. 18). However, as expected, velocity in both the caudal and digital nerve continued to decrease in the STZ-only group. For the purely sensory distal digital nerve, there was an additional slowing of approximately 3 m/sec (10%) over the initial 4-week treatment period (FIG. 18). The continued slowing of NCV is consistent with progressive damage to the distal nerves due to the STZ-induced destruction of pancreatic beta cells, leading to hyperglycemia and endogenous C-peptide deficiency, which will eventually lead to altered transmembrane currents, changes in the micro-environment at the nodes, axonal atrophy, and ultimately to Wallerian degeneration.

The absolute latency of the tibial motor response was slightly longer at the Week 4 assessment in all groups, reflecting continued animal growth, however there was little or no difference across groups from this measure over the course of the initial four weeks of the study (data not shown).

NCV decreased at a slower rate compared to the findings in the STZ only group for the survivors in each of the groups co-treated with PEGylated human C-peptide over the 4-week period from Baseline (FIG. 18). However at the 4-week time point the effects were small.

Week 8 Measurements of Nerve Conduction Velocity (NCV)

Figure 19:
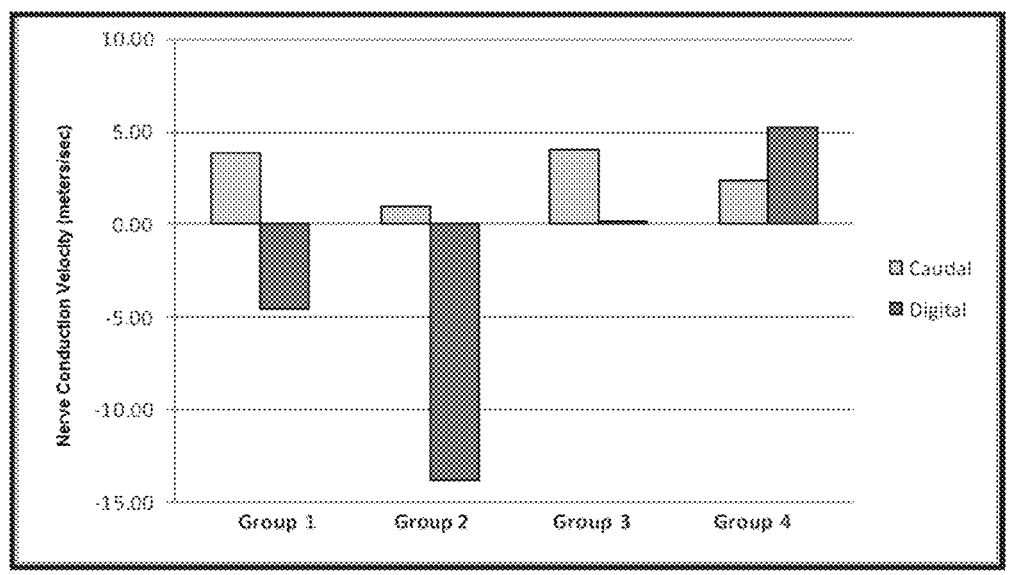
FIG. 19 shows the relative change in caudal and digital NCV (measured in meters/sec) in the same 4 treatment groups as described in FIGS. 16 and 17, compared to baseline measurements after 8 weeks of treatment.

FIGS. 16C and 17C illustrate the caudal and digital NCV in each of the four groups at the 8 week time point. Over the study period, NCV in the control group for the mixed caudal nerve increased by approximately 4 m/sec (7%) from Baseline values (FIG. 19). This change is consistent with the well documented continued post-natal increases in myelin and axonal cross-sectional diameter. No additional animals in any group died between the $4^{th}$ and $8^{th}$ week of the post Baseline assessment.

There was relatively little change in the NCV for the digital nerve in the control group over the 8-week period from baseline (FIGS. 18 and 19). In contrast, NCV in the STZ only group (Group 2) continued to decline over this period. This progressive deterioration is consistent with the continued insult induced by hyperglycemia and lack of endogenous C-peptide production. By Week 8, digital NCV in the STZ-only group was decreased by >4 m/sec (14%) from Baseline and by more than 20% from values in the age-matched control group. In contrast, digital nerve NCV was either stable (Group 3) or actually improved (Group 4) over the 8 week study period in the groups co-treated with PEGylated human C-peptide (FIG. 18).

Tables E11 and E11 outline the percent change in the digital and caudal NCV, respectively from the Baseline to the 8-week assessment time point.

TABLE E11

Percent change in the digital NCV
Digital Nerve NCV (m/sec)

| | Baseline | Week 4 | Week 8 | Change from Baseline to Week 8 |
|---|---|---|---|---|
| Control (No STZ) | 34.4 | 34.0 | 32.9 | −4.4% |
| Vehicle Control(No PEGylated C-peptide) | 30.5 | 27.3 | 26.2 | −14.1% |
| PEGylated human C-peptide (1 mg/kg/week) | 29.7 | 28.8 | 29.8 | +0.3% |
| PEGylated human C-peptide (3 mg/kg/week) | 28.6 | 27.8 | 30.1 | +5.2% |

TABLE E12

Percent change in the caudal NCV
Caudal Nerve NCV (m/sec)

| | Baseline | Week 4 | Week 8 | Change from Baseline to Week 8 |
|---|---|---|---|---|
| Control (No STZ) | 53.0 | 52.9 | 56.8 | +7.2 |
| Vehicle Control (No PEGylated C-peptide) | 41.1 | 40.3 | 42.1 | +2.4 |
| PEGylated human C-peptide (1 mg/kg/week) | 42.1 | 43.2 | 46.1 | +9.5 |
| PEGylated human C-peptide(3 mg/kg/week) | 43.8 | 44.3 | 46.1 | +5.3 |

Conclusions:

There was a substantial slowing of both the digital and caudal NCV in the groups treated with STZ (Groups 2-4) compared to the age-matched control group (Group 1). These effects were evident at Baseline, 8-9 days after the administration of the STZ, but prior to the co-administration of PEGylated C-peptide.

A progressive slowing of NCV was documented for the digital nerve over the 8 week study period in the group treated with STZ only. The co-administration of PEGylated C-peptide, at either 1.0 or 3.0 mg/kg/week, prevented this continued deterioration. In the group co-treated with 3.0 mg/kg/week of PEGylated C-peptide there was even slight improvement of digital nerve NCV in the 8 week period following an STZ-induced neuropathy.

The results from this study clearly suggest that over the time period examined, the co-treatment with PEGylated C-peptide provided neuroprotection against the neuropathy induced by STZ alone. This effect was especially evident for the purely sensory digital nerve. Due in part to the early loss of subjects, this study provides only initial insights into dose-related different in the benefits of PEGylated C-peptide, but there is a suggestion in the digital data supporting slightly greater benefits for the high dose group.

The caudal nerve data demonstrated a substantial negative impact of the STZ treatment which was manifest at Baseline in Groups 2-4. There was no further evidence of slowing in caudal NCV during the 8 week study period. However, there was improvement in velocity for the two groups co-treated with PEGylated C-peptide that approximated the trend in the control group (Table E12). The improvement in Groups 3 and 4 were greater than that observed in the STZ only group. As was the case for Week 4 there is little change in the tibial motor responses across groups (data not shown).

These results demonstrate that the biological activity of the native C-peptide is retained when the peptide is PEGylated, which extends its circulating half-life and thereby lessens the frequency of replacement dosing. The average maximum plasma concentration assessed 2 days after dosing in the third week in the low-dose, and high-dose PEGylated human C-peptide, and PEGylated rat C-peptide groups was approximately 129 nM, 431 nM, and 12 nM, respectively (data not shown). The average minimum plasma concentration at the end of the study was approximately 22 nM, 94 nM, and 2 nM in the low-dose and high-dose PEGylated human C-peptide, and PEGylated rat C-peptide groups, respectively. It is concluded that PEGylated human C-peptide retains the beneficial biological properties of the unmodified C-peptide, and is effective for both the treatment and prevention of the long complications of diabetes, In particular the current experiments establish that human PEGylated C-peptide is effective for the treatment of neuropathies associated with diabetes.

Example 12

GMP Batch Preparation of Pegylated C-Peptide

Overview

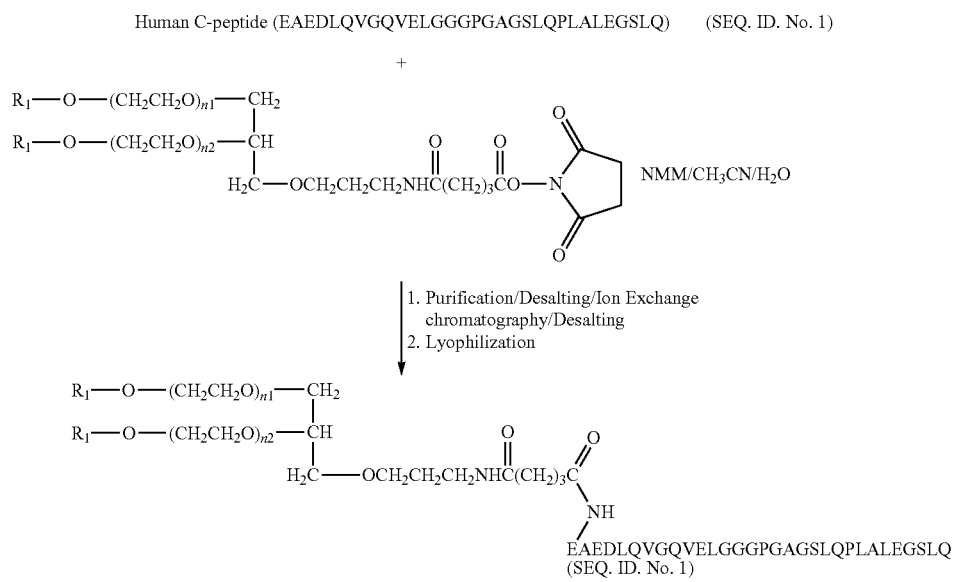

PEGylation:

The synthesis of the human PEGylated C-peptide was carried out in a single step by coupling of the N-terminus of the human C-peptide (sodium salt) with the branched, approx. 40 kDa-NHS ester PEG derivative (SUNBRIGHT® GL2-400GS2 (NOF Corporation) in the presence of N-methyl morpholine.

SUNBRIGHT® GL2-400GS2 (115 g) is first dissolved in 600 mL of a solution of (50/50) acetonitrile/water. The resulting solution was stirred and charged with another solution containing human C-peptide (7.9 g) in a solution of 175 mL of acetonitrile/water, followed by addition of 1.2 mL of N-Methyl Morpholine (NMM). Addition of NMM was repeated several times at ~1 hr intervals, with the progress of the reaction monitored by HPLC prior to each addition. This process was repeated about 8 to 10 times and then the reaction was stirred overnight for about 8 to 12 hrs. The resulting reaction mixture was carried on to the purification step once the reaction was verified as complete by HPLC analysis. Typically during this process several sub-lots were prepared and then combined for purification as described below.

Purification of crude PEGylated C-peptide by preparative Reversed Phase Chromatography The crude PEGylated C-peptide solution was diluted with 6 volumes in 0.1% TFA/water. The pH was adjusted to a pH of <3 and purified by preparative HPLC using reverse phase silica (Diasogel C-18, 15 μm, 300 Angstrom). The adsorbed PEGylated C-peptide was eluted from the column by applying a gradient of acetonitrile in dilute aqueous TFA (Buffer A is 0.1% TFA, Buffer B is 100% ACN: 0 to 25% B in 5 minutes, then 25% to 50% B during 100 minutes and then hold until the product is eluted). The eluate was monitored by UV at 230 nm. Fraction with purity of ≥90, NSI>6.0% are pooled. Fractions with purity >70% maybe recycled.

Desalting and Purification of PEGylated C-Peptide by Preparative Reversed Phase Chromatography The combined pure fractions obtained from the preceding step were desalted and purified by preparative HPLC using reverse phase silica. The column was washed with dilute aqueous TFA, followed by dilute aqueous ammonium acetate. The PEGylated C-peptide was then eluted from the column by applying a gradient of acetonitrile in dilute aqueous AcOH (Buffer A is 2% acetic acid, Buffer B is 100% ACN: 0 to 25% B in 5 minutes, then 25% to 50% B during 75 minutes and then hold until the product is eluted). The eluate was monitored by UV at 230 nm. The pure fractions obtained from chromatography were pooled (purity ≥95%, NSI >3.0%) and lyophilized. Fractions with purity >80% maybe recycled for further purification.

Ion Exchange Purification of PEGylated C-Peptide by Preparative HPLC

The crude lyophilized PEGylated Human C-peptide from the step above (~180 g) was dissolved in 5% acetonitrile/water and applied to an ion exchange column (DEAE52 Cellulose). The column was then washed with ~50 L of water and the product was eluted off the column with ~40 L of an aqueous solution of sodium chloride (1M)/ammonium acetate (1M). The eluate was monitored by UV at 230 nm. The pure fractions obtained from the chromatography were pooled (≥92% purity; no single impurity (NSI)>4%) and carried on for desalting/purification. Fractions with purity >80% maybe recycled.

Desalting and Purification of CBX129801 by Preparative Reversed Phase Chromatography The pure fractions from the ion exchange chromatography step were diluted with an equal volume of water and applied to a preparative HPLC column (silica). The column was then washed with dilute 2% acetic acid (1BV) and the product eluted with a solution of acetonitrile in dilute acetic acid (Buffer A is 2% acetic acid, Buffer B is 100% ACN: 0 to 25% B in 5 minutes, then 25% to 50% B during 50 minutes and then hold until the product is eluted). The eluate was monitored by UV at 230 nm. The pure fractions (purity ≥95%, NSI >3.0%) obtained from chromatography were pooled and lyophilized. Fractions with purity >80% maybe recycled.

Lyophilization of PEGylated C-Peptide

The product from the preceding purification was reconstituted at a concentration of about 15-20 g/L in 2% aqueous acetic acid and lyophilized to give the pure PEGylated C-peptide drug substance as its free acid.

Example 13

Biophysical Characterization of PEGylated C-Peptide

A batch of the PEGylated C-peptide prepared as described in Example 12 above, with purity of 99.5%, as determined by RP-HPLC with UV detection, was used in the analytical investigations described below unless noted otherwise. The structural studies conducted are listed in Table E13. All analyses confirm the chemical structure of the drug substance.

TABLE E13

Structural testing performed

| Test | Analytical Technique |
| --- | --- |
| Molecular mass | MALDI-TOF MS |
| Identity | FT-IR |
| Identity and ratios of individual amino acids | Amino acid analysis for DS |
| Identity and chirality of individual amino acids | Chiral amino acid analysis |
| Molecular mass and sequence of amino acids (performed at the FI stage) | CID-MS/MS |
| Peptide Mapping (to confirm sequence on PEGylated peptide) | Chymotrysin digest followed by HPLC and MS/MS analysis of fragments |
| Absence of Counter ion | Ion chromatography, RP-HPLC, ICP-MS |

In addition to the structure elucidation tests, described above, additional characterization studies were performed on the PEGylated C-peptide described in Example 12 above, and these additional studies are listed in Table E14.

Molecular Mass by MS:

Matrix Assisted Laser Desorption Ionization-Time of Flight (MALDI-TOF) was used to verify the molecular mass of the drug substance. The sample gave a positive ion MALDI-TOF mass spectrum with a broad singly-charged pseudomolecular ion cluster observed centered approximately at m/z 45743.

Figure 20:
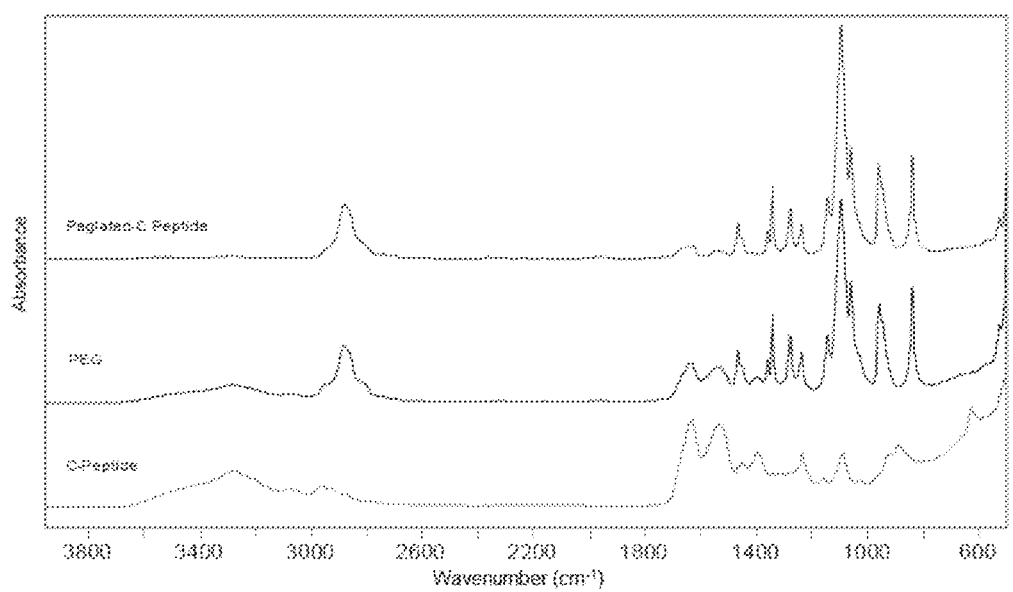
FIG. 20 shows a Fourier Transform Infrared Spectroscopy (FT-IR): of C-peptide, the PEG reagent, and PEGylated C-peptide. The term "cm$^{-1}$" refers to the wavenumber, or inverse wavelength of light indicated by the spectrogram.
Figure 21:
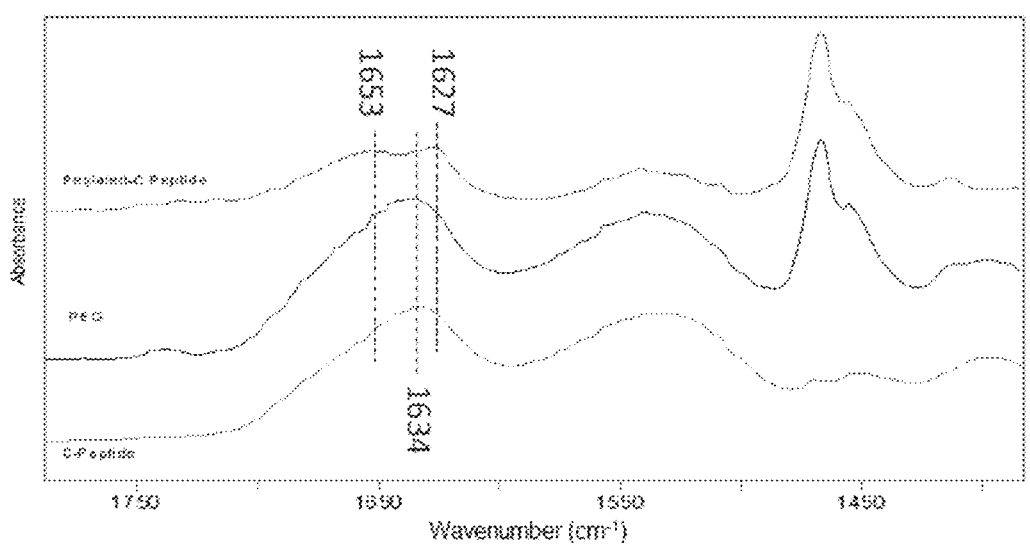
FIG. 21 shows an expanded region of the Fourier Transform Infrared Spectroscopy (FT-IR): of C-peptide, the PEG reagent, and PEGylated C-peptide. The term "cm$^{-1}$" refers to the wavenumber, or inverse wavelength of light indicated by the spectrogram.

Fourier Transform Infrared Spectroscopy (FT-IR):

FT-IR spectra of C-peptide, the PEG reagent, and PEGylated C-peptide were collected on a Jasco 4200 FT-IR spectrometer equipped with a TGS detector and a single-bounce ZnSe crystal mounted on a ATR accessory. Solid samples were pressed against the Zn Se crystal with a Teflon rod. Residual moisture peaks were subtracted from the spectra. The results are shown in FIG. 20 and FIG. 21 (expanded region). The spectrum of PEGylated C-peptide is very similar to the spectra of the PEG reagent. This is not surprising given the mass ratio of peptide to PEG.

However, there is a slight difference in the amide I region as shown in FIG. 21. Specifically, the amide I bands of PEGylated C-peptide show two peaks at 1627 and 1653 cm$^{-1}$, while the spectrum of free C-peptide only exhibits one broad amide I band peak at 1634 cm$^{-1}$. An amide I band near 1630 cm$^{-1}$ is normally associated with β-sheet structures or β-turns, while an amide I band near 1650 cm$^{-1}$ is normally assigned to α-helix, irregular, or random coil structures. The appearance of an absorbance at 1653 cm$^{-1}$ is consistent with a more random structure for the PEGylated peptide compared to C-peptide.

Figure 22:
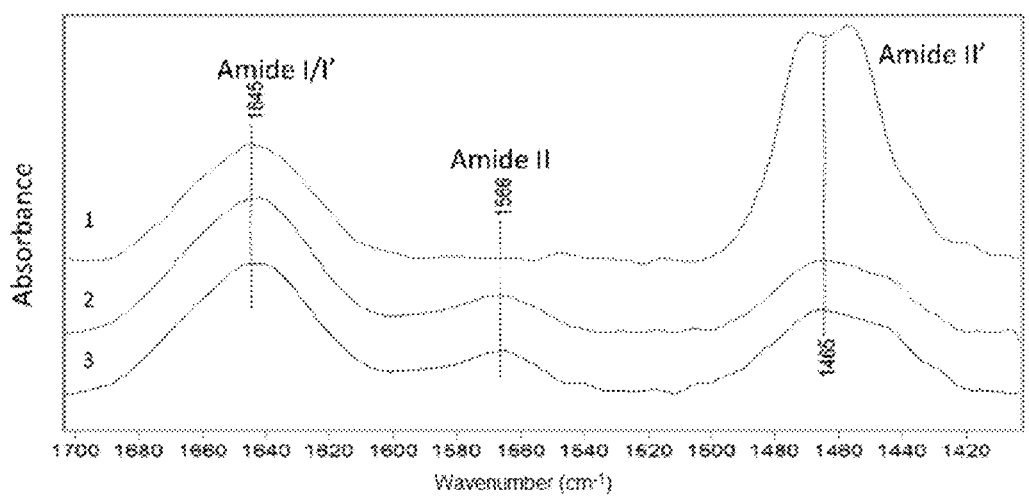
FIG. 22 shows a Fourier Transform Infrared Spectroscopy (FT-IR): of C-peptide, the PEG reagent, and PEGylated C-peptide collected in $D_2O$. The term "cm$^{-1}$" refers to the wavenumber, or inverse wavelength of light indicated by the spectrogram.
Figure 23:
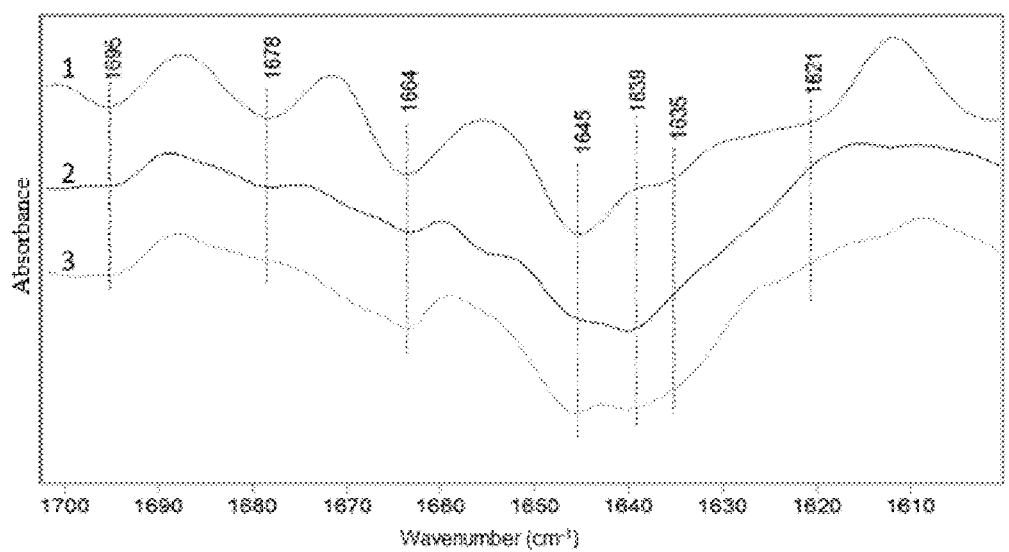
FIG. 23 shows a Fourier Transform Infrared Spectroscopy (FT-IR): of C-peptide, the PEG reagent, and PEGylated C-peptide collected in $D_2O$. The term "cm$^{-1}$" refers to the wavenumber, or inverse wavelength of light indicated by the spectrogram.

To investigate if the difference in the amide I region is due to differences in hydrogen bonding between amide groups and solvent water, the FT-IR spectra were collected in $D_2O$ as shown in FIG. 22 and FIG. 23. For the collection of $D_2O$ spectra, sample in $D_2O$ solution was placed between two $CaF_2$ windows with a 6 µm spacer.

The FT-IR spectrum of PEGylated C-peptide in $D_2O$ shows minimum amide II band intensity (at 1566 cm$^{-1}$), which indicates all amide groups undergo H-D exchange. Upon H-D exchange, the amide II band is shifted from 1566 to 1465 cm$^{-1}$ (becomes an amide II' band). There is remaining amide II intensity for free C-peptide at both higher (~25 mg/mL) and lower concentrations (~12.5 mg/mL) in D$_2$O, which indicates some un-exchanged amide groups. The un-exchanged amide groups are likely protected by either intra-molecular hydrogen bonds within beta-turns or inter-molecular hydrogen bonds formed among peptide oligomers (aggregates) at high concentration. For the PEGylated C-peptide in D$_2$O, the effective C-peptide concentration is much lower because of the low mass ratio of C-peptide to the 40 kDa PEG.

However, as can be seen from the second derivative FT-IR spectra (shown in FIG. 23), the amide I' band for the high concentration sample of C-peptide (~25 mg/mL) shows a major peak at 1639 cm$^{-1}$, with a shoulder at 1645 cm$^{-1}$, whereas the low concentration sample (~12.5 mg/mL) shows major peaks at both 1639 cm$^{-1}$ and 1645 cm$^{-1}$. This indicates the difference in the amide I' region may be concentration related. In comparison to the spectrum of PEGylated C-peptide, the spectra of free C-peptide shows more intensity near 1635-1640 cm$^{-1}$, indicating more β-turn structures in free C-peptide. It should be noted that signal to noise was poor for more dilute samples of C-peptide samples precluding assessment of lower concentrations.

Identity and Ratio of Individual Amino Acids by Amino Acid Analysis:

To ensure the identity and the correct ratio of the constituent amino acids, amino acid analysis was performed on the PEGylated C-peptide prepared in Example 12. This method involves hydrolyzing the peptide in strong acid, separating the amino acids on an ion-exchange column, and, finally, detecting the eluents after ninhydrin derivatization. The results of the study are shown in Table E14. The results from the amino acid analysis confirm the identity and theoretical relative occurrence of amino acids in the PEGylated C-peptide within experimental error.

TABLE E14

Results of amino acid analysis

| Amino Acid | Theoretical Relative Occurrence | Observed Relative Occurrence |
|---|---|---|
| Asp | 1 | 1.1 |
| Pro | 2 | 2.1 |
| Ser | 2 | 2.2 |
| Glx* | 8 | 6.9 |
| Gly | 7 | 7.3 |
| Ala | 3 | 3.0 |
| Val | 2 | 2.0 |
| Leu | 6 | 6.5 |

Notes:
*Glx = results from Gln + Glu.

Identity and Chirality of Individual Amino Acids by GC:

Chiral amino acid analysis of Example 12 was performed to investigate the chiral identity of the constituent amino acid residues. The peptide is hydrolyzed in deuterated solvents (DCl/D$_2$O), derivatized as the N(O,S)-fluoroacetyl amino acid esters, and analyzed with GC-MS to determine each amino acid enantiomer. GC was performed using a deactivated glass capillary coated with Chirasil-Val. The carrier gas was hydrogen. The results are shown in Table E15. The values obtained confirm the chirality expected for the amino acids constituting the structure of the PEGylated C-peptide of Example 12.

TABLE E15

Results of chiral amino acid analysis

| Amino Acid | Content of L-amino Acid (%) |
|---|---|
| Asp | >99.9 |
| Pro | 99.86 |
| Ser | 99.51 |
| Glx | >99.9 |
| Ala | 99.9 |
| Val | >99.9 |
| Leu | 99.89 |

Sequence of Amino Acids by MS/MS:

Given the large size and polydispersity of the PEG, sequencing by MS/MS is performed at the Final Intermediate stage. The amino acid sequence of the PEGylated C-peptide of Example 12 was investigated by performing MS/MS using CID (Collision Induced Dissociation), a technique in which the intact sample molecule is deliberately fragmented with the intention of gaining structural information from the product ion spectrum created by the process.

The types of fragment ions observed in a MS/MS spectrum depend on many factors including primary sequence, the amount of internal energy, how the energy was introduced, charge state, etc. The accepted nomenclature for fragment ions was first proposed by Roepstorff and Fohlman [*Biomedical Spectrometry*, 1984, 11(11): 601], and subsequently modified by Johnson et al. [*Annals of Chemistry*, 1987, 59(21): 2621-2625].

Fragments will only be detected if they carry at least one charge. If this charge is retained on the N-terminal fragment, the ion is classed as either a, b, or c. If the charge is retained on the C-terminal, the ion type is either x, y, or z. A subscript indicates the number of residues in the fragment.

In addition to the proton(s) carrying the charge, c ions and y ions abstract an additional proton from the precursor peptide. Thus, six singly-charged sequence ion are possible. Note that these structures include a single charge-carrying proton. In electrospray ionization, peptides generally carry two or more charges, so that fragment ions may carry more than one proton.

The expected, multiply-charged b and y and fragment ions were calculated using a computer program developed by Croker et al. [*Journal of Biomolecular Techniques*, 2000, volume 11, issue 3, 135-141]. The results are shown in Tables E16 and E17. Fragmentation and sequence analysis by MS/MS and MS/MS/MS confirmed the suggested primary sequence of the PEGylated C-peptide of Example 12 final intermediate.

TABLE E16

Summary of MS Fragmentation and sequence analysis

| Sequence | | N-terminal Ion Series | | | | | |
|---|---|---|---|---|---|---|---|
| Example 12 | Pos. | Expected $b^{1+}$ | Observed m/z | Expected $b^{2+}$ | Observed m/z | Expected $b^{3+}$ | Observed m/z |
| Glu | b1 | 130.1 | — | 65.5 | — | 44 | — |
| Ala | b2 | 201.1 | 201.1 | 101.1 | — | 67.7 | — |
| Glu | b3 | 330.1 | 330.1 | 165.6 | — | 110.7 | — |
| Asp | b4 | 445.2 | 445.1 | 223.1 | — | 149.1 | — |
| Leu | b5 | 558.2 | 558.2 | 279.6 | — | 186.8 | — |
| Gln | b6 | 686.3 | 686.2 | 343.7 | — | 229.4 | — |
| Val | b7 | 785.4 | 785.3 | 393.2 | — | 262.5 | — |
| Gly | b8 | 842.4 | 842.3 | 421.7 | — | 281.5 | — |
| Gln | b9 | 970.5 | 970.4 | 485.7 | — | 324.2 | — |
| Val | b10 | 1069.5 | 1069.5 | 535.3 | — | 357.2 | — |
| Glu | b11 | 1198.6 | 1198.4 | 599.8 | — | 400.19 | — |
| Leu | b12 | 1311.6 | 1311.6 | 656.3 | — | 437.9 | — |
| Gly | b13 | 1368.7 | 1368.6 | 684.8 | 684.8 | 456.9 | — |
| Gly | b14 | 1425.7 | 1425.6 | 713.4 | 713.3 | 475.9 | — |
| Gly | b15 | 1482.7 | 1482.6 | 741.9 | 741.8 | 494.9 | — |
| Pro | b16 | 1579.8 | | 790.4 | — | 527.3 | — |
| Gly | b17 | 1636.8 | 1636.8 | 818.9 | 818.8 | 546.3 | — |
| Ala | b18 | 1707.8 | 1707.8 | 854.4 | 854.3 | 569.9 | — |
| Gly | b19 | 1764.8 | 1764.9 | 882.9 | 882.8 | 589 | — |
| Ser | b20 | 1851.9 | 1851.8 | 926.4 | 926.4 | 618 | — |
| Leu | b21 | 1965 | 1964.9 | 983 | 982.9 | 655.7 | — |
| Gln | b22 | 2093 | — | 1047 | 1046.9 | 698.3 | — |
| Pro | b23 | 2190.1 | — | 1095.5 | — | 730.7 | — |
| Leu | b24 | 2303.2 | — | 1152.1 | 1151 | 768.4 | — |
| Ala | b25 | 2374.2 | — | 1187.6 | 1187.5 | 792.1 | — |
| Leu | b26 | 2487.3 | — | 1244.1 | 1244.1 | 829.8 | — |
| Glu | b27 | 2616.3 | — | 1308.7 | 1308.6 | 872.8 | — |
| Gly | b28 | 2673.3 | — | 1337.2 | 1337.1 | 891.8 | — |
| Ser | b29 | 2760.4 | — | 1380.7 | 1380.6 | 920.8 | — |
| Leu | b30 | 2873.5 | — | 1437.2 | 1437.1 | 958.5 | 958.3 |
| Gln | b31 | 3001.5 | — | 1501.3 | 1501.2 | 1001.2 | — |
| OH | — | — | — | — | — | — | — |

TABLE E17

Summary of MS Fragmentation and sequence analysis

| Sequence | | C-terminal Ion Series | | | | | |
|---|---|---|---|---|---|---|---|
| Example 12 | Pos. | Expected $y^{1+}$ | Observed m/z | Expected $y^{2+}$ | Observed m/z | Expected $y^{3+}$ | Observed m/z |
| Glu | y31 | 3019.5 | — | 1510.3 | 1510.3 | 1007.2 | 1007.2 |
| Ala | y30 | 2890.5 | — | 1445.7 | — | 964.2 | — |
| Glu | y29 | 2819.4 | — | 1410.2 | — | 940.5 | — |
| Asp | y28 | 2690.4 | — | 1345.7 | 1345.5 | 897.5 | — |
| Leu | y27 | 2575.4 | — | 1288.2 | 1288.1 | 859.1 | — |
| Gln | y26 | 2462.3 | — | 1231.7 | 1231.5 | 821.4 | — |
| Val | y25 | 2334.2 | — | 1167.6 | 1167.5 | 778.8 | — |
| Gly | y24 | 2235.2 | — | 1118.1 | 1117.9 | 745.7 | — |
| Gln | y23 | 2178.1 | — | 1089.6 | 1089.4 | 726.7 | — |
| Val | y22 | 2050.1 | — | 1025.5 | — | 684 | — |
| Glu | y21 | 1951 | 1951 | 976 | 975.9 | 651 | — |
| Leu | y20 | 1822 | 1821.9 | 911.5 | 911.4 | 908 | — |
| Gly | y19 | 1708.9 | 1708.8 | 855 | — | 570.3 | — |
| Gly | y18 | 1651.9 | 1651.9 | 826.4 | 826.4 | 551.3 | — |
| Gly | y17 | 1594.8 | 1594.9 | 797.9 | 797.8 | 532.3 | — |
| Pro | y16 | 1537.8 | 1537.8 | 769.4 | 769.3 | 513.3 | — |
| Gly | y15 | 1440.8 | — | 720.9 | — | 480.9 | — |
| Ala | y14 | 1383.8 | 1383.7 | 692.4 | — | 461.9 | — |
| Gly | y13 | 1312.7 | 1312.6 | 656.9 | — | 438.2 | — |
| Ser | y12 | 1255.7 | 1255.6 | 928.4 | — | 419.2 | — |
| Leu | y11 | 1168.7 | 1168.6 | 584.8 | — | 390.2 | — |
| Gln | y10 | 1055.6 | 1055.5 | 528.3 | — | 352.5 | — |
| Pro | y9 | 927.5 | 927.5 | 464.3 | — | 309.8 | — |
| Leu | y8 | 830.5 | — | 415.7 | — | 277.5 | — |
| Ala | y7 | 717.4 | 717.3 | 359.2 | — | 239.8 | — |

TABLE E17-continued

Summary of MS Fragmentation and sequence analysis

| Sequence Example 12 | Pos. | C-terminal Ion Series | | | | | |
|---|---|---|---|---|---|---|---|
| | | Expected $y^{1+}$ | Observed m/z | Expected $y^{2+}$ | Observed m/z | Expected $y^{3+}$ | Observed m/z |
| Leu | y6 | 646.3 | 646.3 | 323.7 | — | 516.1 | — |
| Glu | y5 | 533.3 | 533.2 | 267.1 | — | 178.4 | — |
| Gly | y4 | 404.2 | 404.2 | 202.6 | — | 135.4 | — |
| Ser | y3 | 347.2 | 347.2 | 174.1 | — | 116.4 | — |
| Leu | y2 | 260.2 | 260.2 | 130.6 | — | 87.4 | — |
| Gln | y1 | 147.1 | — | — | — | 49.7 | — |
| OH | — | — | — | — | — | — | — |

Peptide Mapping:

A peptide map is a fragmentation pattern generated by digestion of a protein with proteolytic enzymes. The pattern of peptide fragments is characteristic of a particular protein and may be used to identify structure. A method for mapping C-peptide was previously developed and four fragments were identified by mass spectrometry. The four fragments contain amino acids 25-31 (labeled as fragment A), 13-24 (labeled as fragment B), 1-12 (labeled as fragment C), and 1-24 (labeled fragment as D) as shown on the bottom panel of FIG. 24.

Figure 24:
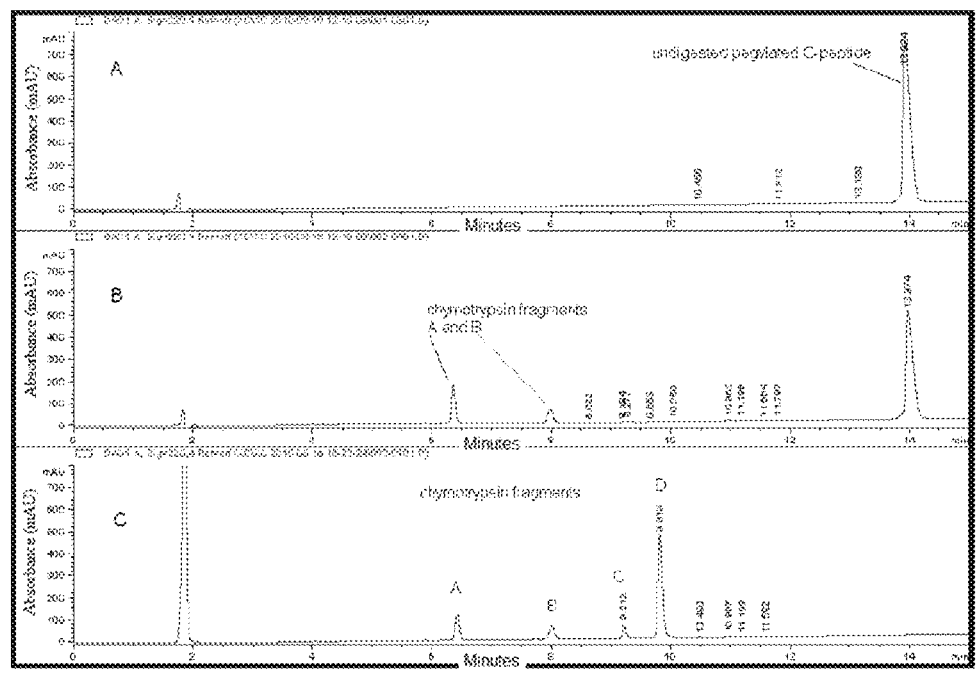
FIG. 24 shows a peptide map for C-peptide (1 mg/mL) and PEGylated C-peptide (10 mg/mL) after incubation with chymotrypsin.

A side-by-side comparison was performed wherein C-peptide (1 mg/mL) and PEGylated C-peptide (10 mg/mL) were dissolved in 25 mM ammonium bicarbonate buffer. To each 1 mL of sample, 40 μL of 0.25 mg/mL chymotrypsin was added and the samples were incubated for four hours at 37° C. The digestion was stopped by the addition of formic acid, and the samples were analyzed by RP-HPLC. The results are shown in FIG. 24.

As expected for PEGylated C-peptide, fragment C (1-12) and D (1-24) were not observed since the PEG moiety is attached at the N-terminus. Fragments 25-31 and 13-24 were observed for the PEGylated C-peptide of Example 12. To investigate whether the peak at 14 minutes was undigested PEGylated C-peptide, a time course study for the digestion was performed over 27 hours. No additional fragments were obtained consistent with the digestion going to completion. In addition, a 50/50 mixture of undigested PEGylated C-peptide and digested PEGylated C-peptide was analyzed by RP-HPLC with an extended gradient to see if any separation could be achieved; however, only a single peak was observed. Therefore it is concluded that the peak at 14 minutes contains PEGylated 1-12 and 1-24 fragments and possibly some intact PEGylated C-peptide of Example 12. The inability to resolve these fragments is not unexpected since the chromatographic behavior of the molecule is dominated by the large PEG moiety.

Absence of Counterion:

The ammonium content was measured by Ion Chromatography (IC), acetic acid by HPLC, and sodium content by ICP/MS to assure little or no counter ion remained after the desalting procedure.

The ammonium content was determined to be 0.035% w/w, and the sodium content was found to be 0.02% w/w, below the specification limit.

Although the levels of counterions in the drug substance were low, when calculated on a molar basis, may be indicative of some association of ammonia (0.9 molar ratio) and or sodium (0.4 molar ratio) to the final drug substance.

Sedimentation Velocity by Analytical Ultracentrifugation:

To assess the homogeneity and distribution of any aggregates in PEGylated C-peptide, the sedimentation velocity was measured in an analytical ultracentrifuge. Using this technique, aggregates can be detected on the basis of their different sedimentation coefficients. Sedimentation velocity is an absolute method based on simple physical principles. Its calibration is based on fundamental units of length and time, requiring no standard molecules as reference. Sedimentation coefficients depend on molecular shape as well as molecular mass, thus it is not possible to predict the sedimentation coefficient for an oligomer even when the monomer sedimentation coefficient is known.

Figure 25:
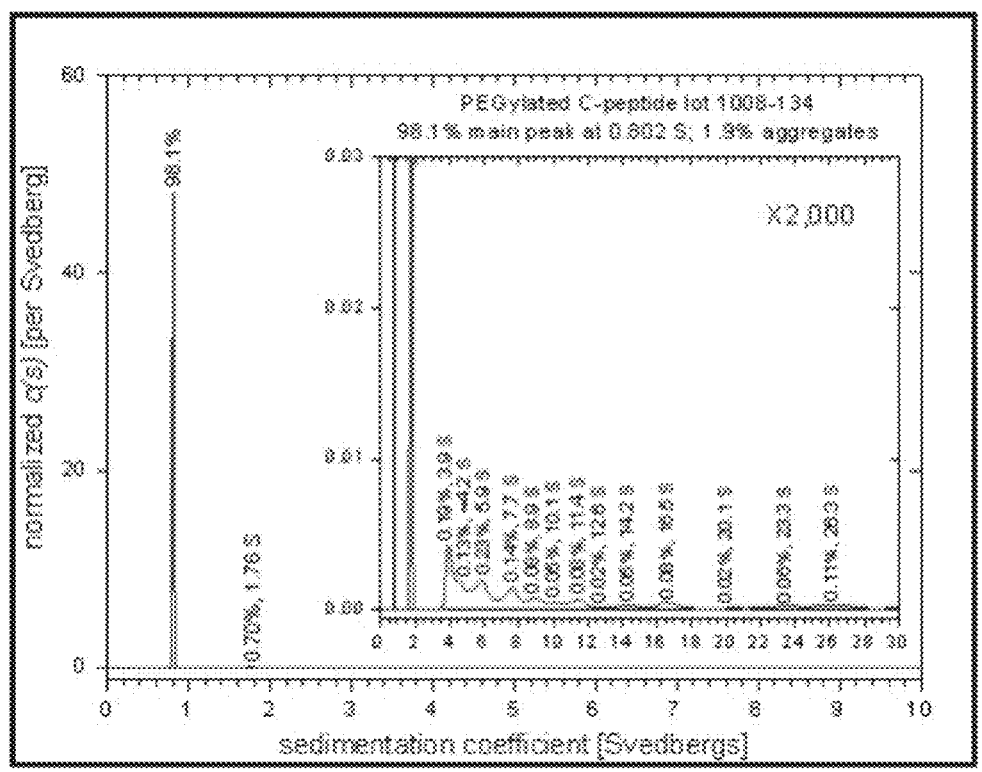
FIG. 25 shows the normalized sedimentation coefficient distribution for PEGylated C-peptide (at ~0.6 mg/mL) in PBS buffer.

The normalized sedimentation coefficient distribution for PEGylated C-peptide lot 1008-134 (at ~0.6 mg/mL) in PBS buffer is shown in FIG. 25. The main peak at 0.802 S is 98.1%, indicating the sample is homogenous. The sedimentation coefficient of C-peptide (unPEGylated) was previously determined to be in the range of ~0.4-0.5 S, No signal in this range was detected, indicating there is no free C-peptide. In addition, the sedimentation coefficient is consistent with a 40 kDa branched PEG (0.82 S).

Circular Dichroism Analysis of C-Peptide and PEGylated C-Peptide:

Near and far UV Circular Dichroisn (CD) analysis was performed on C-peptide and PEGylated C-peptide. Samples were dissolved in 20 mM phosphate buffer containing 4.7% sorbitol, pH 6.0 at 1 mg/mL for C-peptide and ~10.4 mg/mL for PEGylated C-peptide (equivalent to 0.69 mg/mL of C-peptide). The solvent subtracted spectrum was converted to the mean residue ellipticity using the peptide concentration (1 or 0.69 mg/mL), the mean residue weight (97.4) and the path-length of the cell (1 cm for the absorbance measurement or 0.02 cm for the CD). Measurements were carried out on a Jasco J-715 spectropolarimeter.

Figure 26:
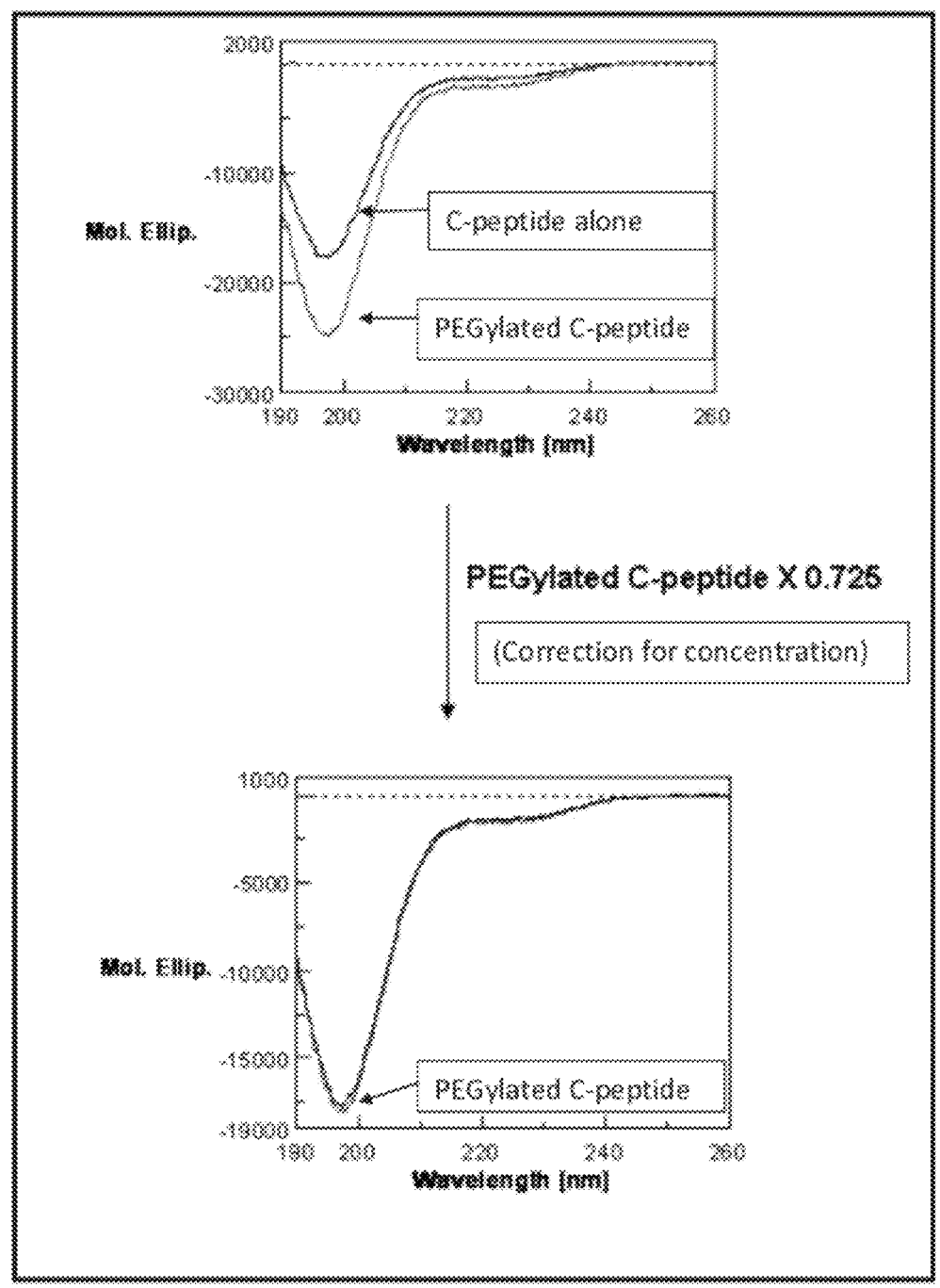
FIG. 26 shows a Circular Dichroism Analysis of C-peptide and PEGylated C-peptide.

As shown in FIG. 26, the mean residue ellipticity of C-peptide (upper line and PEGylated C-peptide (lower line) in the near UV region is essentially zero for both samples as there are no aromatic groups and disulfide bonds (shown in the upper panel of FIG. 26).

The far UV CD spectra of C-peptide and PEGylated C-peptide show the secondary structure is largely disordered. There is no double minima at 220 and 208 nm typical for a α-helix and no valley at 217 nm typical for anti-parallel β-sheet.

CD analysis shows a nearly identical spectral shape for C-peptide and PEGylated C-peptide when corrected for concentration (lower panel of FIG. 26) (note there is some error in the concentration estimates as the sample weights were not corrected for water or salts/solvents). Therefore, it can be concluded that PEGylation does not alter the secondary structure of the peptide.

Figure 27:
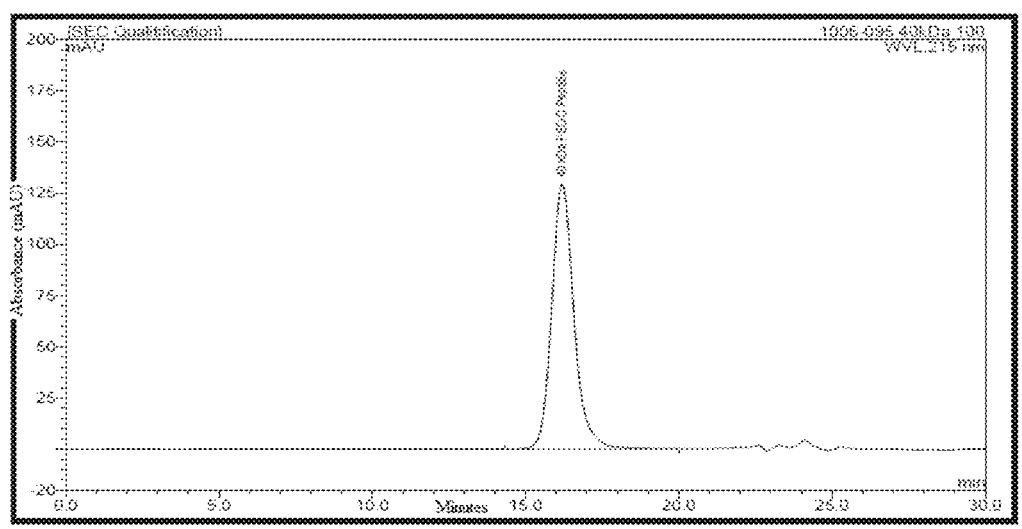
FIG. 27 shows the results of Size Exclusion Chromatography (SEC) of a sample of the PEGylated C-peptide of Example 12.

Size Exclusion Chromatography (SEC):

A sample of the PEGylated C-peptide of Example 12 (100 μg in 20 mM phosphate buffer, 4.7% sorbitol, pH 6.0) was analyzed by size exclusion chromatography as shown in FIG. 27.

Figure 28:
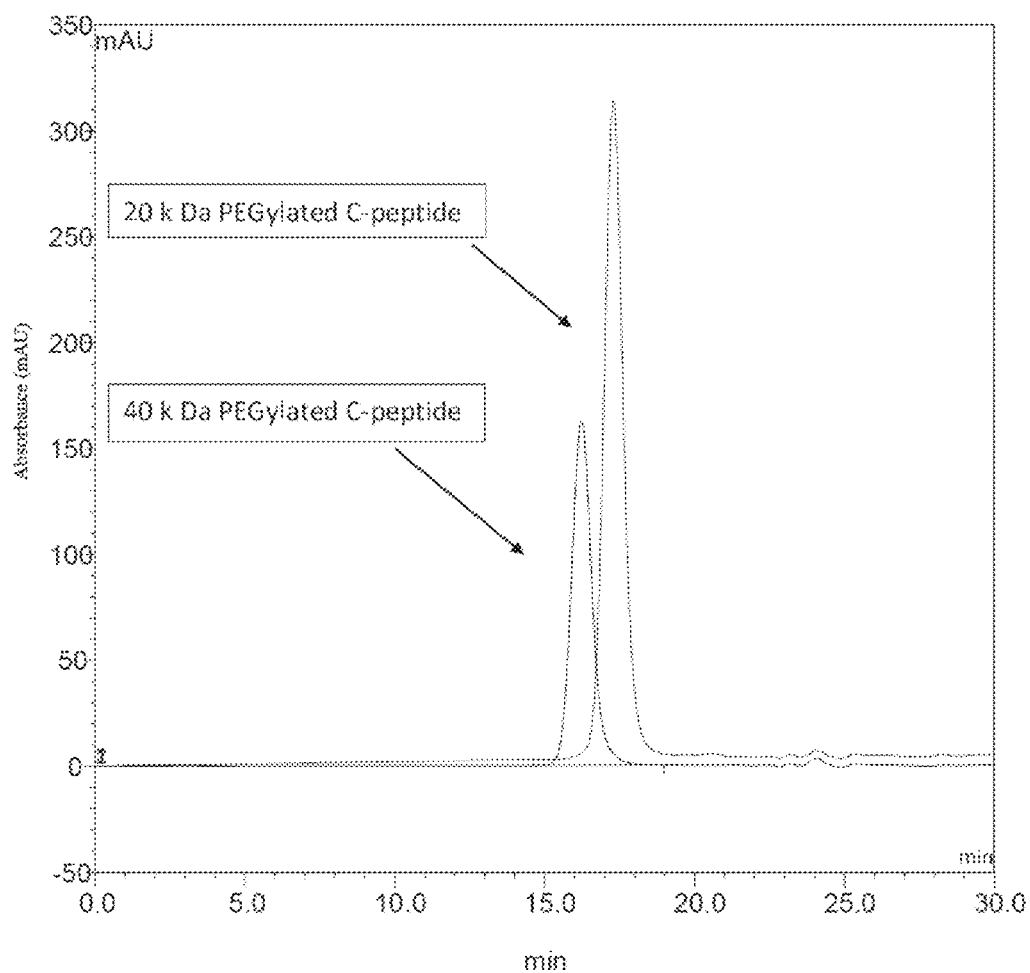
FIG. 28 shows an overlay of the chromatogram of the 20 kDa PEGylated C-peptide and 40 kDa PEGylated C-peptide of Example 12.

As part of the SEC method qualification, a 20 kDa PEGylated peptide was independently synthesized and analyzed by SEC to show the method was capable of distinguishing related compounds based on size. An overlay of the chromatogram of the 20 kDa PEGylated C-peptide (both samples at 100 μg load, in the same buffer system) with the PEGylated C-peptide of Example 12 is shown in FIG. 28. As can be seen in FIG. 28, peaks of lower molecular weight elute later from the SEC column. The absence of peaks before the main peak indicates there are no appreciable levels of higher molecular weight species present in the PEGylated C-peptide of Example 12. Similarly, the absence of peaks after the main peak indicates there are not appreciable levels of lower molecular weight species.

Figure 29:
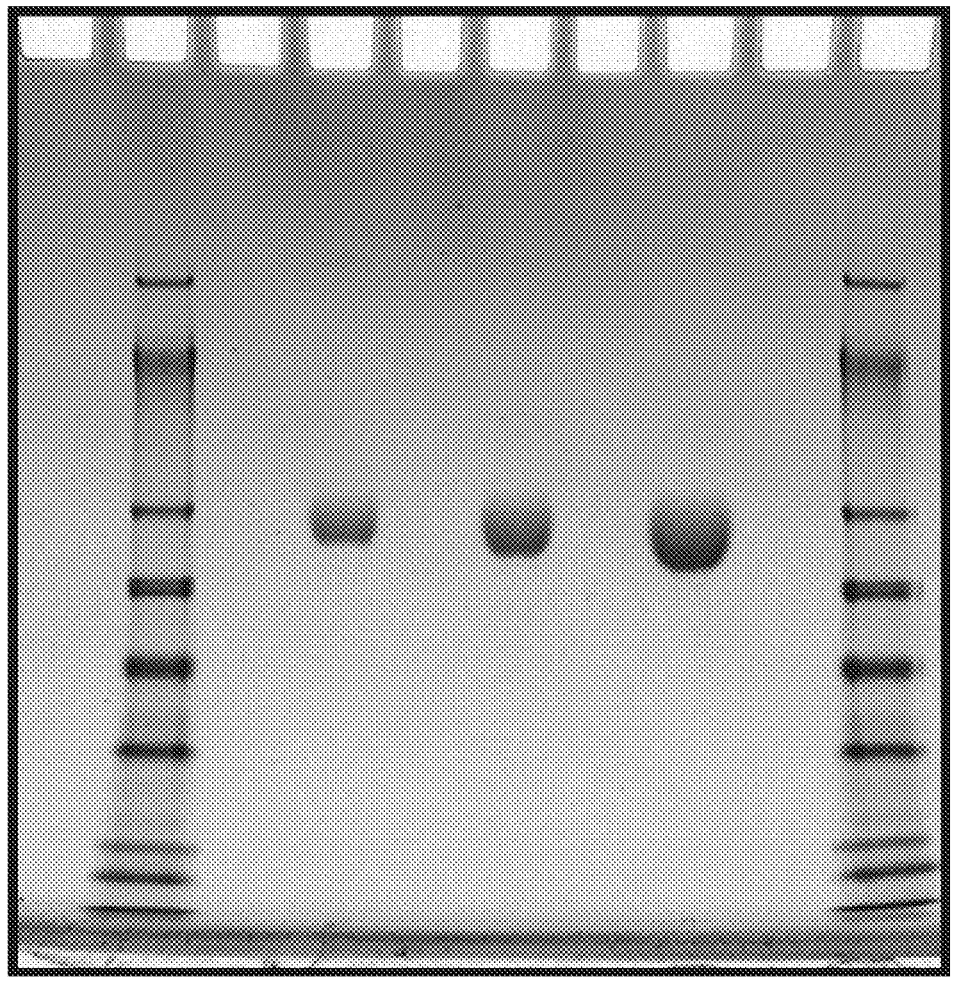
FIG. 29 shows the results of sodium dodecyl sulfate polyacrylamide gel electrophoresis SDS-PAGE: Gel electrophoresis of the PEGylated C-peptide of Example 12.

SDS-PAGE:

Gel electrophoresis was conducted using a 4-12% Tris-Glycine gel. Molecular weight standards (see Blue Plus2, Prestained Standards from Invitrogen) were applied in Lanes 2 and 10 as displayed in FIG. 29. Different amounts of PEGylated C-peptide ranging from 2 μg to 10 μg were applied to the gel in Lanes 4, 6, and 8. A single intense band between 64-98 kDa was visualized by Coomassie staining. The hydrodynamic radius of PEG is known to be greater than the size predicted based on the molecular weight of the protein markers. Therefore, this result is not unexpected. The SDS-PAGE results also show the absence of other higher molecular weight impurities.

Activity Profiling:

Samples of PEGylated C-peptide, were compared to authentic unlabeled C-peptide to confirm that the PEGylated product retained the activity of the unlabelled peptide.

Methods:

Human Kidney (HK2) cells were seeded at a density of 20,000 cells/well in (non-coated) 96 well (bl/cl) plates and incubated for 48 hours. On the day of the experiment, HK2 cells were washed and starved in DMEM+0.5% BSA for 1 hour. Cells were treated with 1 nM (final concentration) with ten replicates for 5 minutes. C-Peptide PEG GMP (lot #1-FIN-0988, C-Peptide PEG Tox (1007-119), C-Peptide PEG Tox (1008-090), unmodified C-Peptide (209400-3) and C-Peptide PEG reference (1008-134) were added in equal volumes. Plates were spun at 1000 rpm for 5 minutes. The total treatment time was 7-10 minutes. Immediately after treatment, cells were fixed with 2% (final) paraformaldehyde and permeabilized with ice-cold methanol. Cells were then treated with anti-pERK antibody and the plates were processed using the IF+Tyramide amplification, following standard protocols.

Figure 30:
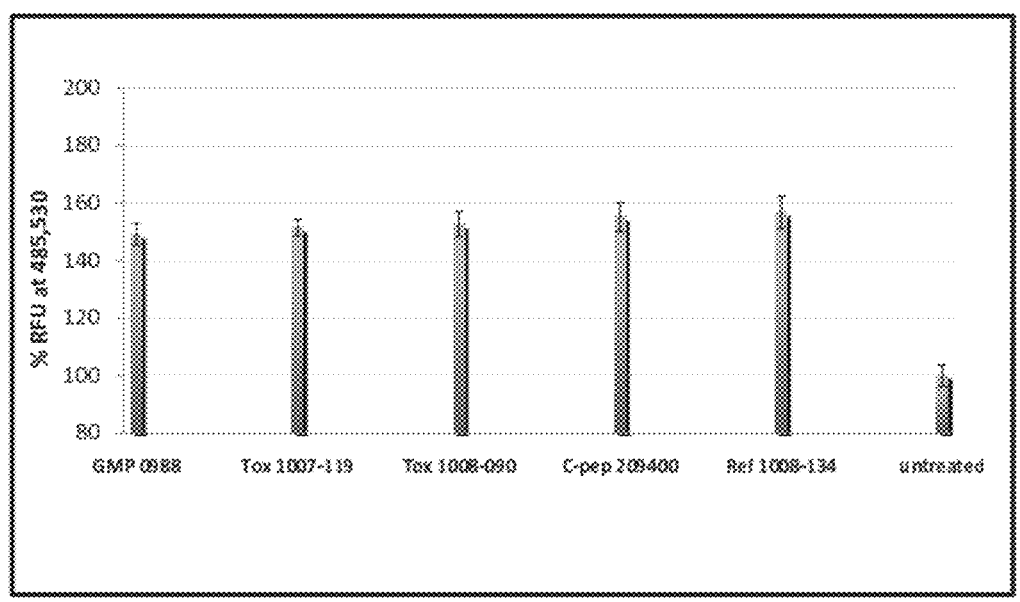
FIG. 30 shows the results of an assessment of the biological activity of the PEGylated C-peptide compared to native C-peptide in the ERK phosphorylation assay. The terms "GMP 09888," "Tox 1007-119," "Tox 1008-090," "C-pep 209400," and "Ref 1008-134" refer to unique lots of the PEGylated C-peptide of Example 12.

Results:

The results shown in FIG. 30, demonstrate that the PEGylated C-peptide retains the activity of the un-PEGylated product, and this activity is consistent across several different lots of C-peptide.

Example 14

Pharmaceutical Development

Since the PEGylated C-peptide (Example 1) is formulated as an aqueous solution, key physicochemical properties that can affect the performance of the formulation are solubility of the drug substance, pH, ionic strength, and tonicity. All of these factors may impact the stability of the PEG portion of the PEGylated C-peptide and have been evaluated here.

At 20 mg/mL, the drug substance is well below the solubility limit in the formulation buffer (up to 100 mg/mL). Excipients that are compatible with the drug substance have been selected to optimize the stability of the product as described below. The excipients used in the drug product are sodium phosphate (monobasic and dibasic), sorbitol, sodium hydroxide, and distilled Water for Injection. All excipients are compendial and meet the standards outlined in the USP. The choice of excipients and their levels are described in this example.

Buffer Selection:

Phosphate buffer was selected for initial evaluation because it is commonly used in pharmaceutical preparations and has good buffering capacity at physiological pH. A pH screening study was conducted by dissolving ~1 mg/mL of PEGylated C-peptide (Example 12) in 10 mM sodium phosphate buffer at varying pH (6.0, 6.5, 7.0, and 7.5). Samples were stored at 40° C. for 9 days and then analyzed by RP-HPLC. All samples were significantly degraded (~40% or more), consistent with degradation of the PEG component of the peptide-PEG conjugate. In addition, the pH of all formulations shifted downward by 0.7-1.0 pH units indicating there was insufficient buffering capacity. Nevertheless, a clear trend could be observed with increased stability at lower pH. Namely the formulation starting at pH 6.0 was preferred over 6.5, 7.0, and 7.5, respectively. Therefore a target pH of 6.0 was selected.

Tonicity Agent:

A second formulation study was conducted to select a tonicity agent (saline or sorbitol). The concentration of saline (0.9%) or sorbitol (4.7%) was selected to make the drug product solution isotonic. The PEGylated C-peptide (Example 1) (1 mg/mL) was dissolved in 20 mM sodium phosphate buffer with either saline (0.9%) or sorbitol (4.7%). The pH was adjusted to 6.0. Samples were stored at 5° C. and at 40° C. The stability of these formulations was greatly improved by the addition of a tonicity agent (data not shown). After 4 weeks at 40° C., both tonicity agents gave equivalent results with a drop in area-% purity of ~2-3%. After 12 weeks at 40° C., the sorbitol-containing formulation was clearly superior, with a drop in area-% purity of ~7% compared to the saline-containing formulation which showed a drop in area-% purity of ~72% (corresponding to PEG degradation). At 5° C., little to no degradation was observed in either formulation after 12 weeks. Based on the accelerated stability results, sorbitol was selected as the tonicity agent.

Ionic Strength:

A third formulation study was conducted to evaluate the impact of ionic strength on the stability of the formulation. Solutions of PEGylated C-peptide (Example 12) were prepared at ~20 mg/mL in phosphate buffer at 10, 20, and 50 mM containing 4.7% sorbitol and adjusted to pH 6.0. Samples were stored at 5° C. and 40° C. The results are summarized in Table E18.

TABLE E18

Stability of PEGylated C-peptide (Example 12) as a function of buffer concentration

| Buffer Concentration | Initial | | | 3 months at 5° C. | | | 3 months at 40° C. | | |
|---|---|---|---|---|---|---|---|---|---|
| | Content (mg/mL) | Purity (%) | pH | Content (mg/mL) | Purity (%) | pH | Content (mg/mL) | Purity (%) | pH |
| 10 mM | 22.3 | 99.4 | 5.9 | 21.4 | 99.3 | 6.0 | 8.1 | 40.3 | 4.1 |
| 20 mM | 21.4 | 99.8 | 6.0 | 21.3 | 99.4 | 6.1 | 4.0 | 22.3 | 4.0 |
| 50 mM | 22.1 | 99.9 | 6.1 | 21.1 | 99.6 | 6.2 | 4.2 | 21.8 | 4.9 |

At 5° C., all formulations looked similar after 3 months. There was no appreciable change in pH content or area-% purity. At 40° C., there was a decrease in pH, purity, and content for all formulations. The best results were obtained for the 10 mM phosphate concentration, indicating high ionic strength may negatively impact stability. Therefore, 10 mM phosphate was selected as the buffer concentration.

From the foregoing description, one skilled in the art can easily ascertain the essential characteristics of this invention, and without departing from the spirit and scope thereof, can make various changes and modifications of the invention to adapt it to various usages and conditions.

We claim:

1. A polyethylene glycolated (PEGylated) C-peptide having the following structure:

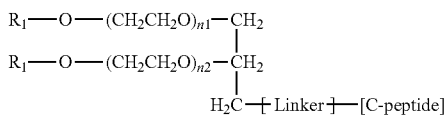

wherein:

C-peptide is -EAEDLQVGQVELGGGPGAGSLQPLA-LEGSLQ (SEQ ID NO: 1);

each $R_1$ is methyl;

n1 is 200 to 800;

n2 is 200 to 800;

the linker is selected from the group consisting of: $-X_1-(CH_2)_{m4}-CO-$ and
$-X_1-(CH_2)_{m2}-X_2-CO-(CH_2)_{m4}-CO-$;

wherein $X_1$ is $-O-$ or missing;

$X_2$ is $-NH-$;

$m_2$ is 1 to 5; and $m_4$ is 1 to 5;

wherein the linker is attached to the N-terminal amino group of the C-peptide;

wherein the molecular weight of the PEGylated C-peptide without the C-peptide portion is about 40 kDa to about 50 kDa;

or a pharmaceutically acceptable salt thereof;

and wherein the PEGylated C-peptide is for parenteral administration.

2. The PEGylated C-peptide of claim 1, wherein the linker is $X_1-(CH_2)_{m2}-X_2-CO-(CH_2)_{m4}-CO-$.

3. A pharmaceutical composition for parenteral administration comprising the PEGylated C-peptide of claim 1 and a pharmaceutically acceptable carrier or excipient.

4. The pharmaceutical composition of claim 3, wherein the pharmaceutically acceptable carrier or excipient is sorbitol.

5. The pharmaceutical composition of claim 4, wherein the sorbitol is present at a concentration of about 2% to about 8% wt/wt.

6. The pharmaceutical composition of claim 5, wherein the sorbitol is present at a concentration of about 4.7% wt/wt.

7. The pharmaceutical composition of claim 6, wherein the composition is buffered to a pH within the range of about pH 5.5 to about pH 6.5.

8. The pharmaceutical composition of claim 7, wherein the composition is buffered to a pH of about 6.0.

9. The pharmaceutical composition of claim 8, wherein the composition is buffered with a phosphate buffer at a concentration of about 5 mM to about 25 mM.

10. The pharmaceutical composition of claim 9, wherein the composition is buffered with a phosphate buffer at a concentration of about 10 mM.

11. The pharmaceutical composition of claim 3, further comprising insulin.

12. The PEGylated C-peptide of claim 1, wherein n1 and n2 are each within the range of about 400 to 500.

13. The PEGylated C-peptide of claim 1, wherein n1 and n2 are each within the range of about 400 to 650.

* * * * *

```
                        SEQUENCE LISTING

<160> NUMBER OF SEQ ID NOS: 33

<210> SEQ ID NO 1
<211> LENGTH: 31
<212> TYPE: PRT
<213> ORGANISM: Homo sapiens

<400> SEQUENCE: 1

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 2
<211> LENGTH: 31
<212> TYPE: PRT
<213> ORGANISM: Pan troglodytes

<400> SEQUENCE: 2

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 3
<211> LENGTH: 31
<212> TYPE: PRT
<213> ORGANISM: Gorilla gorilla

<400> SEQUENCE: 3

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 4
<211> LENGTH: 31
<212> TYPE: PRT
<213> ORGANISM: Pongo pygmaeus

<400> SEQUENCE: 4

Glu Ala Glu Asp Leu Gln Val Gly Gln Val Glu Leu Gly Gly Gly Pro
1               5                   10                  15
```

Gly Ala Gly Ser Leu Gln Pro Leu Ala Leu Glu Gly Ser Leu Gln
            20                  25                  30

<210> SEQ ID NO 5
<211> LENGTH: 31
<212> TYPE: PRT
<213> ORGANISM: Chlorocebus aethiops

<400> SEQUENCE: 5

Glu Ala Glu Asp Pro Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 6
<211> LENGTH: 31
<212> TYPE: PRT
<213> ORGANISM: Canis lupus familiaris

<400> SEQUENCE: 6

Glu Val Glu Asp Leu Gln Val Arg Asp Val Glu Leu Ala Gly Ala Pro
1               5                   10                  15

Gly Glu Gly Gly Leu Gln Pro Leu Ala Leu Glu Gly Ala Leu Gln
            20                  25                  30

<210> SEQ ID NO 7
<211> LENGTH: 31
<212> TYPE: PRT
<213> ORGANISM: Oryctolagus cuniculus

<400> SEQUENCE: 7

Glu Val Glu Glu Leu Gln Val Gly Gln Ala Glu Leu Gly Gly Gly Pro
1               5                   10                  15

Asp Ala Gly Gly Leu Gln Pro Ser Ala Leu Glu Leu Ala Leu Gln
            20                  25                  30

<210> SEQ ID NO 8
<211> LENGTH: 31
<212> TYPE: PRT
<213> ORGANISM: Rattus norvegicus

<400> SEQUENCE: 8

Glu Val Glu Asp Pro Gln Val Ala Gln Leu Glu Leu Gly Gly Gly Pro
1               5                   10                  15

Gly Ala Gly Asp Leu Gln Thr Leu Ala Leu Glu Val Ala Arg Gln
            20                  25                  30

<210> SEQ ID NO 9
<211> LENGTH: 31
<212> TYPE: PRT
<213> ORGANISM: Apodemus semotus

<400> SEQUENCE: 9

Glu Val Glu Asp Pro Gln Val Ala Gln Leu Glu Leu Gly Gly Gly Pro
1               5                   10                  15

Gly Ala Gly Asp Leu Gln Thr Leu Ala Leu Glu Val Ala Arg Gln
            20                  25                  30

<210> SEQ ID NO 10
<211> LENGTH: 31
<212> TYPE: PRT
<213> ORGANISM: Geodia cydonium

<400> SEQUENCE: 10

Glu Val Glu Asp Pro Gln Val Gly Gln Val Leu Gly Ala Gly Pro
1               5                   10                  15

Gly Ala Gly Ser Glu Gln Thr Leu Ala Leu Glu Val Ala Arg Gln
            20                  25                  30

<210> SEQ ID NO 11
<211> LENGTH: 27
<212> TYPE: PRT
<213> ORGANISM: Mus musculus

<400> SEQUENCE: 11

Glu Val Glu Asp Pro Gln Val Ala Gln Leu Glu Leu Gly Gly Pro
1               5                   10                  15

Gly Ala Gly Asp Leu Gln Thr Leu Ala Leu Glu
            20                  25

<210> SEQ ID NO 12
<211> LENGTH: 27
<212> TYPE: PRT
<213> ORGANISM: Mus caroli

<400> SEQUENCE: 12

Glu Val Glu Asp Pro Gln Val Ala Gln Leu Glu Leu Gly Gly Pro
1               5                   10                  15

Gly Ala Gly Asp Leu Gln Thr Leu Ala Leu Glu
            20                  25

<210> SEQ ID NO 13
<211> LENGTH: 31
<212> TYPE: PRT
<213> ORGANISM: Rattus norvegicus

<400> SEQUENCE: 13

Glu Val Glu Asp Pro Gln Val Pro Gln Leu Glu Leu Gly Gly Pro
1               5                   10                  15

Gly Ala Gly Asp Leu Gln Thr Leu Ala Leu Glu Val Ala Arg Gln
            20                  25                  30

<210> SEQ ID NO 14
<211> LENGTH: 31
<212> TYPE: PRT
<213> ORGANISM: Rattus losea

<400> SEQUENCE: 14

Glu Val Glu Asp Pro Gln Val Ala Gln Gln Glu Leu Gly Gly Pro
1               5                   10                  15

Gly Ala Gly Asp Leu Gln Thr Leu Ala Leu Glu Val Ala Arg Gln
            20                  25                  30

<210> SEQ ID NO 15
<211> LENGTH: 31
<212> TYPE: PRT
<213> ORGANISM: Niviventer coxingi

<400> SEQUENCE: 15

Glu Val Glu Asp Pro Gln Val Pro Gln Leu Glu Leu Gly Gly Pro
1               5                   10                  15

Gly Thr Gly Asp Leu Gln Thr Leu Ala Leu Glu Val Ala Arg Gln
            20                  25                  30

```
<210> SEQ ID NO 16
<211> LENGTH: 26
<212> TYPE: PRT
<213> ORGANISM: Microtus kikuchii

<400> SEQUENCE: 16

Val Glu Asp Pro Gln Val Ala Gln Leu Glu Leu Gly Gly Gly Pro Gly
1               5                   10                  15

Ala Gly Asp Leu Gln Thr Leu Ala Leu Glu
            20                  25

<210> SEQ ID NO 17
<211> LENGTH: 31
<212> TYPE: PRT
<213> ORGANISM: Rattus norvegicus

<400> SEQUENCE: 17

Glu Val Glu Asp Pro Gln Val Pro Gln Leu Glu Leu Gly Gly Gly Pro
1               5                   10                  15

Glu Ala Gly Asp Leu Gln Thr Leu Ala Leu Glu Val Ala Arg Gln
            20                  25                  30

<210> SEQ ID NO 18
<211> LENGTH: 31
<212> TYPE: PRT
<213> ORGANISM: Felis catus

<400> SEQUENCE: 18

Glu Ala Glu Asp Leu Gln Gly Lys Asp Ala Glu Leu Gly Glu Ala Pro
1               5                   10                  15

Gly Ala Gly Gly Leu Gln Pro Ser Ala Leu Glu Ala Pro Leu Gln
            20                  25                  30

<210> SEQ ID NO 19
<211> LENGTH: 26
<212> TYPE: PRT
<213> ORGANISM: Mesocricetus auratus

<400> SEQUENCE: 19

Val Glu Asp Pro Gln Val Ala Gln Leu Glu Leu Gly Gly Gly Pro Gly
1               5                   10                  15

Ala Asp Asp Leu Gln Thr Leu Ala Leu Glu
            20                  25

<210> SEQ ID NO 20
<211> LENGTH: 31
<212> TYPE: PRT
<213> ORGANISM: Niviventer coxingi

<400> SEQUENCE: 20

Glu Val Glu Asp Pro Gln Val Ala Gln Leu Glu Leu Gly Glu Gly Pro
1               5                   10                  15

Glu Ala Gly Asp Leu Gln Thr Leu Ala Leu Glu Val Ala Arg Gln
            20                  25                  30

<210> SEQ ID NO 21
<211> LENGTH: 31
<212> TYPE: PRT
<213> ORGANISM: Apodemus semotus

<400> SEQUENCE: 21

Glu Val Glu Asp Pro Gln Val Glu Gln Leu Glu Leu Gly Gly Ala Pro
```

```
                1               5                   10                  15
Gly Thr Gly Asp Leu Glu Thr Leu Ala Leu Glu Val Ala Arg Gln
            20                  25                  30

<210> SEQ ID NO 22
<211> LENGTH: 31
<212> TYPE: PRT
<213> ORGANISM: Rattus losea

<400> SEQUENCE: 22

Glu Val Glu Asp Pro Gln Val Pro Gln Leu Glu Leu Gly Gly Ser Pro
1               5                   10                  15

Glu Ala Gly Asp Leu Gln Thr Leu Ala Leu Glu Val Ala Arg Gln
            20                  25                  30

<210> SEQ ID NO 23
<211> LENGTH: 30
<212> TYPE: PRT
<213> ORGANISM: Meriones unguiculatus

<400> SEQUENCE: 23

Val Glu Asp Pro Gln Met Pro Gln Leu Glu Leu Gly Gly Ser Pro Gly
1               5                   10                  15

Ala Gly Asp Leu Gln Ala Leu Ala Leu Glu Val Ala Arg Gln
            20                  25                  30

<210> SEQ ID NO 24
<211> LENGTH: 30
<212> TYPE: PRT
<213> ORGANISM: Psammomys obesus

<400> SEQUENCE: 24

Val Asp Asp Pro Gln Met Pro Gln Leu Glu Leu Gly Gly Ser Pro Gly
1               5                   10                  15

Ala Gly Asp Leu Arg Ala Leu Ala Leu Glu Val Ala Arg Gln
            20                  25                  30

<210> SEQ ID NO 25
<211> LENGTH: 26
<212> TYPE: PRT
<213> ORGANISM: Sus scrofa

<400> SEQUENCE: 25

Glu Ala Glu Asn Pro Gln Ala Gly Ala Val Glu Leu Gly Gly Gly Leu
1               5                   10                  15

Gly Gly Leu Gln Ala Leu Ala Leu Glu Gly
            20                  25

<210> SEQ ID NO 26
<211> LENGTH: 31
<212> TYPE: PRT
<213> ORGANISM: Rhinolophus ferrumequinum

<400> SEQUENCE: 26

Glu Val Glu Asp Pro Gln Ala Gly Gln Val Glu Leu Gly Gly Gly Pro
1               5                   10                  15

Gly Thr Gly Gly Leu Gln Ser Leu Ala Leu Glu Gly Pro Pro Gln
            20                  25                  30

<210> SEQ ID NO 27
<211> LENGTH: 31
<212> TYPE: PRT
```

<213> ORGANISM: Equus przewalskii

<400> SEQUENCE: 27

Glu Ala Glu Asp Pro Gln Val Gly Glu Val Leu Gly Gly Gly Pro
1               5                   10                  15

Gly Leu Gly Gly Leu Gln Pro Leu Ala Leu Ala Gly Pro Gln Gln
            20                  25                  30

<210> SEQ ID NO 28
<211> LENGTH: 26
<212> TYPE: PRT
<213> ORGANISM: Bos taurus

<400> SEQUENCE: 28

Glu Val Glu Gly Pro Gln Val Gly Ala Leu Glu Leu Ala Gly Pro
1               5                   10                  15

Gly Ala Gly Gly Leu Glu Gly Pro Pro Gln
            20                  25

<210> SEQ ID NO 29
<211> LENGTH: 31
<212> TYPE: PRT
<213> ORGANISM: Otolemur garnettii

<400> SEQUENCE: 29

Asp Thr Glu Asp Pro Gln Val Gly Gln Val Gly Leu Gly Gly Ser Pro
1               5                   10                  15

Ile Thr Gly Asp Leu Gln Ser Leu Ala Leu Asp Val Pro Pro Gln
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (13)..(24)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid

<400> SEQUENCE: 30

Glu Xaa Glu Xaa Xaa Gln Xaa Xaa Xaa Xaa Glu Leu Xaa Xaa Xaa Xaa
1               5                   10                  15

Xaa Xaa Xaa Xaa Xaa Xaa Xaa Xaa Ala Leu Asx Xaa Xaa Xaa Gln
            20                  25                  30

<210> SEQ ID NO 31
<211> LENGTH: 5
<212> TYPE: PRT
<213> ORGANISM: Artificial Sequence

```
<220> FEATURE:
<223> OTHER INFORMATION: Synthesized

<400> SEQUENCE: 31

Glu Gly Ser Leu Gln
1               5

<210> SEQ ID NO 32
<211> LENGTH: 12
<212> TYPE: PRT
<213> ORGANISM: Artificial Sequence
<220> FEATURE:
<223> OTHER INFORMATION: Synthesized

<400> SEQUENCE: 32

Glu Ala Glu Asp Leu Gln Val Gly Gln Val Glu Leu
1               5                   10

<210> SEQ ID NO 33
<211> LENGTH: 31
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (13)..(24)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid

<400> SEQUENCE: 33

Gly Xaa Glu Xaa Xaa Gln Xaa Xaa Xaa Xaa Glu Leu Xaa Xaa Xaa Xaa
1               5                   10                  15

Xaa Xaa Xaa Xaa Xaa Xaa Xaa Xaa Ala Leu Asx Xaa Xaa Xaa Gln
            20                  25                  30
```